(12) United States Patent
Bourke, Jr. et al.

(10) Patent No.: US 10,391,330 B2
(45) Date of Patent: *Aug. 27, 2019

(54) NON-INVASIVE SYSTEMS AND METHODS FOR IN-SITU PHOTOBIOMODULATION

(71) Applicants: IMMUNOLIGHT, LLC, Detroit, MI (US); DUKE UNIVERSITY, Durham, NC (US)

(72) Inventors: Frederic A. Bourke, Jr., Aspen, CO (US); Tuan Vo-Dinh, Chapel Hill, NC (US); Harold Walder, Belville, NC (US)

(73) Assignees: IMMUNOLIGHT, LLC, Detriot, MI (US); DUKE UNIVERSITY, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/151,642

(22) Filed: May 11, 2016

(65) Prior Publication Data

US 2016/0325111 A1 Nov. 10, 2016

Related U.S. Application Data

(63) Continuation of application No. 12/417,779, filed on Apr. 3, 2009, now abandoned.

(60) Provisional application No. 61/042,561, filed on Apr. 4, 2008.

(51) Int. Cl.
| | |
|---|---|
| *A61N 5/10* | (2006.01) |
| *A61N 5/06* | (2006.01) |
| *A61K 41/00* | (2006.01) |
| *A61N 5/02* | (2006.01) |
| *A61K 47/69* | (2017.01) |

(52) U.S. Cl.
CPC .......... *A61N 5/062* (2013.01); *A61K 41/0057* (2013.01); *A61K 41/0061* (2013.01); *A61K 47/6923* (2017.08); *A61N 5/022* (2013.01); *A61N 5/0618* (2013.01); *A61N 5/0622* (2013.01); *A61N 5/10* (2013.01); *A61N 2005/0642* (2013.01); *A61N 2005/0659* (2013.01); *A61N 2005/0661* (2013.01); *A61N 2005/0662* (2013.01); *A61N 2005/1098* (2013.01)

(58) Field of Classification Search
CPC .. A61K 41/0057; A61N 5/062; A61N 5/0622; A61N 5/10
See application file for complete search history.

(56) References Cited

U.S. PATENT DOCUMENTS

| | | | |
|---|---|---|---|
| 4,111,890 A | 9/1978 | Getson et al. | |
| 4,675,346 A | 5/1987 | Lin et al. | |
| 4,838,852 A | 6/1989 | Edelson | |
| 4,979,935 A | 12/1990 | Lindmayer | |
| 5,118,422 A | 6/1992 | Cooper et al. | |
| 5,120,649 A | 6/1992 | Horowitz | |
| 5,257,970 A | 11/1993 | Dougherty | |
| 5,360,734 A | 11/1994 | Chapman et al. | |
| 5,489,590 A | 2/1996 | Gulliya et al. | |
| 5,521,289 A | 5/1996 | Hainfeld | |
| 5,728,590 A | 3/1998 | Powell | |
| 5,829,448 A | 11/1998 | Fisher | |
| 5,912,257 A | 6/1999 | Prasad et al. | |
| 5,957,960 A | 9/1999 | Chen | |
| 5,980,954 A | 11/1999 | Bolton | |
| 6,036,941 A | 3/2000 | Bottiroll | |
| 6,042,603 A | 3/2000 | Fisher et al. | |
| 6,051,625 A | 4/2000 | Harkness et al. | |
| 6,071,944 A | 6/2000 | Rodgers | |
| 6,087,141 A | 7/2000 | Margolis-Nunno | |
| 6,121,425 A | 9/2000 | Hainfeld | |
| 6,204,058 B1 | 3/2001 | Bolton | |
| 6,225,333 B1 | 5/2001 | Rodgers | |

(Continued)

FOREIGN PATENT DOCUMENTS

| | | |
|---|---|---|
| JP | 09038503 | 2/1997 |
| JP | 09299937 | 11/1997 |

(Continued)

OTHER PUBLICATIONS

Combined Taiwanese Office Action and Search Report dated Jun. 14, 2017 (with English Translation of Search Report).
Office Action dated Aug. 14, 2017 in Japanese Patent Application No. 2016-113368 (with English language translation).
European Office Action dated Feb. 27, 2017 in Application No. 09 726 873.4.
Office Action dated Jan. 30, 2017 in Japanese Patent Application No. 2016-075090 (with English translation).
Office Action dated Mar. 27, 2017 in Japanese Patent Application No. 2016-113368 (with English translation).
Jean R. Starkey, et al., "New two-photon activated photodynamic therapy sensitizers induce xenograft tumor regressions after near-IR laser treatment through the body of the host mouse", Clin Cancer Res 2008;14(20), Oct. 15, 2008, pp. 6564-6573.

(Continued)

*Primary Examiner* — James D. Anderson
(74) *Attorney, Agent, or Firm* — Oblon, McClelland, Maier & Neustadt, L.L.P.

(57) ABSTRACT

Products, compositions, systems, and methods for modifying a target structure which mediates or is associated with a biological activity, including treatment of conditions, disorders, or diseases mediated by or associated with a target structure, such as a virus, cell, subcellular structure or extracellular structure. The methods may be performed in situ in a non-invasive manner by application of an initiation energy to a subject thus producing an effect on or change to the target structure directly or via a modulation agent. The methods may further be performed by application of an initiation energy to a subject in situ to activate a pharmaceutical agent directly or via an energy modulation agent, optionally in the presence of one or more plasmonics active agents, thus producing an effect on or change to the target structure. Kits containing products or compositions formulated or configured and systems for use in practicing these methods.

6 Claims, 37 Drawing Sheets

(56) References Cited

U.S. PATENT DOCUMENTS

| | | | |
|---|---|---|---|
| 6,235,508 B1 | 5/2001 | Sowemimo-Coker et al. | |
| 6,281,261 B1 | 8/2001 | Bennington | |
| 6,323,253 B1 | 11/2001 | Bennington | |
| 6,569,467 B1 | 5/2003 | Bolton | |
| 6,609,014 B1 | 8/2003 | Allison et al. | |
| 6,627,923 B1 | 9/2003 | Lipson et al. | |
| 6,669,965 B2 | 12/2003 | Bolton | |
| 6,670,013 B2 | 12/2003 | Hainfeld | |
| 6,811,562 B1 | 11/2004 | Pless | |
| 6,849,058 B1 | 2/2005 | Levy | |
| 6,955,639 B2 | 10/2005 | Hainfeld | |
| 7,008,559 B2 | 3/2006 | Chen | |
| 7,045,124 B1 | 5/2006 | Hamet | |
| 7,183,072 B1 | 2/2007 | Hainfeld | |
| 7,267,948 B2 | 9/2007 | Vo-Dinh | |
| 7,294,656 B2 | 11/2007 | Bach et al. | |
| 7,364,872 B1 | 4/2008 | Hainfeld | |
| 7,367,934 B2 | 5/2008 | Hainfeld et al. | |
| 7,530,940 B2 | 5/2009 | Hainfeld et al. | |
| 8,770,203 B2 * | 7/2014 | Bourke, Jr. | A61K 41/008 128/898 |
| 9,283,275 B2 * | 3/2016 | Vo-Dinh | A61K 39/00 |
| 9,358,292 B2 * | 6/2016 | Bourke, Jr. | A61K 47/02 |
| 9,439,897 B2 * | 9/2016 | Xia | A61K 31/436 |
| 9,498,643 B2 * | 11/2016 | Bourke, Jr. | A23L 3/26 |
| 9,682,146 B2 * | 6/2017 | Bourke, Jr. | A61K 41/00 |
| 9,682,250 B2 * | 6/2017 | Bourke, Jr. | A61N 5/10 |
| 2002/0127224 A1 | 9/2002 | Chen | |
| 2003/0022170 A1 | 1/2003 | Khodadoust | |
| 2004/0214001 A1 | 10/2004 | Oldenburg et al. | |
| 2004/0253138 A1 * | 12/2004 | Malak | A61L 2/0011 422/22 |
| 2005/0020869 A1 | 1/2005 | Hainfeld | |
| 2005/0187595 A1 | 8/2005 | Streeter | |
| 2006/0067889 A1 | 3/2006 | Pallenberg | |
| 2006/0255292 A1 | 11/2006 | Ja | |
| 2007/0059316 A1 | 3/2007 | Pallenberg | |
| 2007/0063154 A1 | 3/2007 | Chen et al. | |
| 2007/0189359 A1 | 8/2007 | Chen et al. | |
| 2007/0217996 A1 | 9/2007 | Levy et al. | |
| 2007/0218049 A1 | 9/2007 | Chen | |
| 2007/0243137 A1 | 10/2007 | Hainfeld | |
| 2007/0274909 A1 | 11/2007 | Justel et al. | |
| 2007/0292353 A1 | 12/2007 | Levy et al. | |
| 2008/0003183 A1 | 1/2008 | Guo | |
| 2008/0039436 A1 | 2/2008 | Patel | |
| 2008/0089836 A1 | 4/2008 | Hainfeld | |
| 2008/0139993 A1 | 6/2008 | Bensaoula et al. | |
| 2008/0248001 A1 | 10/2008 | Bourke | |
| 2009/0104212 A1 | 4/2009 | Bourke | |
| 2011/0171184 A1 | 7/2011 | Hovig et al. | |

FOREIGN PATENT DOCUMENTS

| | | |
|---|---|---|
| JP | 2004-514724 A | 5/2004 |
| JP | 2004-532251 A | 10/2004 |
| JP | 2005-503388 A | 2/2005 |
| JP | 2006-290840 A | 10/2006 |
| JP | 2008-505633 A | 2/2008 |
| JP | 2011-503172 A | 1/2011 |
| WO | WO 98/04318 A1 | 2/1998 |
| WO | WO 02/44187 A2 | 6/2002 |
| WO | WO 02/096366 A2 | 12/2002 |
| WO | WO 03/017824 A2 | 3/2003 |
| WO | 03/049801 | 6/2003 |
| WO | 05/030254 | 4/2005 |
| WO | WO 2005/099369 A2 | 10/2005 |
| WO | WO 2006/013390 A1 | 2/2006 |
| WO | 2006/037081 A2 | 4/2006 |
| WO | WO 2006/053225 A2 | 5/2006 |
| WO | WO 2006/078987 A2 | 7/2006 |
| WO | WO 2006/122222 A2 | 11/2006 |
| WO | 2007/048635 | 5/2007 |
| WO | 2007/108512 | 9/2007 |
| WO | WO 2007/106415 A2 | 9/2007 |
| WO | 2008/007290 A2 | 1/2008 |
| WO | WO 2008/124681 A2 | 10/2008 |
| WO | WO 2009/114567 A1 | 9/2009 |

OTHER PUBLICATIONS

Yongjun Chen, et al., "Apoptosis induced by methylene-blue-mediated photodynamic therapy in melanomas and the involvement of mitochondrial dysfunction revealed by proteomics", Cancer Sci, Oct. 2008, vol. 99, No. 10, pp. 2019-2027.

Ashwin A. Bhirde, et al., "Targeted killing of cancer cells in vivo and in vitro with EGF-directed carbon nanotube-based drug delivery", ACSNANO, vol. 3, No. 2, 2009, pp. 307-316.

Luo Jun-Ming, et al., "Fabrication and Up-conversion luminescence of Er3+:Y2O3 nanoparticles", Journal of Nanoscience and Nanotechnology, vol. 8, 2008, pp. 1211-1213.

Petras Juzenas, et al., "Quantum dots and nanoparticles for photodynamic and radiation therapies of cancer", Advanced Drug Delivery Reviews, (2008), 15 pages.

Pil-Souk G. Kim, et al., "X-ray-Excited optical luminescence (XEOL) and X-ray absorption fine structures (XAFS) studies of gold(I) complexes with diphosphine and bipyridine ligands", Inorganic Chemistry, vol. 46, No. 3, 2007, pp. 949-957.

Parmeswaran Diagaradjane, et al., "Modulation of in vivo tumor radiation response via gold nanoshell-mediated vascular-focused hyperthermia: characterizing an integrated antihypoxic and localized vascular disrupting targeting strategy", American Chemical Society, Nano Letters, vol. 8, No. 5, 2008, pp. 1492-1500.

Jon A. Wolff, et al. "Breaking the Bonds: Non-viral Vectors Become Chemically Dynamic" Molecular Therapy, The American Society of Gene Therapy, www.moleculartherapy.org, vol. 16, No. 1, Oct. 23, 2007, pp. 8-15.

Douglas D. Young, et al. "Photochemical control of biological processes" Organic & Biomolecular Chemistry, The Royal Society of Chemistry, Dec. 20$^{th}$, 2006, 5, pp. 999-1005.

Feng Zhang, et al. "Channelrhodopsin-2 and optical control of excitable cells" Nature Methods, vol. 3, No. 10, Oct. 2006, pp. 785-792.

K. Jensen, et al. "Nanotube Radio: Supplementary Materials" Center of Integrated Nanomechanical Systems, http://physics.berkeley,.edu./research/zettl/projects/nanoradio/radio.html, 2007, 4 pages.

Zhang F. Wang LP, et al., Comment in "Nature", Apr. 5, 2007; 446(7136): 617-9, (abstract)-AbstractPlus.

S.D. Zakharov et al., "Light-oxygen effect in cells and its potential applications in tumour therapy (review)" IOP Electronic Journals, Quantum Electronics, 29, Issue 12, (1999), Abstract.

H. Wang et al., "High-speed mapping of synaptic connectivity using photosimulation in Channelrhodopsin-2 transgenic mice", PNAS, May 8, 2007, vol. 104, No. 19, pp. 8143-8148.

Dr. G McConnell, "Visit to LaSIE (Apr. 2008): initiating an international collaboration to develop laser sources for spatially-localised, deep-tissue photostimulation", EPSRC, Osaka University, EPSRC Reference: EP/F036213/1.

Katleen Braet et al., "Photoliberating Inositol-1,4,5-Trisphosphate Triggers ATP Release That is Blocked by the Connexin Mimetic Peptide Gap 26", Churchill Livingstone, Cell Calcium 33, 2003, pp. 37-48, (12pp.).

Karel Svoboda, "New Studies Illuminate the Computational Power of Neurons", HHMI, Research News, Dec. 20, 2007, (3pp.).

Photobiomodulation, Wikipedia, downloaded from http://en.wikipedia.org/wiki/Laser_therapy on Mar. 26, 2008, (2pp.).

Science News, "Pulsing Light Silences Overactive Neurons", ScienceDaily, Mar. 28, 2007, downloaded from http://sciencedaily.com/releases/2007/03/070327161418.htm on Mar. 26, 2008, (2pp.).

Timothy C. Zhu, "Modeling of Singlet Oxygen During Photodynamic Therapy Using COMSOL Multiphysics", Expert from the Proceedings of the COMSOL Users Conference 2006 Boston, (5pp.).

Fernando L. Primo et al., "Magnetic Nanoemulsions as Drug Delivery System for Foscan : Skin Permeation and retension in Vitro Assays for Topical Application in Photodynamic Therapy

(56) References Cited

OTHER PUBLICATIONS (PDT) of Skin Cancer", Journal of Magnetism and Magnetic Materials 311, (2007), pp. 354-357, available online at www.sciencedirect.com , (5pp.).
Harry A. Atwater, "The Promise of Plasmonics, a Technology the Squeezed Electromagnetic Waves into Minuscule Structures May Yield a New Generation of Superfast Computer Chips and Ultrasensitive Molecular Detectors", Scientific American Magazine—Mar. 18, 2007, http://www.sciam.com/arlicle.cfm?id=the-promise-of-plasmonics&pring=true , (4pp.).
Carraro C, Pathak MA., "Studies on the Nature of In Vitro and In Vivo Photosensitization Reactions by Psoralens and Porphyrins", J. Invest Dermatol. 1988, Mach 90(3) pp. 267-275, Abstract, (1 pp.).
Xiaodong Wang, "The Expanding Role of Mitochondria in Apoptosis", Genes & Development, 15, 2001, pp. 2922-2933, www.genesdev.org (12 pp.).
Reproductive and Cardiovascular Disease Research Group, downloaded from http://www.sgul.ao.uk/depts/immunology/~dash/apoptosis/mito.htm on May 22, 2008, (4pp.).
Noah Scheinfeld, et al., "A Review of Studies that Have Utilized Different Combinations of Psoralen and Ultraviolet B Phototherapy and Ultraviolet A Phototherapy", Dermatology Online Journal, vol. 9, No. 5., downloaded from http://dermatology.cdlib.org/95/reviews/uv/scheinfeld.html on May 22, 2008, (8pp.).
Karen S. McGinnis, et al., "An effective and Synergistic Combined Adjunct to Therapy for Patients with Advances Cutaneous T-Cell Lymphoma", Psoralen Plus Long-Wave UV-A (PUVA) and Bexarotene Therapy, Arch Dermatol., /vol. 139, 2003, pp. 771-775,downloaded from www.archdermatol.com May 22, 2008, (5pp.).
AB Santamaria et al., "p53 and Fas Ligand are Required for Psoralen and UVA-Induces Apoptosis in Mouse Epidermal Cells", Cell Death and Differentiation (200) 9, pp. 549-560, www.nature.com/cdd (12pp.).
Pathak MA., "Mechanism of psoralen photosensitization reactions", Natl Cancer Insti. Monogr, Dec. 1984: 66:41-6, Abstract, downloaded from http://www.ncbi.nlm.nih.gov/pubmed/65310313 on May 22, 2008, (1pp.).
Stanley G. Rockson, et al., "Photoangioplasty: An Emerging Clinical Cardiovascular Role for Photodynamic Therapy", Journal of the American Heart Association, Circulation 2000; 102; pp. 591-696, downloade form http://cir.ahajournals.org/cgi/content/full/102/5/591 on Mar. 26, 2008,(7pp.).
York N. Hsiang et al., "Determining Light Dose for Photodynamic Therapy of Atherosclerotic Lesions in the Yucatan Miniswine", J. Endovasc Surg, 1995, 2, pp. 365-371. (7pp.).
Margaret T. T. Wong-Riley et al., "Photobiomodulation Directly Benefits Primary Neurons Functionally Inactivated by Toxins", The Journal of Biological Chemistry, 2005, vol. 280, No. 6, Issue of Feb. 11. pp. 4761-47771, downloaded form www.jbc.org on Mar. 27, 2008, (11pp.).
Harry Whelan, et al., "Harnessing the Cell's Own Ability to Repair and Prevent Neurodegenerative Disease", Spie, Newsroom, 10.1117/2.1200802.1014, 2008, (3pp.).
Feng Zhang et al., "Channelrhodopsin-2 and Optical Control of Excitable Cells", Nature Methods, vol. 3, No. 10, Oct. 2006, pp. 785-792, http://www.nature.com/naturemethods (8pp.).
H. Wang et al., "High-speed Mapping of Synaptic Connectivity Using Photostimulation in Channelrhodopsin-2 Transgenic mice", PNAS, May 8, 2007, vol. 104, No. 19, pp. 8143-8148, www.pnas.org/cgi/doi/10.1073/pnas.0700384104 (6pp.).
John G. McCarron, et al"Origin and Mechanisms of $Ca^{2+}$ Waves in Smooth Muscle as Revealed by Localized Photolysis of Caged Inositol 1,4,5,-Trisphosphate", The Journal of Biological Chemistry, vol. 279, No. 9, Issue of Feb. 27, pp. 8417-8427, downloaded from http://www.jbc.org on Mar. 5, 2008, (1pp.).
S D Zakharov et al, "Light-Oxygen Effect in Cells and its Potential Applications in Tumour Therapy(review", Quantum Electronics 29 (12), 1999, pp. 1031-1053, (23pp.).
Daniel Huber et al., "Sparse Optical Microstirnulation in Barrel Cortex Drives Learned Behaviour in Freely Moving Mice", vol. 451, Jan. 3, 2008, doi:10.1038, Nature 06445, Letters (6pp.).
Christopher D. Harvey et al., "Locally Dynamic Synaptic Learning Rules in Pyramidal Neuron Dendrites", vol. 450, Dec. 20-27, 2007, doi:10.1038, Nature 06416, Articles, (8pp.).
Antoine R. Adamantidis et al., "Neural Substrates of Awakening Probed with Optogenec Controll of Hypocretin Neurons", vol. 450, Nov. 15, 2007, doi: 10.1038, Nature 06310, Letters, (6pp.).
N. I. Smith et al., "Photostimulation of Two Types of $Ca^{2+}$ Waves in Rat Pheochoromocytoma PC12 Cells by Ultrashort Pulsed Near-infrated Laser Irradiation", Letters, Wilwy-VCH Verlag GmbH & Co. DGaA, Published Oct. 13, 2005, (8pp.).
Susana W. Lima et al., "Remote Control of Behavior Through Genetically Targeted Photostimulation of Neurons", Resource Department of Cell Biology, Yale University School of Medicine, Cell, vol. 121, Apr. 8, 2005, pp. 141-152, (12pp.).
Matthias Eder et al., "Shining Light on Neurons—Elucidation of Neuronal Functions by Photostimulation", Clinical Neuropharmacology, Max-Planck-Institute of Psychiatry, Munich, Germany, Reviews in the Neurosciences, 15, 2004, pp. 167-183, (16pp.).
Bisaccia E., et al., "Extracorporeal photopheresis in the treatment of AIDS-related complex: extended trial", J. Acuir. Immune Defic. Syndr., Apr. 1993; 6(4): pp. 386-392, (abstract)-AbstractPlus.
Martina E. Wieder, "Intracellular photodynamic therapy with photosensitizer-nanoparticle conjugates: cancer therapy using a 'Trojan horse'", Photochem. & Photobiol. Sci., 2006, 5, pp. 727-734.
Petras Juzenas, et al., "Quantum dots and nanoparticles for photodynamic and radiation therapies of cancer", ScienceDirect, Advanced Drug Delivery Reviews, vol. 60, Dec. 14, 2008, pp. 1600-1614, abstract.
Hede Shantesh et al., ""Nano": The new nemesis of cancer", Journal of Cancer Research and Therapeutics, vol. 2, No. 4, Oct.-Dec. 2006, pp. 186-195.
Maksym Yezhelyev, et al., "Inorganic Nanoparticles for predictive oncology of breast cancer", Nanomedicine, 2009, 4 (1), pp. 83-103, www.medscape.com.
James Hainfeld, et al., "Scientists in the US have shown that gold nanoparticles can help X-rays kill cancerous cells more effectively in mice. The team hopes to refine the technique so that it will eventually work on humans" (J. Hainfeld et al., 2004, Phys. Med. Biol., 49, N309).
Sonia Kumar, et al., "Optical molecular imaging agents for cancer diagnostics and therapeutics", Nonomedicine, Future Medicine, 2006, 1(1), pp. 23-30.
Richard L. Edelson, M.D., "Photopheresis: A new therapeutic concept", The Yale Journal of Biology and Medicine, vol. 62, (1989), pp. 565-577.
Stanley G. Rockson, et al., "Photoangioplasty: an emerging clinical cardiovascular role for photodynamic therapy", Circulation, Journal of the American Heart Association, 2000, 102, pp. 591-596.
York N. Hsiang, MD. et al., "Determining light dose for photodynamic therapy of atherosclerotic lesions in the Yucatan miniswine", Journal Endovasc. Surg., 1995; 2: pp. 365-371.
Judy Foreman, "What is green light laser therapy to treat an enlarged prostate?", Health Answers, News, Sep. 3, 2007, www.boston.com/news/globe/health_scince/articles/2007/09/03/what_is_light.
Competitive Binging Data with one Class of Receptors, Fitting data to a one-site competitive binding curve, http://www.graphpad.com/curvefit/one_kind_of_receptor.htm , 1999, (3pp.).
Jacky Lyden, "Good Vibrations Emanate from Nanotube", NPR, Nov. 5, 2007, downloaded from http://www.npr.org/templates/story/story.php?storyId=15868800 on Nov. 5, 2007, (5pp.).
Martina E. Wieder et al., "Intracellular Photodynamic Therapy with Photosensitizer-nanoparticle Conjugates: Cancer Therapy Using a 'Trojan horse' ", The Royal Society of Chemistry and Owner Societies, Photochemical & Photobiol.I Sci., 2006, 5, pp. 727-734, www.rsc.org/pps , (8pp.).
Xiaohue Huang et al., "Plasmonic Photothermal Therapy (PPTT) Using Gold Nanoparticles", Review Article, Laser Med. Sci., 2007, (12pp.).

(56) References Cited

OTHER PUBLICATIONS

Ernst Wagner, "Programmed Drug Delivery: Nanosystems for Tumor Targeting", Editorial, Expert Opinion Biol. Ther. 2007, 7(5), pp. 587-593, (7pp.).
Giuseppe Palumbo, "Photodynamic Therapy and Cancer: a Brief Sightseeing Tour", Review, Expert Opinion, Drug Deilv. 2007, 4(2), pp. 131-148, (18pp.).
Sehoon Kim et al., "Organically Modified Silica Nanoparticles Co-encapsulating Photosensitizing Drug and Aggregation-Enhances Two-Photon Absorbing Fluorescent Dye Aggregates for Two-Photon Photodynamic Therapy", JACS Articles, J. Am. Chem. Soc., vol. 129, No. 9, 2007, (8pp.).
Ivan Charamisinau et al., "Semiconductor Laser Insert with Uniform Illumination for Use in Photodynamic Therapy", Applied Optics, Aug. 20, 2005, vol. 44, No. 24, pp. 5055-5068, (14pp.).
Brian M. Caullum, "Smart Medical and Biomedical Sensor Technology", Spie Proceeding Series—The International Society for Optical Engineering, vol. 5261, Oct. 28-29, 2003, (14pp.).
Akimichi Morita et al, "Evidence that Singlet Oxygen-Induced Human T. Helper Cell Apoptosis is the Basic Mechanism of Ultraviolet-A Radiation Phototherapy", Brief Definitive Report, J. Exp. Med., vol. 186, No. 10, Nov. 17, 1997, pp. 1763-1768, downloaded from http://www.jem.org on Sep. 6, 2007, (6pp.).
M. F. Nichols et al., "Oxygen Diffusion and Reaction Kinetics in the Photodynamic Therapy of Multicell Tumour Speroid", Phys. Med. Biol. 39, 1994, 2161-2181, (21pp.).
H. Peter Van Iperen et al., "Singlet Oxygen Producing Photosensitizers in Photophoresis", Journal of Photochemistry and Photobiology B: Biology 38, 1997, pp. 203-208, (6pp.).
Irene Georgakoudi et al."The Mechanism of Photofrin © Photobleaching and Its Consequences for Photodynamic Dosimetry", Photochemistry and Photobiology, 1997, 65(1), pp. 135-144, 10pp.).
Brian W. Pogue et al.,"A Photobiological and Photophysical-based Study of Phototoxicity of Two Chlorins[1]", Cancer Research 61, Jan. 15, 2001, pp. 717-724, (8pp.).
Wei Chen et al., "Using Nanoparticles to Enable Simultaneous Radiation and Photodynamic Therapies for Cancer Treatment", J. Nanoscience Nanotechnology, 2006, vol. 6, No. 4, pp. 1159-1166, (8pp.).
Junkoh Yamamoto et al., "Monitoring of Singlet Oxygen Is Useful for Predicting the Photodynamic Effects in the Treatment for Experimental Glioma", Clin Cancer Res 2006: 12(23) Dec. 1, 2008, pp. 7132-7139, www.aacrjournals.org, (10pp.).
Jurgen Baler et al, "Direct Detection of Singlet Oxygen Generated by UVA Irradiation in Human Cells and Skin", Original Article, Journal of Investigative Dermatology, 2007, vol. 127, pp. 1498-1506, (9pp.).
Godwin DW, et al., "Photostimulation with Caged Neurotransmitters Using Fiber Optic Lightguides", J. Neurosci Methods, Apr. 25, 1997;73(1):91-106, Abstract, http://www.ncbi.nlm.nlh.gov/pubmed/9130682 , (1pp.).
Kadir Asian et al., "Multicolor Microwave-Triggered Metal-Enhances Chemiluminescence", JACS Communication, J. Am. Chem. Soc., online published Sep. 23, 2006, (6pp.).
F.V. Santos et al., "Photocatalysts as a Tertiary Treatment for Petroleum Refinery Wastewaters", Brazilian Journal of Chemical Engineering, vol. 23, No. 04, Oct.-Dec. 2006, pp. 451-460, www.abeg.org.br/bjche , (10pp.).
Mal Thu Thi Tran et al., "Ultraviolet Treatment of Orange Juice", Elsevier, Innovative Food Science and Emerging Technologies 5 (2004), pp. 495-502, www.s.sciencedirect.com , (8pp.).
M. Thoms[aO] et al., "Method for the determination of Photostimulable defect Center Concentrations, Production Rates, and Effective Formation Energies", J. Appl. Phys. 75 (9), May 1, 1994, (4pp.).
Surbhi Lal et al., "Nano-optics from Sensing to Wavegulding", Review Article, Nature Photonics, vol. 1, Nov. 2007, pp. 641-648. www.nature.com/naturephotonics, (8pp.)
Mustafa H. Chowdhury et al., "Metal-Enhanced Fluorescence of Phycobiliprotein from Heterogeneous Plasmonic Nanostruoutures", J. Phys. Chem. C 2007, 111, pp. 18856-18863, Articles, (8pp.).

Harry A. Atwater, "The Promise of Plasmonics", Scientific American, published Apr. 2007, www.sciam.com, (8pp.).
Stefan A. Maier, "Plasmonic Field Enhancement and SERS in the Effective Mode Volume Picture", Optics Express, Mar. 6, 2006/ vol. 14, No. 5, pp. 1957-1964, (8pp.).
De Bary Aqua—UV, "Sterilizers for Frest or Marine Water Aquarium, Garden Ponds, Breeder Tanks and Commercial Applications in the Molluscan Shellfish Industry", Info. A4-GB-Nov. 2002, (4pp.).
Dr. Roger McCartney. Consultant, Fusion UV Systems, Inc., "UV Cocooning: CMTI Emissions Testing Results", Composites 2002 Convention and Trade Show Composites Fabricators Association, Sep. 25-27, 2002, Atlanta, Georgia USA, (11pp.).
Aaron P. VanDevender el al., "Quantum Transduction via Frequency Upconversion" (Invited), J. Opt. Soc. Am., vol. 24, No. 2, Feb. 2007, pp. 295-297, (5pp.).
Aslan Kadir et al., "Fast and Sensitive DNA Hybridization Assays Using Microwave-accelerated Metal-enhanced Fluorescence", ScienceDirect, Biochemical and Biophysical Research Communications 348 (2006) pp. 612-617, www.sciencedirect.com, (6pp.).
Shaomin Wang et al., "Electromagnetic Excitation of Nano-carbon in Vacuum", Optics Express, May 16, 2005, vol. 13, No. 10, 3625, (6pp.).
Kadir Asian et el., "Microwave-Accelerated Metal-Enhanced Fluorescence (MAMEF) with Silver Colloids in 96-well Plates: Application to Ultra Fast and Sensitive Immunoassays, High Throughput Screening and Drug Discovery", Journal of Immunological Method 312 (2006) pp. 137-147, (11pp.).
David J. Hurrell, Sterilization, "Recent Developments in Sterilization Technology", Medical Device Link, the Online information Source for the Medical Device Industry , Medical Plastics and Biomaterials Magazine PB Article Index, published Sep. 1998, downloaded from http://www.devicelink.com/mpb/archive/98/09/002.html, on May 19, 2008, (8pp.).
Han X, et al., "Multiple-color Optical Activation, Silencing, and Desynchronization of Neural Activity, with Single-Spike Temporal Resolution", PLoS One, Mar. 21, 2007; 2(3):e299, Abstract, downloaded form www.ncbi.nlm.nlh.gov on Apr. 2, 2008, (1pp.).
N.I.Smith et al., "Photostimulation of Two Types of $Ca^{2+}$ Waves in Rat Pheochoromocytoma PC12 Cells by Ultrashort Pulsed Near-infrared Laser Irradiation", Laser Physics Letters, vol. 3, issue 3, pp. 154-216, published online Oct. 13, 2005, downloaded from http://www.3.interscience.wiley.com on Mar. 4, 2008, Abstract, (1pp.).
Katz LC, et al., "Scanning Laser Photostimulation: A New Approach for analyzing Brain Circuits", J. Neurosci Methods, Oct. 1994:54 (2):205-18, Abstract, downloaded from http://www.ncbi.nlm.nih.gov/pubmed/7869753 on Mar. 4, 2008, (1pp.).
Cha-Min Tang, "Unit 6.21 Photolysis of Caged Neurotransmitters: Theory and Procedures for Light Delivery", InterScience, Baltimore VA Medical Center and University of Maryland School of Medicine, Abstract, 2000, (1pp.).
Liang-yan Xue, et al., "The death of human cancer cells following photodynamic therapy: apoptosis competence is necessary for Bcl-2 protection but not for induction of autophagy", Photochemistry and Photobiology, 2007, 83: pp. 1016-1023.
Mamta Khurana, et al., "Quantitative in vitro demonstration of two-photon photodynamic therapy using photofrin and visudyne", Photochemistry and Photobiology, 2007, 83; pp. 1441-1448.
Dakrong Pissuwan, et al., "Targeted destruction of murine macrophage cells with bioconjugated gold nanorods", Journal of Nanoparticle Research (2007) 9: pp. 1109-1124.
Kazuyuki Ishii, et al., "Control of photobleaching in photodynamic therapy using the photodecarbonylation reaction of ruthenium phthalocyanine complexes via stepwise two-photon excitation", Journal of Phys. Chem. B 2008, 112, pp. 3138-3143.
Qingling Wan, et al., "Bid is required in NPe6-PDT-induced apoptosis", Photochemistry and Photobiology, 2008, 84: pp. 250-257.
Quanhong Liu, et al., "Sonodynamic antitumor effect of protoporphyrin IX disodium salt on S180 solid tumor", Experimental Chemotherapy, Chemotherapy, 2007; 53: pp. 429-436.
Liping Song, et al., "Naphthalocyanine-reconstituted LDL nanoparticles for in vivo cancer imaging and treatment", International Journal of Nanomedicine, 2007: 2(4), pp. 767-774.

(56) References Cited

OTHER PUBLICATIONS

Garif Akchurin, et al., "Gold nanoshell photomodification under a single-nanosecond laser pulse accompanied by color-shifting and bubble formation phenomena", Nanotechnology 19, (2008), 015701, 8 pp.
Express, Oct. 23, 2008, Thursday, "Peeled scotch tape emits x-rays" 1 pp.
Martina E. Wieder, et al., Intracellular photodynamic therapy with photosensitizer-nanoparticle conjugates: cancer therapy using a 'Trojan horse', Photochemical & Photobiological Sciences, 2006, 5, pp. 727-734.
Yuanfang Liu, et al., "Investigation of water-soluble x-ray luminescence nanoparticles for photodynamic activation", Applied Physics Letter 92, 043901, (2008), 043901-1 to 043901-3.
Peng Zhang, et al., "Versatile photosensitizers for photodynamic therapy at infrared excitation", Journal of the American Chemical Society, vol. 129, 2007, No. 15, pp. 4526-4527.
Shane O. McDonnell, et al., "Supramolecular photonic therapeutic agents", Journal of the American Chemical Society, 2005, 127, pp. 16360-16361.
John G. McCarron, et al., "Origin and mechanisms of $Ca^{2+}$ waves in smooth muscle as revealed by localized photolysis of caged inositol 1,4,5-trisphophate", The Journal of Biological Chemistry, vol. 279, No. 9, 2004, pp. 8417-8427.
Edward M. Callaway, et al., "Photostimulation using caged glutamate reveals functional circuitry in living bans ices", Proc. Natl. Acad. Sci. USA, vol. 90, Aug. 1993, pp. 7661-7665.
Katz LC, et al., "Scanning laser photostimulation: a new approach for analyzing brain circuits", J. Neurosci Methods, Oct. 1994; 54(2), pp. 205-218, (abstract)-AbstractPlus.
Godwin DW., et al., "photostimulation with caged neurotransmitters using fiber optic lightguides", J. Neurosci. Methods, Apr. 25, 1997:73(1), pp. 91-106, abstract.
Katleen Braet, et al., "Photoliberating inositol-1,4,5-trisphosphate triggers ATP release that is blocked by the connexin mimetic peptide gap 26", Cell Calcium 33, (2003), pp. 37-48.
Matthias Eder, et al., "Shining light on neurons-elucidation of neuronal functions by photostimulation", Reviews in the Neurosciences, 15, (2004), pp. 167-183.
Susana Q. Lima, et al., "Remote control of behavior through genetically targeted photostimulation of neurons", Cell vol. 121, Apr. 8, 2005, pp. 141-152.
Antoine R. Adamantidis, et al., "Neural substrates of awakening probed with optogenetic control of hypocretin neurons", Nature Letters, vol. 450, Nov. 15, 2007, pp. 420-425.
Christopher D. Harvey, et al., "Locally dynamic synaptic learning rules in pyramidal neuron dendrites", Nature Articles, vol. 450, Dec. 20-27, 2007, pp. 1195-1202.
Daniel Huber, et al., "Sparse optical microstimulation in barrel cortex drives learned behaviour in freely moving mice", Nature Letters, vol. 451, Jan. 3, 2008, pp. 61-66.
S. D. Zakharov, et al., "Light-oxygen effect in cells and its potential applications in tumour therapy (review)", Quantum Electronics 29, (12), (1999), pp. 1031-1053.
Science News, Scientist Directly Control Brain Cell Activity With Light, ScienceDaily, Apr. 5, 2007, downloaded from http://www.sciencedaily.com/releases/2007/04/070704162400.htm on Mar. 26, 2008 , (2pp.).
ScienceDaily, Optical Technique Studies Brain Activity without Surgery on Skull, Aug. 2, 2001 Champaign, III, downloaded from http://www.sciencedaily.com/releases/2001/08/010802081211.htm on Mar. 26, 2008 , (2pp.).
Jay Motola, "Enlarged Prostate Treatment: Green Light PVP", ProstateCommons.com, Monday, Nov. 5, 2007, downloaded from http://healthcentral.com/prostate/c/95/15917/gree-light-pvp/ on Mar. 26, 2008, (2pp.).
Judy Foreman, "What is'Green Light' Laser Therapy to Treat an enlarged Prostate?", The Boston Globe, Health Answers, Sep. 3, 2007, downloaded form http://.boston.com/news/golbe/health_science/articles/2007/09/03/what_is_green_light , on Mar. 26, 2008, (2pp.).
Prof. Tiina Karu's, "Cellular Mechanism of Low-Power Laser Therapy", Photobiomodulation, downloaded from www.tinnitus.us/tiinakarupresentaion.html on Mar. 26, 2008, (6pp.).
Pascal Carmody Medical Director, "Photodynamic Therapy", The Photodynamic Treatment Center at East Clinic, Killaloe, Co. Clare, Ireland, http://www.famma.ru/technical/articles-1/photodynamic_therapy.htm downloaded on Mar. 26, 2008, (4pp.).
William E. Grant, et al., "Photodynamic Therapy of Arteries: Preservation of Mechanical Integrity", Photodynamic Therapy of Arteries: Preservation of Mechanical Integrity, http://www.lumacare.com/paper6.htm downloaded on Mar. 26, 2008, (6pp.).
S D Zakharov et al., Light-Oxygen Effect in Cells and its Potential Applications in Tumor Therapy (review), Quantum electron, 29, pp, 1031-1053, 1999, Abstract, http://www.iop.org/EJ/abstract/1063-7818/29/12/r03 , downloaded on Mar. 26, 2008,(1pp.).
Zhang F. et al., "Multimodal Fast Optical Interrogation", Comment in Nature Apr. 5, 2007; 446 (7136):617-9, Abstract, (1pp.).
Marleny Elizabeth Marquez Martinez et al., "Effect of IR Laser Photobiomodulation on the Repair of Bone Defect Grafted with Organic Bovine Bone", Journal Lasers in Medical Science, Springerlink Date, Thursday, Sep. 20, 2007, Abstract, (2pp.).
Yasuyuki Nemota et al., "Inductive and Inhibitory Effects of Light on Cell Division in Chattonella Antiqua", Plant and Cell Physiology, Oxford Journals, vol. 26, No. 4, pp. 669-674, Abstract, downloaded from http://pcp.oxfordournals.org/cgi/content/abstract/26/4/669 on Mar. 26, 2008, (1pp.).
Arany PR. et al., "Activation of Latent TGF-beta1 by Low-Power Laser in Vitro Correlates with Increased TGF-beta 1 Levels in Laser-enhanced Oral Wound Healing", Wound Repair Regen, Nov.-Dec. 2007;15(6):866-74, Abstract, (1pp.).
Lopes CB. et al., "Infrared Laser Photoblomodulation (lambda 830 nm) on Bone Tissue Around Dental Implants: a Raman Spectroscopy and Scanning Electronic Microscopy Study in Rabbits", Photomed Laser Surg. Apr. 2007, 25(2):96-101, Abstract, (1pp.).
Kim KH, et al., "Laser Lipolysis Using a Novel 1,064nm Nd:YAG Laser", Dermatol Surg. Feb. 2006; 32(2) :241-48; discussion 247, (1pp.).
Kim HS, et al., "Endovenous Laser Ablation of the Great Saphenous Vein with a 980-nm Diode Laser in Continuous Mode: Early Treatment Failures and Successful Repeat Treatments", Comment in: J. Vasc. lnterv Radiol, Jun. 2007; 18(6):811; Author Reply 812-3, (2pp.).
Heinrich E., et al, "Technique and Short-Term Outcome of Green Light Laser (KTP, 80w) Vaporisation of the Prostate", Eur Urol. Dec. 2007;52 (6):1632-7. Epub Jul. 31, 2007, (1 pp.).
Liu, Timon et al., "Photobiomodulation: Phenomenology and its Mechanism" (c) 2005; SPIE—The International Society for Optical Engineering, Abstract, downloaded from http://adsabs.harvard.edu/abs/2005SPIE.5630..185L on Mar. 26, 2008 (1pp.).
"Viral Inactivation of Blood Products", Transfusion, the Journal of the American Association of Blood Banks, vol. 30, Jul./Aug. 1990, No. 6, (3pp.).
N. Etmnasser et al., "Pulsed-light System as a Novel Food Decontamination Technology: a Review", Can. J. Microbiol., 53, (2007), pp. 813-821, (9pp.).
Parmeswaran Diagaradjane et al., "Modulation of in Vivo Tumor Radiation Response via Gold Nanoshell-Mediated Vascular_Focused Hyperthermia: Characterizing an Integrated Antihypoxic and Localized Vascular Disrupting Targeting Strategy", Nano Letters, 2008, vol. 8, No. 5, 1492-1500, (9PP.).
Marino A. Campo et al., "Polymeric Photosensitizer Prodrugs for Photodynamic Therapy" Photochemistry and Photobiology, 2007, 83, pp. 958-965, (8PP.).
Margaret T. T. Wong-Riley, et al., "Photobiomodulation directly benefits primary neurons functionally inactivated by toxins", The Journal of Biological Chemistry, vol. 280, No. 6, 2005, pp. 4761-4771.
J. T. Eells, et al., "Therapeutic photobiomodulation for methanol-induced retinal toxicity", PNAS, Mar. 18, 2003, vol. 100, No. 6, pp. 3439-3444.

(56) References Cited

OTHER PUBLICATIONS

Yasuyuki Nemota, et al., "Inductive and inhibitory effects of light on cell division in Chattonella antiqua", Plant and Cell Physiology, 1985, vol. 26, No. 4 pp. 669-674. Article.
Arany PR., et al., "Activation of latent TGF-beta1 by low-power laser in vitro correlates with increased TGF-beta1 levels in laser-enhanced oral wound healing", Wound Repair Regen, Nov.-Dec. 2007; 15(6):866-74 (abstract)-AbstractPlus.
Lopes CB., et al., "Infrared laser photobiomodulation (lambda 830 nm) on bone tissue around dental implants: a Raman spectroscopy and scanning electronic microscopy study in rabbits", Photomed Laser Surg., Apr. 2007;25(2): 96-101, (abstract)-AbstractPlus.
Kim KH, et al., "Laser lipolysis using a novel 1,064 nm Nd:YAG Laser" Dermatol Surg, Feb. 2006; 32(2): 241-48; discussion 247, (abstract)-AbstractPlus.
Kim HS, et al., "Endovenous laser ablation of the great saphenous vein with a 980-nm diode laser in continuous mode: early treatment failures and successful repeat treatments", Comments in: J. Vasc. Interv. Radiol. Jun. 2007; 18(6): 811: author reply 812-3, (abstract)-AbstractPlus.
Heinrich E., et al., "Technique and short-term outcome of green light laser (KTP, 80w) vaporization of the prostate", Eur Urol, Dec. 2007; 52(6): 1632-7. Epub Jul. 31, 2007, (abstract)-AbstractPlus.
Liu, Timon C., et al., "Photobiomodulation: phenomenology and its mechanism", SPIE, vol. 5630, (2005), pp. 185-191, Abstract.
Han X et al., "Multiple-color optical activation, silencing, and desynchronization of neural activity, with single-spike temporal resolution", PLoS One, Mar. 21, 2007;2(3):e299, (abstract)-AbstractPlus.
Paul D. Wood et al., "Reactions of Psoralen Radical Cations with Biological Substrates", Photochemistry and Photobiology, Article, pp. 155-162 (Abstract), Bioone Online Journal Access Control, vol. 72, Jun. 2008, http://www.bioone.org/perlserv , 1pp.).
Reynel Cando et al., "High Potency of Indolyl Aryl Sulfone nonnucleoside Inhibitors Towards Drug-Resistant Human Immunodeficiency Virus Type 1 Reverse Transcriptase Mutants Is Due to Selective Targeting of Different Mechanistic Form of the Enzyme", Antimicrobial Agents and Chemotherapy, vol. 49, No. 11, Nov. 2005, pp. 4546-4554 downloaded from aac.asm.org on Oct. 17, 2007, (9pp.).
Jacek Bartkowiak et al.,"Selective Displacement of Nuclear Proteins by Antitumor Drugs Having Affinity for Nucleic Acids", Proc.Natl. Acad.Sci. vol. 86, pp. 5151-5154, Jul. 1989, Medical Sciences, Abstract, (1 pp.).
Sylvie Giacchetti et al., "Phase III Trial Comparing 4-Day Chronomodulated Therapy Versus 2-Day Conventional Delivery of Fluorouracil, Leucovorin, and Oxalipiatin as First-Line Chemotherapy of Metastatic Colorectal Cancer: The European Organisation for Research and Treatment of Cancer Chronotherapy Group", Journal of Clinical Oncology, Original Report, vol. 24, No. 22, Aug. 1, 2008, (8pp.).
Fr G. McConnell, "Visit to Lassie (Apr. 2008): Initiating an International Colaboration to Develop Laser Sources for Spatially-Localised, Deep-Tissue Photostimulation", University of Strathclyde, Centre for Biophotonics, EPSRC Reference: EP/F036213/1, EPDRC, http://gow.epsrc.ac.uk/ViewGrant.aspx?GrantRef=EP/F036213/1 (2pp.).
K. Jensen, J. Weldon, H. Garcia, and A. Zettl, "Nanotube Radio," Nano Lett, vol. 7, No. 11, 3508-3511 (2007).
Douglas D. Young and Alexander Deiters, "Photochemical Hammerhead Ribozyme Activation", Bioorganic & Medicinal Chemistry Letters, 16(10) ,pp. 2658-2661 (2006).
Hirsch, L.R., Stafford , R.J., Bankson, J.A. , Sershen, S.R., Rivera, B., Price, R.E., Hazle, J. D., Halas, N. J., and West, J. L., Nanoshell-. mediated near-infrared thermal therapy of tumors under magnetic resonance guidance. PNAS, 2003. 100(23): p. 13549-13554.
Xiaohua Huang & Prashant K. Jain & Ivan H. El-Sayed & Mostafa A. El-Sayed, Plasmonic photothermal therapy (PPTT) using gold nanoparticles, Lasers in Medical Science, Aug. 2007.

Mircea Cotlet, Tom Vosch, Satoshi Habuchi, Tanja Weil, Klaus Mullen, Johan Hofkens, and Frans De Schryver, "Probing Intra-molecular Forster Resonance Energy Transfer in a Naphthaleneimide-Peiyleneimide-Terrylenediimide-Based Dendrimer by Ensemble and Single-Molecule Fluorescence Spectroscopy", J. Am. Chem. Soc. 2005, 127, 9760-9768.
M.O. Guler, "Singlet-Singlet and Triplet-Triplet Energy Transfer in Bichromophoric Cyclic Peptides," Worcester Polytechnic Institute, May 18, 2002.
Young and Deiters in "Photochemical Control of Biological Processes", Org. Biomol. Chem., 5, pp. 999-1005 (2007).
T. Vo-Dinh, M.Y.K. Hiromoto, G. M. Begun and R. L. Moody, "Surface-enhanced Raman spectroscopy for trace organic analysis," Anal. Chem., vol. 56, 1667, 1984.
M. M. Kerker, Electromagnetic Model for Surface-Enhanced Raman Scattering (SERS) on Metal Colloids, Acc. Chem. Res., 17, 370 (1984).
T. Vo-Dinh, "Surface-Enhanced Raman Spectroscopy Using Metallic Nanostructures," Trends in Anal. Chem., 17,557 (1998).
J. B. Jackson, S. L. Westcott, L. R. Hirsch, J. L. West and N. H. Halas, "Controlling the surface enhanced Raman effect via the nanoshell geometry," Appl. Phys. Lett., vol. 82, 257-259, 2003.
S. J. Norton and T. Vo-Dinh, "Plasmonic Resonances of nanoshells of Spheroidal Shape", IEEE Trans. Nanotechnology, 6, 627-638 (2007).
R. Elghanian, J.J. Storhoff, R.C. Mucic, R.L. Letsinger and C.A. Mirkin, Selective colorimetric detection of polynucleotides based on the distance-dependent optical properties of gold nanoparticles. Science 277 (1997), pp. 1078-1081.
Z. Li, R.C. Jin, C.A. Mirkin and R.L. Letsinger, Multiple thiol-anchor capped DNA-gold nanoparticle conjugates. Nucleic Acids Res. 30 (2002), pp. 1558-1562.
Y.W. Cao, R. Jin and C.A. Mirkin, DNA-modified core-shell Ag/Au nanoparticles. J. Am. Chem. Soc. 123 (2001), pp. 7961-7962.
Burgess, J. D.; Hawkridge, F. M., "Octadecyl Mercaptan Sub-monolayers on Silver Electrodeposited on Gold Quartz Crystal Microbalance Electrodes", Langmuir 1997, 13, 3781-6.
Hainfeld et al, Gold nanoparticles: a new X-ray contrast agent, The British Journal of radiology, 79, 248, 2006.
Ma et al, DNA-Passivated CdS Nanocrystals : Luminescence, Bioimaging, and Toxicity Profiles, Langmuir, 23 (26), 12783-12787 (2007).
Hua et al, Soft x-ray excited optical luminescence : Some recent applications, Rev. Sci. Instrum. ,, 73, 1379, 2002.
Jaegle et al, Ultraviolet luminescence of CsI and CsCl excited by soft x-ray laser, J. Appl. Phys., 81, 2406, 1997.
Kun Chen, Yang Liu, Guillermo Ameer, Vadim Backman, Optimal design of structured nanospheres for ultrasharp light-scattering resonances as molecular imaging multilabels, Journal of Biomedical Optics, 10(2), 024005 (Mar./Apr. 2005).
Mirkhin et al, X-ray excited luminescence of some molybdates, Nuclear Instrum. Meth. In Physics Res. A, 486, 295 (2002).
L. Soderholm, G. K. Liu, Mark R. Antonioc, F. W. Lytle, X-ray excited optical luminescence .XEOL. detection of x-ray absorption fine structure .XAFZ, J. Chem. Phys,109, 6745, 1998.
Masashi Ishiia, Yoshihito Tanaka and Tetsuya Ishikawa, Shuji Komuro and Takitaro Morikawa, Yoshinobu Aoyagi, Site-selective x-ray absorption fine structure analysis of an optically active center in Er-doped semiconductor thin film using x-ray-excited optical luminescence, Appl. Phys. Lett, 78, 183, Jan. 8, 2001.
Kuiru Li, Mark I. Stockman, and David J. Bergman, Self-Similar Chain of Metal Nanospheres as an Efficient Nanolens, Physical Review Letter, vol. 91, No. 22, 227402-1, 2003.
Frens, G., Controlled nucleation for the regulation of the particle size in monodisperse gold solutions. Nature (London) Phys Sci 1973. 241: p. 20-22.
Lei Zhang, Joe Swift, Christopher A. Butts, Vijay Yerubandi and Ivan J. Dmochowski, Structure and activity of apoferritin-stabilized gold nanoparticles, Journal of Inorganic Biochemistry, vol. 101, 1719-1729, 2007.
Keiko Yoshizawa, Kenji Iwahori, Kenji Sugimoto and Ichiro Yamashita, Fabrication of Gold Sulfide Nanoparticles Using the Protein Cage of Apoferritin, Chemistry Letters, vol. 35 (2006), No. 10 p. 1192.

(56) References Cited

OTHER PUBLICATIONS

Martin Nikl, Scintillation detectors for x-rays, *Meas. Sci. Technol.* 17 (2006) R37-R54.

Kadshchuk, A. K., Ostapenko, N. I., Skryshevskii, Yu. A., Sugakov, V. I. and Susokolova, T. O., Clusters of Dipole Charge-Carrier Capture Centers in Organic Crystals, *Mol. Cryst. and Liq. Cryst.*, 201, 167 (1991) t.

S. V. Izvekov, V. I. Sugakov, Exciton and Electron Traps on Structural Defects in Molecular Crystals with Dipolar Molecules, *Physica Scripta.* vol. T66, 255-257, 1996.

A. P. D'Silva, G. J. Oestreich, and V. A. Fassel, X-ray excited optical luminescence of polynuclear aromatic hydrocarbons, *Anal. Chem.*; 1976; 48(6) pp. 915-917.

T. Vo-Dinh, Multicomponent analysis by synchronous luminescence spectrometry, *Anal. Chem.*; 1978; 50(3) pp. 396-401.

J. Bellessa, C. Bonnand, and J. C. Plenet, J. Mugnier, Strong Coupling between Surface Plasmons and Excitons in an Organic Semiconductor, *Phys. Rev. Lett*, 93 (3), 036404-1, 2004.

Alexander O. Govorov, Garnett W. Bryant,‡ Wei Zhang, Timur Skeini, Jaebeom Lee,§ Nicholas A. Kotov, Joseph M. Slocik,| and Rajesh R. Naik, Exciton-Plasmon Interaction and Hybrid Excitons in Semiconductor-Metal Nanoparticle Assemblies, *Nano Lett.*, vol. 6, No. 5, 984, 2006.

I.V. Bondarev, K. Tatur and L.M. Woods, Strong excitor plasmon coupling in semiconducting carbon nanotube, Jul. 8, 2009 Accepted paper in Physical Review B.

Yuri Fedutik, Vasily Temnov, Ulrike Woggon, Elena Ustinovich, and Mikhail Artemyev , Exciton-Plasmon Interaction in a Composite Metal-Insulator-Semiconductor Nanowire System, *J. . Am. Chem. Soc.*, 129 (48), 14939-14945, 2007.

G.W. Ford and W. H. Weber, Electromagnetic interactions of molecules with metal surfaces, *Phys. Rep.* 113, 195-287 (1984).

Gregory A. Wurtz, Paul R. Evans, William Hendren, Ronald Atkinson, Wayne Dickson, Robert J. Pollard, and Anatoly V. Zayats, Molecular Plasmonics with Tunable Exciton-Plasmon Coupling Strength in J-Aggregate Hybridized Au Nanorod Assemblies, *Nano Lett.*, vol. 7, No. 5, 1297, 2007.

Jaebeom Lee, Alexander O. Govorov, John Dulka, and Nicholas A. Kotov, Bioconjugates of CdTe Nanowires and Au Nanoparticles: Plasmon-Exciton Interactions, Luminescence Enhancement, and Collective Effects, *Nano Lett.*, vol. 4, No. 12, 2323, 2004.

N.R. Jana, L. Gearheart and C.J. Murphy, Seeding growth for size control of 5-40 nm diameter gold nanoparticles. *Langmuir* 17 (2001), pp. 6782-6786.

Brust, M.; Walker, M.; Bethell, D.; Schiffrin, D. J.; Whyman, R., Synthesis of Thiol-derivatised Gold Nanoparticles in a Two-phase Liquid-Liquid System *Chem. Commun.* 1994, 801.

Hostetler, M.J.; Wingate, J. E.; Zhong, C. J.; Harris, J. E.; Vachet, R. W.; Clark, M, R.; Londono, J. D.; Green, S. J.; Stokes, J. J.; Wignall, G. D.; Glish, G. L.; Porter, M. D.; Evans, N. D.; Murray, R. W., Alkanethiolate Gold Cluster Molecules with Core Diameters from 1.5 to 5.2 nm: Core and Monolayer Properties as a Function of Core Size, *Langmuir* 1998, 14, 17.

Schmid, G.; Pfeil, R.; Boese, R.; Bandrmann, F.; Meyer, S.; Calis, G. H. M.; van der Velden, J. W. A., $Au_{55}[P(C_6H_5)_3]_{12}Cl_6$- ein Goldcluster ungewohnlicher Größe, *Chem. Ber.* 1981, 114, 3634; with English Abstract.

Warner, M. G.; Reed, S. M.; Hutchison, J. E., Small, Water-Soluble, Ligand-Stabilized Gold Nanoparticles Synthesized by Interfacial Ligand Exchange Reactions, *Chem. Mater.* 2000,12, 3316.

Weare, W. W.; Reed, S. M.; Warner, M. G.; Hutchison, J. E., Improved Synthesis of Small (d $_{CORE}$ ≈1.5 nm) Phosphine-Stabilized Gold Nanoparticles, *J. Am. Chem. Soc.* 2000, 122, 12890.

Ziyi Zhong, Benoit Male, Keith B. Luong, John H.T., More Recent Progress in the Preparation of Au Nanostructures, Properties, and Applications, *Analytical Letters*; 2003, vol. 36 Issue 15, p. 3097-3118.

Akito Masuhara, Satoshi Ohhashi, Hitoshi Kasai; Shuji Okada, Fabrication and Optical Properties of Nanocomplexes Composed of Metal Nanoparticles and Organic Dyes, *Journal of Nonlinear Optical Physics & Materials* vol. 13, Nos. 3 & 4 (2004) 587-592.

Wang et al. in "Electromagnetic excitation of nano-carbon in vacuum," in Optics Express, vol. 13, No. 10, May 10, 2005.

Aslan et al. in "Multicolor Microwave-Triggered Metal-Enhanced Chemiluminescence," in J. Am. Chem. Soc. published on Web Sep. 23, 2006.

M. A. Correa-Duarte, M. Giesig, and L. M. Liz-Marzan, Stabilization of CdS semiconductor nanoparticles against photodegradation by a silica coating procedure, Chem. Phys. Lett., 1998, 286: 497.

M. Thorns, H. von Seggern, Method for the determination of photostimulable defect center concentrations, production rates, and effective formation energies, J. Appl. Phys. 1994, 75: 4658-4661.

W. Chen, S. P. Wang, S. Westcott, J. Zhang, A. G. Joly, and D. E. McCready, Structure and luminescence of $BaFBr:Eu_{2+}$ and $BaFBr:Eu^{2+}$, $Tb^{3+}$ phosphors phosphors and thin films, J. Appl. Phys. 2005, 97: 083506.

Mai Thu Thi Tran, Mohammed Farid, "Ultraviolet Treatment of Orange Juice" published in Innovative Food Science & Emerging Technologies (vol. 5, Issue 4, Dec. 2004, pp. 495-502).

Santos et al, Photocatalysis as a Tertiary Treatment for Petroleum Refinery Wastewaters, Braz. J. Chem. Eng. vol. 23, No. 4, 2006.

Spatio-Resolved Hyperbranched Graft Polymerized Surfaces by Iniferter-Based Photograft Copolymerization, *Langmuir*, 2002, 18 (7), pp. 2601-2606.

Pettinger B., U. Wenneng, and H. Wetzel, Surface-plasmon enhanced Raman-scattering Frequency and Angular Resonance of Raman Scattered Light From Pyridine on Au, Ag and Cu Electrodes, 1980, Surf, Sci., 101, 409.

Fleishman M., P. R. Graves, and J. Robinson, The Raman-Spectroscopy of the Ferricyanide/Ferrocyanide System at Gold, β-Palladium Hydride and Platinum Electrodes, 1985, L Electroanal. Chem., 182, 87.

Miller S. K., A. Baiker, M. Meier, and A. Wokaun, Surface-enhanced Raman scattering and the preparation of copper substrates for catalytic studies, 1984, J. Chem. Soc. Farad. Trans. I, 80, 1305.

Taranenko N., J.P. Alarie, D.L. Stokes, and T. Vo Dinh, Surface-Enhanced Raman Detection of Nerve Agent Simulant (DMMP and DIMP) Vapor on Electrochemically Prepared Silver Oxide Substrates, 1996, J. Raman Spectr., 27, 379-384.

Jennings C., R. Aroca, A. M. Hor, and R. O. Loutfy, Surface-enhanced Raman scattering from copper and zinc phthalocyanine complexes by silver and indium island films, 1984, Anal. Chem., 56, 203.

Ni F., R. Sheng, and T. M. Cotton, Flow-injection analysis and real-time Detection of RNA bases by surface-enhanced Raman-spectroscopy, 1990, Anal. Chem., 62, 1958.

Moody R. L., T. Vo Dinh, and W. H. Fletcher, Investigation of Experimental Parameters for Surface-Enhanced Raman Scattering (SERS) Using Silver-Coated Microsphere Substrates, 1987, Appl. Spectr., 41, 966.

Bello J. M., D. L. Stokes and T. Vo Dinh, Silver-Coated Alumina as a New Medium for Surface-Enhanced Raman Scattering Analysis, 1989, Appl. Spectrosc., 43. 1325.

Sutherland, A Portable Surface-Enhanced Raman Spectrometer, Instrumentation Science & Technology, vol. 22, Issue 3 Aug. 1994, pp. 231-239.

Alak A., and T. Vo Dinh, Silver-Coated Fumed Silica as New Substrate Materials for Surface-Enhanced Raman Scattering, 1989, Anal. Chem., 61, 656.

Liao P. F., and M. B. Stem, Surface-enhanced Raman scattering on gold and aluminum particle arrays, 1982, Opt. Lett., 7, 483.

Vo Dinh T., M. Meier, and A. Wokaun, 1986, Surface Enhanced Raman Spectroscopy with Silver Particles on Stochastic Post Substrates, Anal. Chim. Acta, 181, 139.

Enlow P. D., M. C. Buncick, R. J. Warmack, and T. Vo Dinh, Detection of Nitro polynuclear Aromatic Compounds by Surface Enhanced Raman Spectroscopy, 1986, Anal. Chem., 58, 1119.

Vo Dinh T., 1989, Surface-Enhanced Raman Spectrometry, in Chemical Analysis of Polycyclic Aromatic Compounds, Wiley, T. Vo-Dinh, Ed., New York.

(56) References Cited

OTHER PUBLICATIONS

M. Volkan, D.L. Stokes and T. Vo-Dinh, A Sol-Gel Derived AgCl Photochromic Coating on Glass for SERS Chemical Sensor Application, Sensors and Actuators B, 106, 660-667 (2004).
Canadian Office Action dated Apr. 7, 2017 in Patent Application No. 2,720,513.
Canadian Office Action dated Jul. 26, 2016 in Patent Application No. 2,906,990.
Office Action dated Aug. 14, 2017 in European Patent Application No. 09 726 873.4.
BBC News /Health, one minute world news, "Nano device times drug release", http://news.bbc.co.uk/2hl/health/7808672.stm retrieved from internet May 12, 2009 (3 pp.).
Joshua E. Collins, et al., "Infrared light utilized for photodynamic therapy by activation of rare earth phosphors for visible light generation", Proc. of SPIE, 2007, vol. 6427, 642717-1 to 642717-12.
EVLT-Non-Surgical Varicose Vein Treatment, website article, www.riaivision.com/invision/patientinfo/intervrad/evlt_varicose_vein_treatment.asp retrieved from internet Mar. 26, 2008.
Maria Kyriazi, et al., "Topical photodynamic therapy of murine non-melanoma skin carcinomas with aluminum phthalocyanine chloride and a diode laser: pharmacokinetics, tumor response and cosmetic outcomes", Photodermatology, Photoimmunology & Photomedicine, 2008, vol. 24, pp. 87-94.
Lie Lin, et al., "Distribution and photobleaching of photosensitizer chlorophyll derivative (DPD) in SMCF7 cancer cells". Proc. of SPIE 2007, vol. 6534. 65342G-1 to 65342G-6.
Loctite, Light Cure, Technology, Loctite Americas 2000, Technical Manual, (24 pages).
Mermut et al., "Time-resolved luminescence measurements of the magnetic field effect on paramagnetic photosensitizers in photodynamic reactions", Proc. of SPIE, 2008, vol. 6845, 68450T-1 to 68450T8.
Photostimulation, from Wikipedia. http://en.wikipedia.org/wiki/Photostimulation retrieved from internet Mar. 4, 2008 (1 p.).
Harry Whelan, et al., "Harnessing the cell's own ability to repair and prevent neurodegenerative disease", SPIE, Newsroom, 2008, 10.1117/2.1200802.1014, 3 pp.
Palmer H. White M. D. , "Smartlipo & LaserBodySculting", Laser Light Treatment Center, http://www.laserlight.org/lipo.htm retrieved from internet Mar. 26, 2008 (2 pp.).
Qingdong Zheng, et al., "Water-soluble two-photon absorbing nitrosyl complex for light-activated therapy through nitric oxide release", Molecular Pharmaceutics, 2008, vol. 5, No. 3, pp. 389-398.
Office Action dated Jan. 1, 2018 in Saudi Patent Application No. 114350274.
Smith, D.M., 2013 Hard X-ray and y-ray detectors,In: Huber, MCE, Observing Photons in Space. ISSI Scientific Report Series, vol. 9, Springer, NY, NY, (18 pages).
AMCRYS Scintillation Materials Data Sheet, Sep. 2009 (5 pages).
Rajan et al, "X-ray excited optical luminescence studies on the bystme BAXY (X,Y=F, Cl, Br, I)", Pramana—journal of physics, 2005, vol. 65, No. 2, pp. 323-338.
Chandrasekhar et al, "Steady-state absorption and fluorescence study: Dipole moments of coumarins", Indian Journal of Pure & Applied Physics, 2006, vol. 44, pp. 292-299.
Yeargers et al, "Absorption and emission spectra of psoralen and 8-methoxy-psoralen in powders and in solutions", The Journal of Investigavtie Dermatologyl, 1965, vol. 44, No. 3 , pp. 181-188.
Nikl, "Scintillation detectors for x-rays", Meas. Sci. Technol., 2006, vol. 17 pp. R37-R54.
Rochkind et al, "Transplantation of embryonal spinal cord nerve cells cultured on biodegradable microcarriers followed by low power laser irradiation for the treatment of traumatic paraplegia in rats", Neurol Res., 2002, vol. 24, No. 4 Abstract only (2 pages).
Rochkind et al, "Development of a tissue-engineered composite implant for treating traumatic paraplegia in rats", Eur. Spine J., 2006 vol. 15, pp. 234-245.
Rochkind, "Laser Phototherapy: A new Modality for Nerve Cell Tissue Engineering Technology, Cell Therapy and Nerve Repair",
Presentation at the 2008—International Conference of the World Association of Laser Therapy (9 pages).
Karu et al, "A Novel Mitochondrial signaling Pathway Activated by Visible-to-near Infrared Radiation", Photochemistry and Photobiology, 2004, vol. 80, pp. 366-372.
Karu, "Cellular mechanisms of Low Power Laser Therapy: New Questions", Chapter IV, Lasers Med. Dent, 2003, pp. 79-100.
Karu, 2002, "Low Power Laser Therapy" in CRC Biomedical Photonics Handbook, T. Vo-Dihn, Editor-in-Chief, CRC Press, Boca Raton, USA (25 pages).
Office Action dated Oct. 10, 2018, in Pakistani patent application No. 282/2009 (2 pages).
Office Action dated Sep. 21, 2018, in Japanese patent application No. 2017-235146 (with English translation) (12 pages).
Third Office Action dated Nov. 6, 2018, in Chinese patent application No. 201510641152.4 (with English translation) (22 pages).
Extended European Search Report dated Mar. 5, 2018 in Patent Application No. 17197468.6.
Communication pursuant to Rule 69 EPC dated Apr. 9, 2018 in European Patent Application No. 17197468.6.
Khaing Oo, et al., "5-aminolevulinic acid-conjugated gold nanoparticles for photodynamic therapy of cancer", Nanomedi, vol. 3, No. 6, XP008142354, 2008, pp. 777-786.
Second Office Action dated May 22, 2018, in Chinese patent application No. 201510641152.4 (w/ English translation)—24 pages.
Combined Taiwanese Office Action and Search Report dated Dec. 14, 2018 in Patent Application No. 106139211 (with English language translation of Search Report).
A.A. Krasnovsky, Jr., et al., "Activation of Molecular Oxygen by Infrared Laser Radiation in Pigment-Free Aerobic Systems", Biochemistry (Moscow), vol. 68, No. 9, 2003, 4 pages.
European Office Action dated Feb. 19, 2019 in Patent Application No. 17 197 468.6, 6 pages.
Canadian Office Action dated Nov. 21, 2018 in Patent Application No. 2,906,990, citing documents AA, AB and AE—AU therein, 10 pages.
Wesley M. Shraman, et al., "Photodynamic Therapeutics: Basic Principles and Clinical Applications" Drug Discovery Today, vol. 4, No. 11, Nov. 1999, pp. 507-517.
M. Ochsner, "Photophysical and Photobiological Processes in the Photodynamic Therapy of Tumours" Journal of Photochemistry and Photobiology B: Biology, vol. 39, 1997, pp. 1-18.
P. Wardman, "Chemical Radiosensitizers for Use in Radiotherapy" Clinical Oncology, vol. 19, No. 6, 2007, pp. 397-417.
Aaron C. Spalding, et al., "New and Emerging Radiosensitizers and Radioprotectors" Cancer Investigation, vol. 24, No. 4, 2006, pp. 444-456 and cover page.
Masahide Kuroki, et al., "Sonodynamic Therapy of Cancer Using Novel Sonosensitizers" Anticancer Research, vol. 27, 2007, pp. 3673-3677.
Robert B. Campbell, "Battling Tumors with Magnetic Nanotherapeutics and Hyperthermia: Turning up the Heat" Nanomedicine, vol. 2, No. 5, 2007, pp. 649-652.
Dev K. Chatterjee, et al., "Upconverting Nanoparticles as Nanotransducers for Photodynamic Therapy in Cancer Cells" Nanomedicine, Jan. 2008, vol. 3, No. 1, pp. 73-82.
Rolf F. Barth, "A Critical Assessment of Boron Neutron Capture Therapy: an Overview" Journal Neuro-Oncology, vol. 62, 2003, pp. 1-5.
R. Gahbauer, et al., "Boron Neutron Capture Therapy: Principles and Potential" Recent Results Cancer Res., vol. 150, 1998, pp. 183-209.
Minesh P. Mehta, et al., "Radiotherapy for Brain Tumors" Current Oncology Reports, vol. 2, 2000, pp. 438-444.
Martin Weinmann, et al., "Hypoxic Radiosensitizers and Hypoxic Cytotoxins in Radiation Oncology" Curr. Med., Chem. Anti-Cancer Agents, vol. 3, No. 5, 2003, pp. 364-374.
R. Laptev, et al., "Intracellular Chemiluminescence Activates Targeted Photodynamic Destruction of Leukaemic Cells" British Journal of Cancer, vol. 95, 2006, pp. 189-196.
Theodossis Theodossiou, et al., "Firefly Luciferin-Activated Rose Bengal: In Vitro Photodynamic Therapy by Intracellular

(56) References Cited

OTHER PUBLICATIONS

Chemiluminescence in Transgenic NIH 3T3 Cells" Cancer Research, vol. 63, Apr. 15, 2003, pp. 1818-1821 and cover letter.

Yongxia Zhang, et al., "Plasmonic Engineering of Singlet Oxygen Generation" PNAS, vol. 105, No. 6, Feb. 12, 2008, pp. 1798-1802.

Yongxia Zhang, et al., "Metal-Enhanced Singlet Oxygen Generation: A Consequence of Plasmon Enhanced Triplet Yields" J. Fluoresc., Springer, vol. 17, No. 4, 2007, pp. 345-349.

Anna C. S. Samia, et al., "Quantum Dot-Based Energy Transfer: Perspectives and Potential for Applications in Photodynamic Therapy" Photochemistry and Photobiology, vol. 82, 2006, pp. 617-625.

Jarod C. Finlay, "PDT Driven by Energy-Converting Materials: A Theoretical Analysis" Proc. SPIE 7164, Optical Methods for Tumor Treatment and Detection: Mechanisms and Techniques in Photodynamic Therapy, vol. 7164, Feb. 2009, 71640Y-1-71640Y-7 and cover page.

Office Action dated May 5, 2019, in Chinese Patent Application No. 201510641152, filed Apr. 2, 2009 w/English translation.

\* cited by examiner

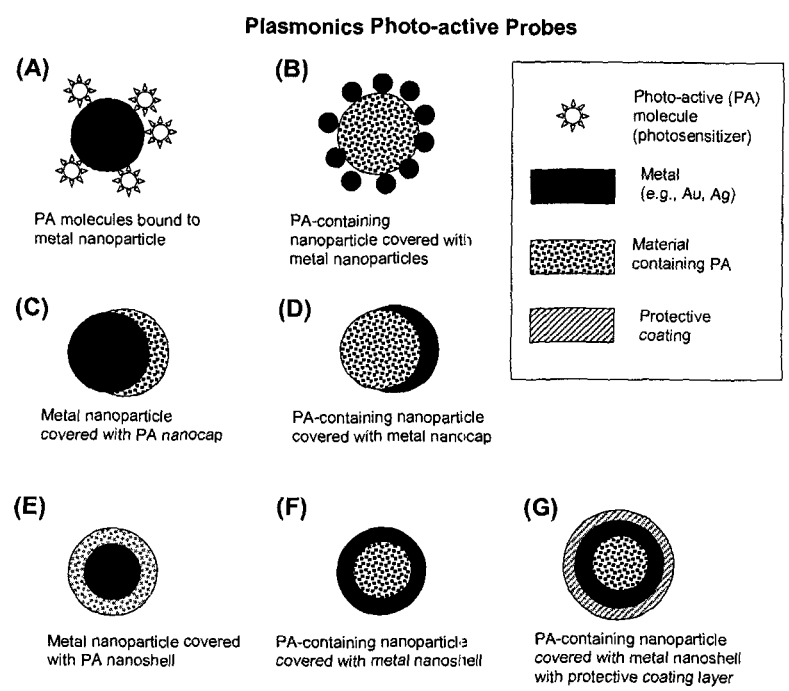
*Figure 7. Plasmonics Photo-active Probes*

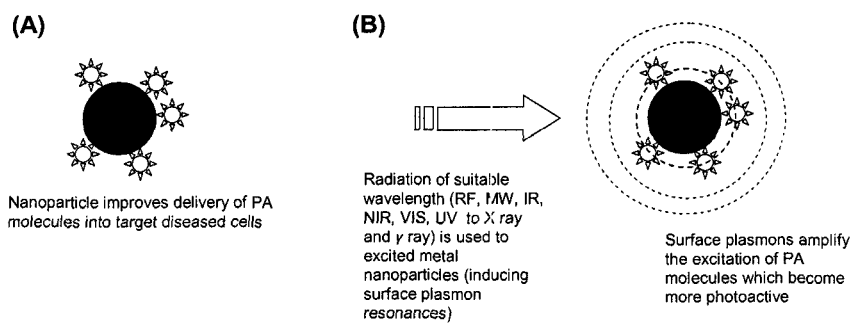
Figure 8. Plasmonics-Enhanced Effect of Photospectral Therapy

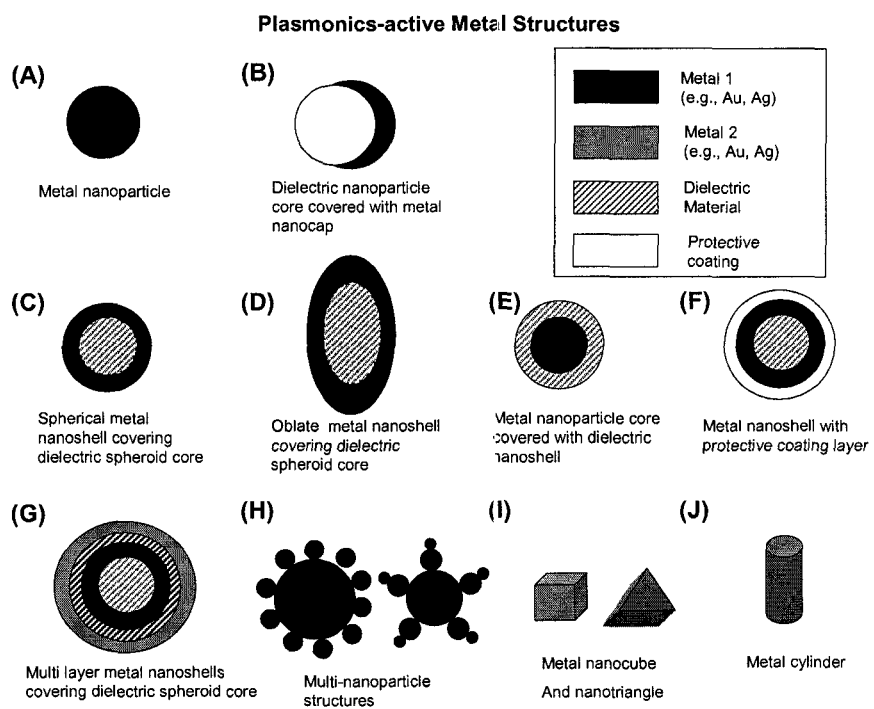
*Figure 9. Plasmonics-active Nanostructures*

Figure 11. PEPST Probe with Various Linkers for Remote Drug Release

*Figure 12. Plasmonics Photo-active Probes with Bioreceptors*

- *Figure 13*: The "therapeutic window" in tissue and absorption spectra of biological components.
- (Source: T. Vo-Dinh, Biomedical Photonics Handbook, CRC, 2003)

*Figure 16*. Gold complexes Exhibiting XEOL
[Taken from : Kim et al, Inorg. Chem., 46, 949, 2007].

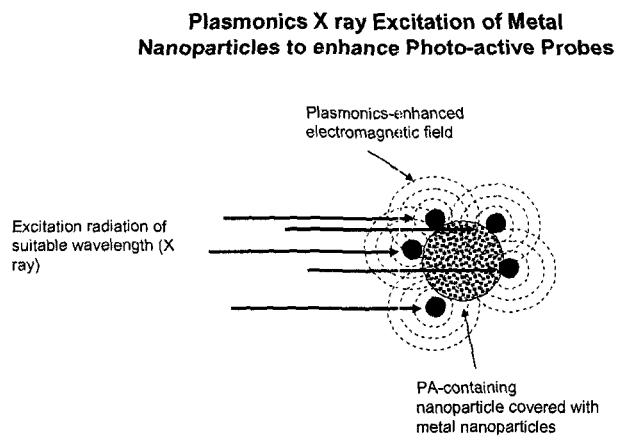
Figure 18. *Plasmonics-Enhanced Mechanism for a Photo-active energy modulation agent-PA Probe*

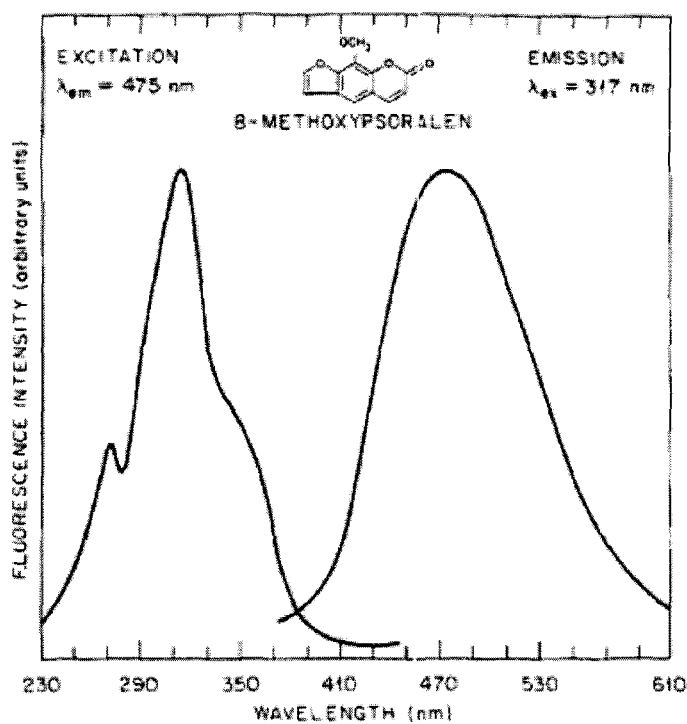
*Figure 19.* Excitation and Emission Fluorescence Spectra of Psoralens
[Source: T. Vo-Dinh et al, J. Agric. Food Chem., 36, 335 (1988)]

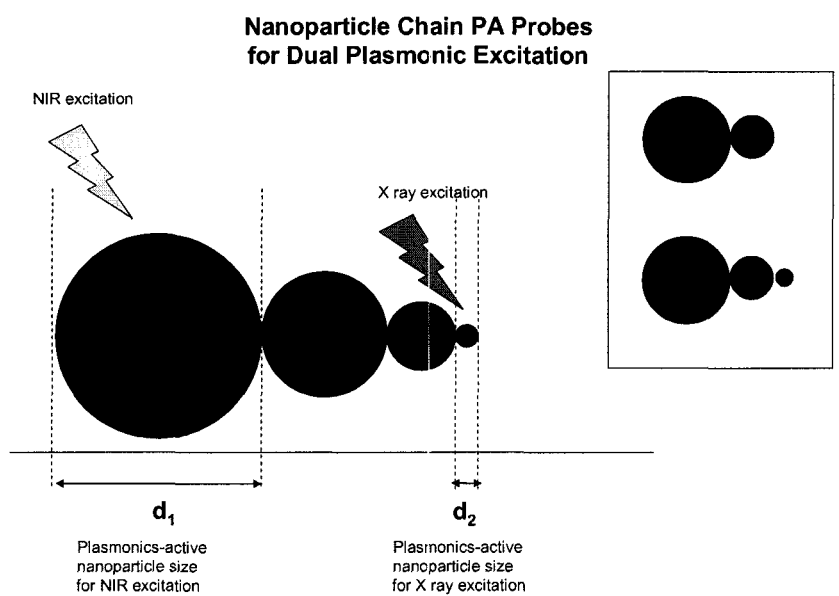
*Figure 21. PEPST Probes for Dual Plasmonic Excitation*

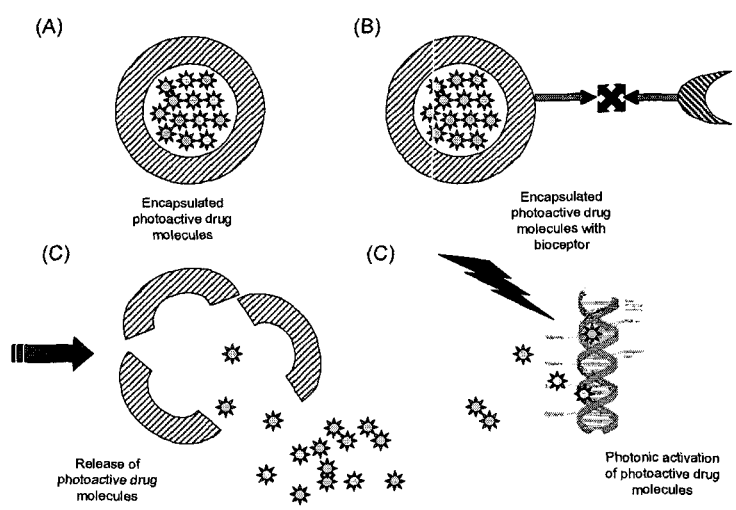
*Figure 22.* Use of Encapsulated Photoactive Agents

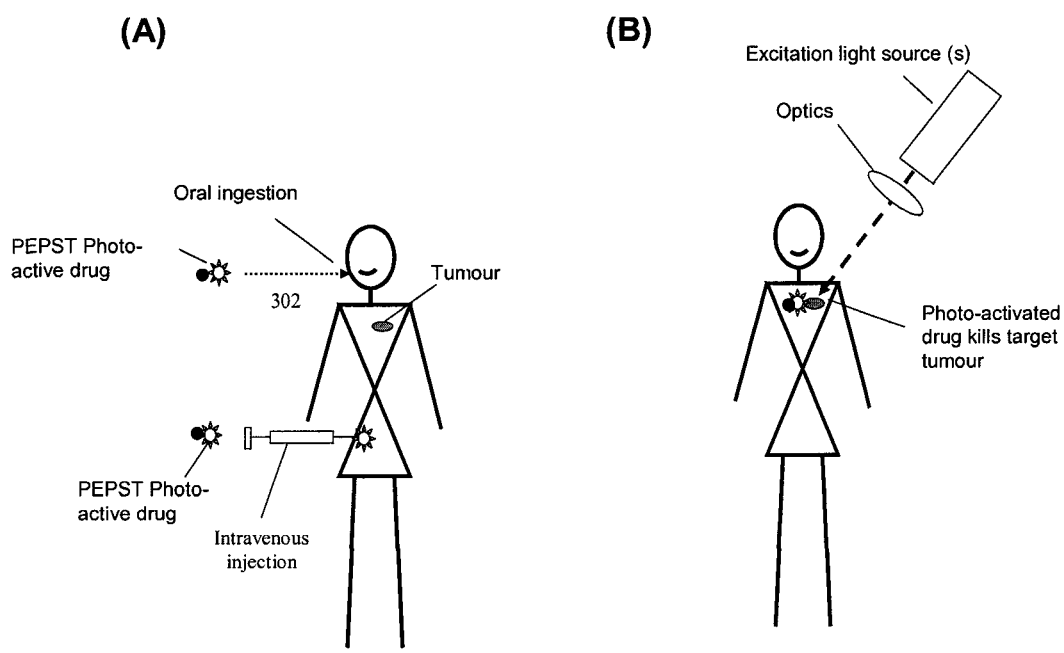
*Figure 23. Principle of Non-Invasive PEPST Modality*

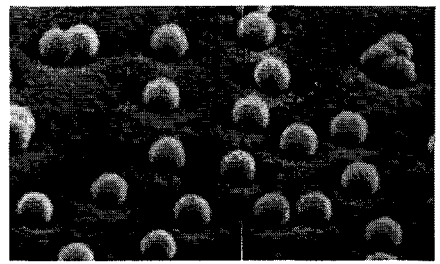
*Figure 24.* Nanocaps (half-nanoshells) comprising polystyrene nanospheres coated with silver

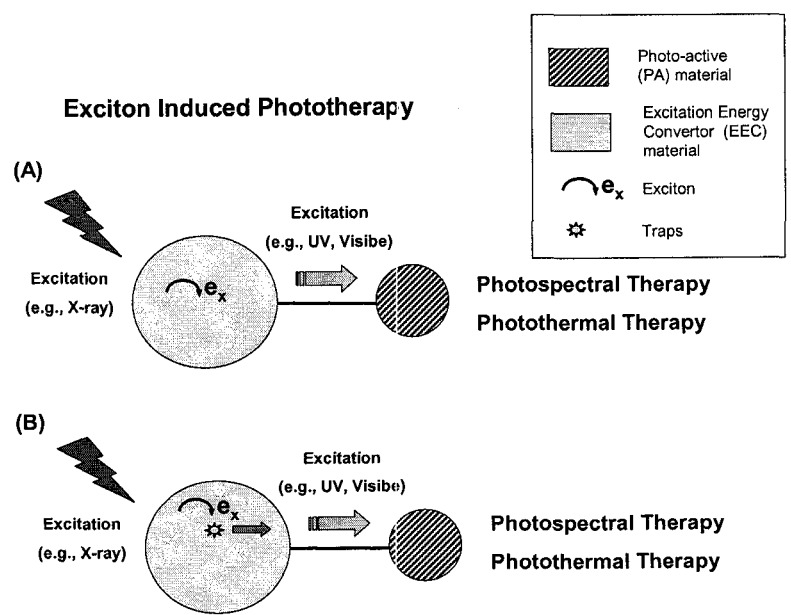
*Figure 25. Schematic Embodiments of Basic EIP Probes*

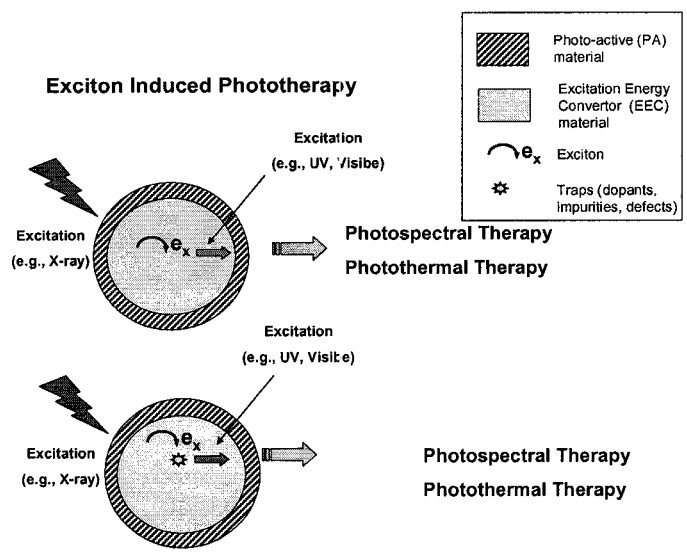
*Figure 28. Schematic Designs of EIP Probes*

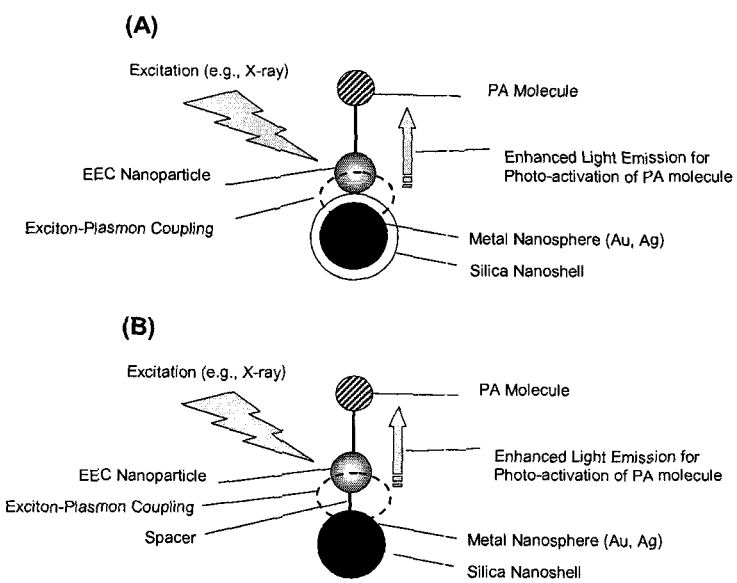
Figure 29. Embodiments of Basic EPEP Probes

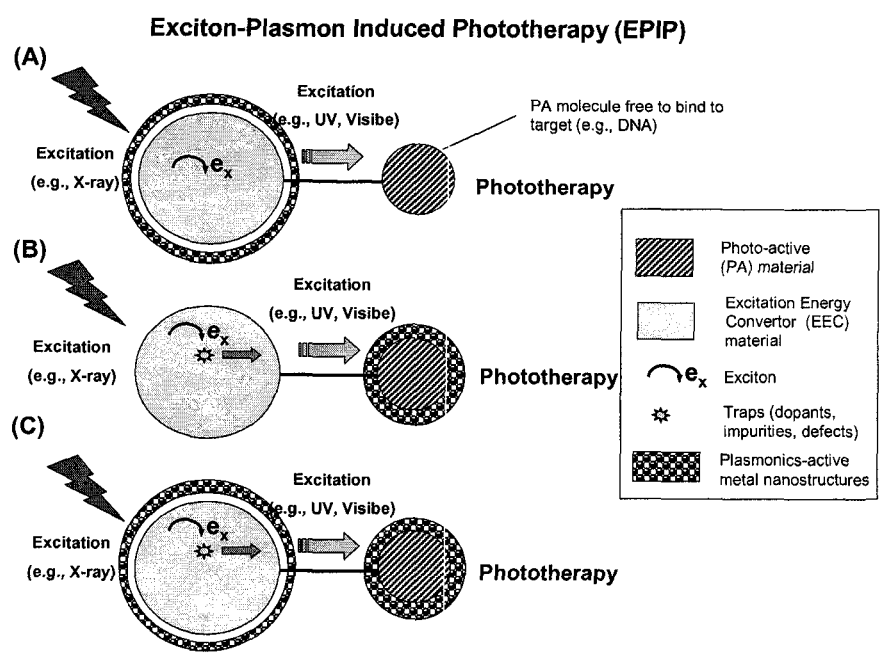
*Figure 30. Embodiments of EPEP Probes*

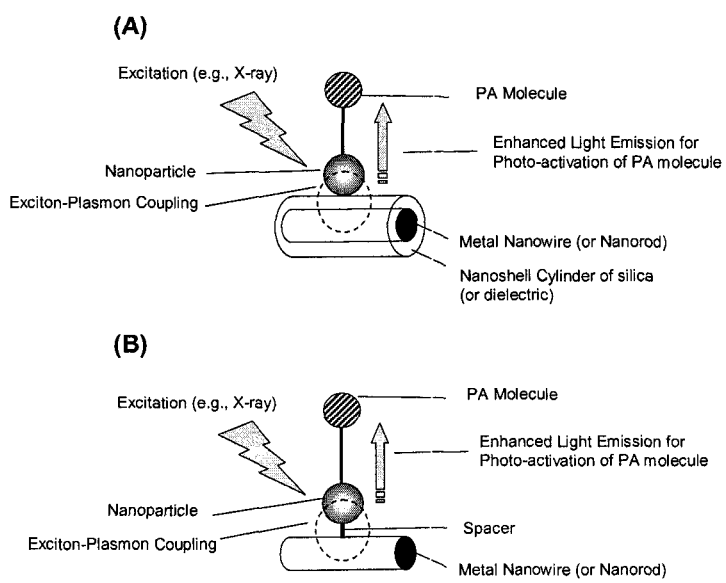
Figure 31. Embodiments of EPEP Probes Having NPs, NWs and NRs

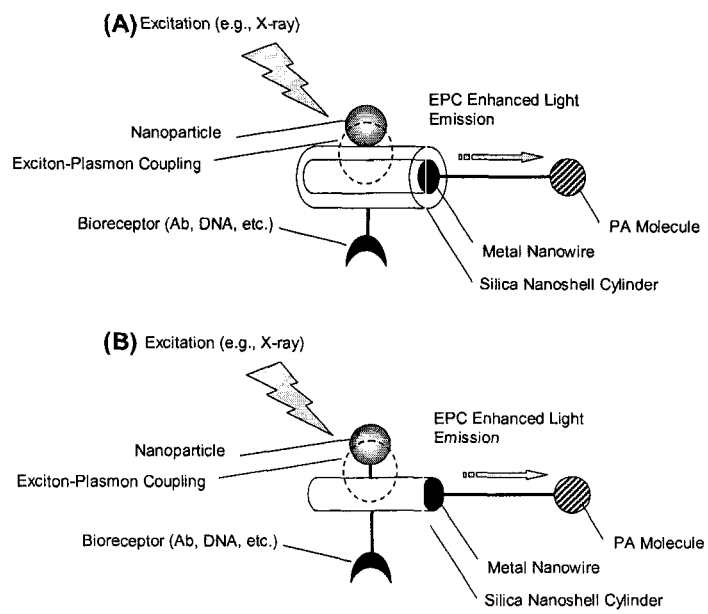
*Figure 32.* Embodiments of EPEP Probes Having NPs, NWs, NRs and Bioreceptors

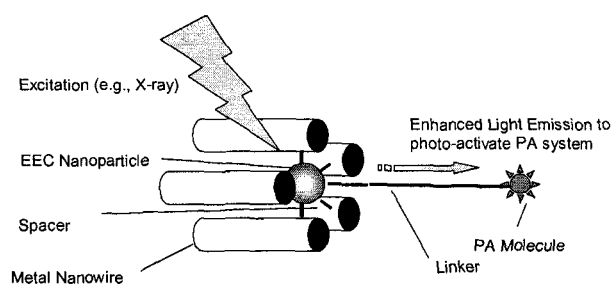
*Figure 33. Embodiment of EPEP Probes Having NPs and multiple NWs*

FIG. 34A 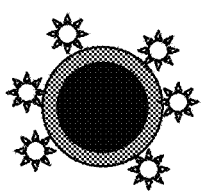 FIG. 34B 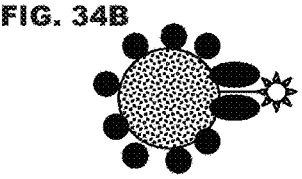
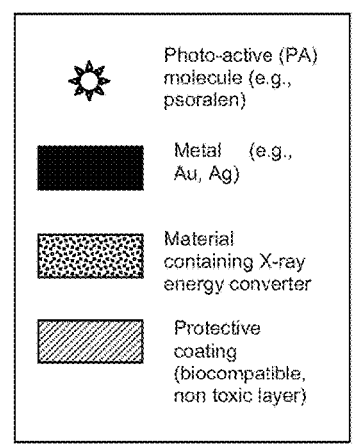
FIG. 34C 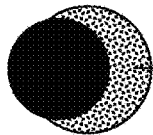 FIG. 34D 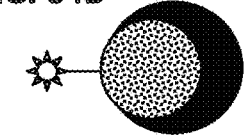
FIG. 34E 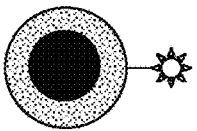 FIG. 34F  FIG. 34G 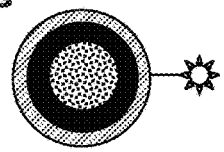

FIG. 35A 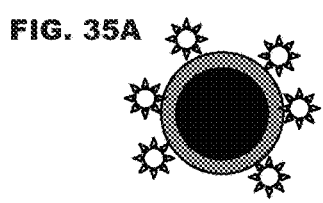 FIG. 35B 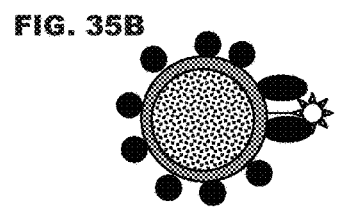
FIG. 35C 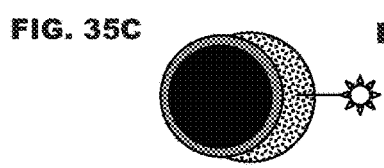 FIG. 35D 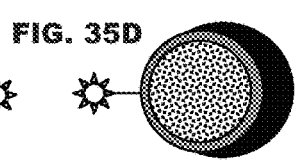
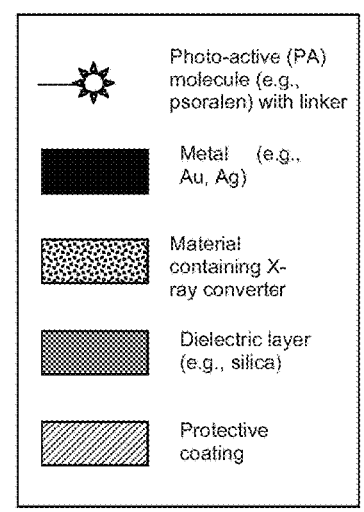
FIG. 35E 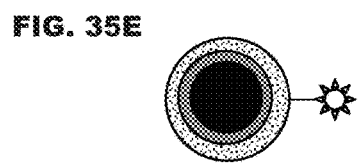 FIG. 35F 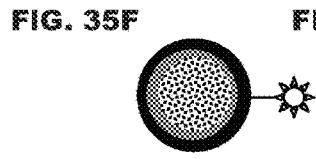 FIG. 35G 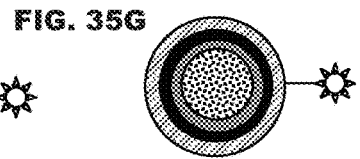

NON-INVASIVE SYSTEMS AND METHODS FOR IN-SITU PHOTOBIOMODULATION

CROSS REFERENCE TO RELATED APPLICATIONS

This application is a continuation of U.S. patent application Ser. No. 12/417,779, filed Apr. 3, 2009, which claims priority to U.S. provisional patent application 61/042,561, filed Apr. 4, 2008, the entire contents of each of which are hereby incorporated by reference. U.S. patent application Ser. No. 11/935,655, filed Nov. 5, 2007; U.S. patent application Ser. No. 12/059,484, filed Mar. 31, 2008; and U.S. patent application Ser. No. 12/389,946, filed Feb. 20, 2009; are incorporated herein by reference in their entirety.

Immunolight, LLC and Duke University are parties to a joint research agreement.

BACKGROUND OF THE INVENTION

Field of Invention

The present invention relates to methods and systems for treating a disorder or condition in a subject, that provide better distinction between normal, healthy cells and those cells suffering the disorder or condition (hereafter "target cells") and preferably that can be performed using non-invasive or minimally invasive techniques.

Discussion of the Background
Photobiomodulation

Photobiomodulation also known as low level laser therapy (LLLT), cold laser therapy, and laser biostimulation, is an emerging medical and veterinary technique in which exposure to low-level laser light can stimulate or inhibit cellular function leading to beneficial clinical effects. The "best" combination of wavelength, intensity, duration and treatment interval is complex and sometimes controversial with different diseases, injuries and dysfunctions needing different treatment parameters and techniques.

Certain wavelengths of light at certain intensities (delivered by laser, LED or another monochromatic source) will, for example, aid tissue regeneration, resolve inflammation, relieve pain and boost the immune system. The exact mechanism is still being explored and debated but it is agreed that the mechanism is photochemical rather than heat-related. Observed biological and physiological effects include changes in cell membrane permeability, and up-regulation and down-regulation of adenosine triphosphate and nitric oxide.

All light-induced biological effects depend on the parameters of the irradiation (wavelength, dose, intensity, irradiation time, depth of a target cell, and continuous wave or pulsed mode, pulse parameters). (See, e.g., Karu I T, Low-Power Laser Therapy", in Biomedical Photonics Handbook, Vo-Dinh T. Ed., CRC Press, Boca Raton, Fla., pp. 48-1 to 48-25, (2003)). Laser average power is typically in the range of 1-500 mW; some high peak power, short pulse width devices are in the range of 1-100 W with typically 200 ns pulse widths. The average beam irradiance then is typically 10 mW/cm$^2$-5 W/cm$^2$. The wavelength is typically in the range 600-1000 nm. The red-to-near infrared (NIR) region is preferred for photobiomodulation. Other wavelengths may be also used, e.g., UV light for neurons and green light for prostate tissue. Maximum biological responses are occurring when irradiated at 620, 680, 760, and 820-830 nm (Karu T I, et al., (1998). The Science of Low Power Laser Therapy. Gordon and Breach Sci. Publ., London). Large volumes and relatively deeper layers of tissues can be successfully irradiated by laser only (e.g., inner and middle ear diseases, injured siatic or optical nerves, inflammations). The LEDs are used for irradiation of surface injuries.

Karu (2003) is a comprehensive review of clinical applications of low-power-laser medicine. Direct activation of various types of cells via light absorption in mitochondria is described. The spontaneously active neurons responded strongly to He—Ne laser irradiation. Irradiation experiments were performed with neurons in connection with low power laser therapy. When excitable cells (e.g., neurons, cardiomyocites) are irradiated with monochromatic visible light, photoacceptors are also believed to be the components of the respiratory chain. It is described that since 1947, it has been known that mitochondria of excitable cells have photosensitivity. Experimental evidence concerning excitable cells is summarized.

A photoacceptor must first absorb the light used for the irradiation. After promotion of electronically excited states, primary molecule processes from these states can lead to a measurable biological effect (via secondary biochemical reaction, or photosignal transduction cascade, or cellular sigialing) at the cellular level. A photoacceptor for eukaryotic cells in red-to-NIR region is believed to be the terminal enzyme of the respiratory chain cytochrome c oxidase located in cell mitochondrion. In the violet-to blue spectra region, flavoprotein (e.g., NADHdehydrogenase in the beginning of the respiratory chain) is also among the photoacceptors.

Clinical applications of photobiomodulation include, for example, treating soft tissue and bone injuries, chronic pain, wound healing, nerve regeneration, sensory regeneration/restoration and possibly even resolving viral and bacterial infections, treating neurological and phychiatric diseases (e.g., epilepsy and Parkinson's disease) (e.g., Zhang F., et al., Nature, 446:617-9 (Apr. 5, 2007; Han X., et al., PloS ONE, 2(3):e299 (Mar. 21, 2007); Arany P R, et al., Wound Repair Regen., 15(6):866-74 (2007); Lopes C B, et al., Photomed. Laser Surg., 25(2):96-101 (2007)). One clinical application showing great promise is the treatment, of inflammation, where the anti-inflammatory effect of location-and-dose-specific laser irradiation produces similar outcomes as NSAIDs, but without the potentially harmful side-effects (Bjordal J M, Couppé C, Chow R T, Tuner J, Ljunggren E A (2003). "A systematic review of low level laser therapy with location-specific doses for pain from chronic joint disorders". The Australian journal of physiotherapy 49(2):107-16).

Han et al. (2007) describe a multiple-color optical activation, silencing, and desynchronization of neural activity with single-spike temporal resolution. It was shown that trains of yellow and blue light pulses can drive high-fidelity sequences of hyperpolarizations and depolarizations in neurons simultaneously expressing yellow light-driven Halo and blue light-driven ChR2, allowing for the first time manipulations of neural synchrony without perturbation of other parameters such as spiking rates. The Halo/ChR2 system thus constitutes a powerful toolbox for multichannel photoinhibition and photostimulation of virally or transgenically targeted neural circuits without need for exogenous chemicals, enabling systematic analysis and engineering of the brain, and quantitative bioengineering of excitable cells.

An NIR light treatment can prevent cell death (apoptosis) in cultured neurons (brain) cells (Wong-Reiley M T, et al., JBC, 280(6):4761-71 (2005)). Specific wavelengths of light can promote cellular proliferation to the activation of mitochondria, the energy-producing organelles within the cell via cytochrome c oxidase. An NIR treatment can augment mitochondrial function and stimulate antioxidant protective pathways. The evidence that the NIR treatment can augment mitochondrial function and stimulate antioxidant protective pathways comes from photobiomodulation experiments carried out using a laboratory model of Parkinson's disease (PD) (cultures of human dopaminergic neuronal cells) (Whelan H., et. al., SPIE, Newsroom, pages 1-3 (2008)).

Whelan et al. (Feb. 24, 2008) is a review that analyses a body of existing study and describes that the technique of photobiomodulation is based on the phenomenon that exposure to low-level laser light can alter cellular function. Evidence has indicated that near-IR light treatment can prevent cell death (apoptosis) in cultured neuronal cells. Irradiation at 660-680 nm has been shown to increase the activity of purified cytochrome oxidase, increase the energy production rates of isolated mitochondria, and upregulate cytochrome oxidase activity in cultured neuronal cells. Together, these data indicated that cytochrome oxidase, and thus mitochondria energy production, are cellular targets influenced by near-IR light treatment. 670 nm light cell pretreatment ameliorates the toxicity of the Parkinsonian drug MPTP. Near-IR light treatment modifies cellular function, promotes cell survival, and improves outcomes in laboratory and mouse models of Parkinson's disease.

It has also been shown that light has both inductive and inhibitory effect on cell growth and division in a red tide flagellate, *Chattonella antique* (Nemote Y., Plant and Cell Physiol., 26(4):669-674 (1985)).

When the excitable cells (e.g., neurons, cardiomyocites) are irradiated with monochromatic visible light, the photoacceptors are also believed to be components of respiratory chain. It is clear from experimental data (Karu, T. I., (2002). Low-power laser therapy. In: CRC Biomedical Photonics Handbook, T. Vo-Dinh, Editor-in-Chief, CRC Press, Boca Raton (USA)) that irradiation can cause physiological and morphological changes in nonpigmental excitable cells via absorption in mitochondria. Later, similar irradiation experiments were performed with neurons in connection with low-power laser therapy. It was shown in 80's that He—Ne laser radiation alters the firing pattern of nerves; it was also found that transcutaneous irradiation with HeNe laser mimicked the effect of peripheral stimulation of a behavioral reflex. These findings were found to be connected with pain therapy (Karu T I, et al., (2002)).

Karu (2002) is a review on CELLULAR MECHANISMS OF LOW POWER LASER THERAPY. Low power laser (photobiomodulation therapy) acts directly on the organism at the molecular level. The irradiation with He—Ne laser causes not only rapid regulation of ATP synthesis in directly irradiated cells, but also can affect the control of mitochondrial activity via protein synthesis (transcription and/or translation control).

When photoacceptors absorb photons, electronic excitation followed by photochemical reactions occurring from lower excitation states (first singlet and triplet) take place. It is also known that electronic excitation of absorbing centers alters their redox properties. Until yet, five primary reactions have been discussed in literature (Karu T I, et al., (2002)). Two of them are connected with alteration of redox properties and two mechanisms involve generation of reactive oxygen species (ROE). Also, induction of local transient (very short time) heating of absorbing chromophores is possible. Details of these mechanisms can be found in (Karu T I, et. al., (2002); Karu T I, et al., (1998). The Science of Low Power Laser Therapy. Gordon and Breach Sci. Publ., London).

Photobiological action via activation of respiratory chain is believed to be a general mechanism occurring in cells. Crucial events of this type of cell metabolism activation are occurring due to a shift of cellular redox potential into more oxidized direction as well as due to ATP extrasynthesis. Susceptibility to irradiation and capability for activation depend on physiological status of irradiated cells: the cells, which overall redox potential is shifted to more reduced state (example: some pathological conditions) are more sensitive to the irradiation. The specificity of final photobiological response is determined not at the level of primary reactions in the respiratory chain but at the transcription level during cellular signaling cascades. In some cells, only partial activation of cell metabolism happens by this mechanism (example: redox priming of lymphocytes).

Far red and NIR radiation have been shown to promote wound healing, e.g., infected, ischemic, and hypoxic wounds (Wong-Riley, WTT, JBC, 280(6):4761-4771 (2005)). Red-to-NIR radiation also protects the retina against the toxic actions of methanol-derived formic acid in a rodent model of methanol toxicity and may enhance recovery from retinal injury and other ocular diseases in which mitochondrial dysfunction is postulated to play a role (Eells J T., PNAS, 100(6):3439-44 (2003)). Other clinical applications of photobiomodulation is repair of soft and bone tissues by IR laser irradiation (Martinez M E, et al., Laser in Med. Sci., 2007). Invasive laser assisted liposuction is a recently developed method, wherein a laser fiber is introduced through a tube into the skin and directly to the fat cells causing the cells to rapture and drain away as liquid (Kim K H, Dermatol. Surg., 32(2):241-48 (2006)). Tissue around the area is coagulated. Yet, another application of photobiomodulation is a non-surgical varicose vein treatment (an endovenous laser therapy), wherein a laser is threaded through an incision and the full length of the varicose vein (Kim H S, J. Vase. Interv. Radiol., 18(6):811 (2007)). When the laser is slowly withdrawn, heat is applied to the vein walls, causing the vein to permanently close and disappear.

Technological advances such as laser have redefined the surgical treatment of enlarged prostate. The green light laser is a laser that vaporizes and removes the enlarged prostate tissue (Heinrich E., Eur. Urol., 52(6):1632-7 (2007)). The significance of the color of the laser light (green) is that this results in absorption by hemoglobin which is contained within red blood cells and not absorbed by water. The procedure may also be known as laser prostatectomy or laser Transurethral resection of the prostate (TURP). The technique involves painting the enlarged prostate with the laser until the capsule of the prostate is reached. By relieving this portion of the prostate, patients are able to void much easier through a wide-open channel in the prostate. The procedure needs to be performed under general or spinal anesthesia. An advantage of the procedure is that even patients taking blood thinners (e.g., aspirin to prevent stroke) can be treated because there is less bleeding compared to a traditional surgery.

Yet, another area of application of photobiomodulation is a direct control of brain cell activity with light. The technique is based upon NIR spectroscopy and is simpler to use and less expensive than other methods such as functional magnetic resonance imaging and positron emission tomography.

Whenever a region of the brain is activated that part of the brain uses more oxygen. This technique works by measuring the blood flow and oxygen consumption in the brain. The light emitted by NIR laser diodes is carried through optical fibers to a person's head. The light penetrates the skull where it assesses the brain's oxygen level and blood volume. The scattered light is then collected by optical fibers, sent to detectors and analyzed by a computer. By examining how much of the light is scattered and how much is absorbed, portions of the brain and extract information about brain activity can be mapped. By measuring the scattering, it is determined where the neurons are firing. This means that scientists can simultaneously detect both blood profusion and neural activity. The technique could be used in many diagnostic, prognostic and clinical applications. For example, it could be used to find hematomas in children, to study blood flow in the brain during sleep apnea, and to monitor recovering stroke patients on a daily, or even hourly, basis (that would be impractical to do with MRI). To validate the technique, hemoglobin oxygen concentrations in the brain obtained simultaneously by NIR spectroscopy and by functional MRI, the current "gold standard" in brain studies, was compared. Both methods were used to generate functional maps of the brain's motor cortex during a periodic sequence of stimulation by finger motion and rest. Spatial congruence between the hemoglobin signal and the MRI signal in the motor cortex related to finger movement was demonstrated. The researchers also demonstrated collocation between hemoglobin oxygen levels and changes in scattering due to brain activities. The changes in scattering associated with fast neuron signals came from exactly the same locations.

A low-intensity laser light-oxygen cancer therapy is another application of photobiomodulation. The light-oxygen effect (LOE), which involves activation of or damage to biosystems by optical radiation at low optical doses by direct photoexcitation of molecular oxygen dissolved in a biosystem so that it is converted to the singlet state, i.e., by photogeneration of molecular singlet oxygen from $O_2$ dissolved in cells, similar to photodynamic effect (Zakharov S D, et al., Quantum Electronics, 29(12):1031-53 (1999)). It was shown that the He—Ne laser radiation destroys tumor cells in the presence or absence of the photosensitiser. The LOE can be activated by small optical doses, which are 4-5 orders of magnitude lower that those found if a comparison is made with the familiar analogue in the form of the photodynamic effect (PDE).

Photobiostimulation Using "Caged" Molecules and Light-Sensitive Proteins

This type of photobiomodulation methods fall into two general categories: one set of methods uses light to uncage a compound that then becomes biochemically active, binding to a downstream effector. For example, this method involves applying "caged" chemicals to a sample and then using light to open the cage to invoke a reaction. Modified glutamate is useful for finding excitatory connections between neurons, since the uncaged glutamate mimics the natural synaptic activity of one neuron impinging upon another. This method is used for elucidation of neuron functions and imaging in brain slices using, for example, two-photon glutamine uncageing (Harvey C D, et al., Nature, 450:1195-1202 (2007); Eder M, et al., Rev. Neurosci., 15:167-183 (2004)). Other signaling molecules can be released by UV light stimulation, e.g., GABA, secondary messengers (e.g., $Ca^{2+}$ and $Mg^{2+}$), carbachol, capsaicin, and ATP (Zhang F., et al., 2006).

Eder et al. (2003) is a review of the technical aspects of photostimulation and recent findings and of mapping distribution and properties of functional neurotransmitter receptors on the surface of a single neuron in the living brain slice. The ability to use light as a stimulation tool provides a non-invasive method of the temporally and spatially precise activation of any neuron or any part of a neuron. The use of UV light such as UV-laser provides the spatially most precise stimulation of a neuronal structure. Photostimulation provides a useful tool to estimate the densities of neurotransmitter receptors at different sites of the neuronal membrane. Photostimulation was also used to assess KA receptors contribute to the excitatory postsynaptic current (EPSC) at different types of synapses and are crucially involved in many neurological diseases (e.g. epilepsy, Alzheimer's disease and Huntington's chorea). MN-glutamate now allows for a two photon excitation of the neuronal membrane. UV laser stimulation is described. A summary of the main findings regarding synaptic connectivity obtained by photostimulation using UV laser stimulation is presented. It is described that photostimulation is well suited for fast mapping the synaptic connectivity between nearby and, even more important, distant neurons in neuronal networks.

The other major photostimulation method is the use of light to activate a light-sensitive protein such as rhodopsin (ChR2), which can then excite the cell expressing the opsin.

It has been shown that channelrhodopsin-2, a monolithic protein containing a light sensor and a cation channel, provides electrical stimulation of appropriate speed and magnitude to activate neuronal spike firing. Recently, photoinhibition, the inhibition of neural activity with light, has become feasible with the application of molecules such as the light-activated chloride pump halorhodopsin to neural control. Together, blue-light activated channelrhodopsin-2 and the yellow light-activated chloride pump halorhodopsin enable multiple-color, optical activation and silencing of neural activity.

ChR2 photostimulaiton involves genetic targeting ChR2 to neurons and light pulsing the neurons expressing ChR2 protein. The experiments have been conducted in vitro and in vivo in mice by in vivo deep-brain photostimulaiton using optical fibers to deliver light into the lateral hypothalamus (Adamantidis A R, et al., Nature 450:420-425 (2007)). Genetic targeting of ChR2 allows exclusive stimulation of defined cellular subsets and avoids the need for addition of the caged glutamate, facilitating photostimulation in vivo (Wang H., et al., PNAS, 104(19):8143-48 (2007)). ChR2 photostimulation has been used for restoring visual activity in mice with impaired vision, to evoke behavioral responses in worms and flies (Wang H., et al., 2007). The robust associative learning induced by ChR2-assisted photostimulaiton in mice opens the door to study the circuit basis of perception and cognition in vivo (Huber D., et al., 2007). This kind of neuronal targeting and stimulation might have clinical application, e.g., deep brain stimulation to treat Parkinson's disease and other disorders, controlling behavioral, perceptional and cognitive characteristics, and for imaging and studying how the brain works (Zhang F., et al., Nature Methods, 3(10):785-792 (2006); Wong-Riley M T., et al., JBC, 280(6):4761-4771 (2005)).

Wang H., et al. (2007) describe use of transgenic mice that express the light activated cation channel Channelrhodopsin-2 (ChR2) in subsets of neurons for activation and functional mapping of neural circuits. Photostimulation could evoke synaptic transmission between neurons, and it was possible to map the spatial distribution of synaptic circuits connecting neurons within living cerebral cortex. ChR2 is a genetically based photostimulation technology that permits analysis of neural circuits with high spatial and temporal resolution in transgenic mammals. The use of ChR2 allowed to restore visual responses in mice with impaired vision and to evoke behavioral responses in worms and flies. ChR2 photostimulation is a powerful addition to the genetic tools currently available for manipulating and mapping neuronal circuits in brain tissue. Illumination with light pulses of 465-495 nm and 458 or 488 nm wavelength was used.

Zhang et al. (2006) describe that photostimulation provides a versatile alternative to electrode stimulation and light beams that can be manipulated to target one or many neurons. An algal light-gated ion channel Channelrhodopsin-2 is a model for photostimulation (PBS0 experiments. A summary of temporal, spatial, and technical properties of different photostimulation techniques and wavelengths for PBS and selection of proper PBS techniques are described. The article explains matching of light sources to photostimulation techniques, cites the published data on ChR2 techniques in rat and mouse hypothalamus neurons, mouse retinal neurons, chick spinal cord neurons and worm neurons, and addresses photostimulation in the intact neuronal tissue.

Wong-Riley et al. (2005) describe that 670 nm light-emitting diode (LED) arrays suggest that cytochrome c oxidase, a photoacceptor in the NIR range, plays an important role in therapeutic photobiomodulation. They used primary cultured neurons and tested the 670, 728, 770, 830, and 880 nm wavelengths. The mechanism of photobiomodulation involves the up-regulation of cytochrome c oxidase, leading to increased energy metabolism in neurons functionally inactivated by toxins. The endogenous mitochondrial enzyme, cytochrome c oxidase, is an important biological photoacceptor that mediates photobiomodulation in the far red and near infrared range. KCN and TTX toxins significantly down-regulated cytochrome c oxidase activity in neurons, and LED reversed the detrimental effects of the toxins. The article points out that there are clear clinical advantages for treatment using wavelengths within the tissue transparency window of 650-1000 nm.

Huber et al. (2007) describe that sparse optical microstimulation in barrel cortex drives learned behavior in freely moving mice. Photostimulation of genetically defined neurons27 has key advantages compared with electrical microstimulation. The goal was to establish causal links between the activity of groups of neurons and perceptual and cognitive functions by using a ChR2 photostimulation technique in vivo, Perceptual decisions and learning can be driven by extremely brief epochs of cortical activity in a sparse subset of supragranular cortical pyramidal neurons. These experiments demonstrated that photostimulation of layer 2/3 neurons drive robust behavior. They determined the relation between performance and the number of neurons directly activated by light. An imaging window was implanted on the electroporated mice and a miniature blue high-power LED (470 nm peak wavelength) was mounted on the imaging window.

Adamantidis et al. (2007) describe study that established a causal relationship between frequency-dependent activity of a genetically defined neural cell type and a specific mammalian behavior central to clinical conditions and neurobehavioral physiology. The study probed to impact of Hert neuron activity on sleep state transitions with in vitro neural photostimulation with genetically targeting to ChR-2 to licit cells and using an optical fiber to deliver light deep in the brain of mice. ChR2-expressing Hert neurons could precisely respond to light pulses. In vivo photostimulation efficiently activates the Hert neuron population.

Another gene, chloride pump (NpHR), which is borrowed from a microbe called an archaebacterium, can make neurons less active in the presence of yellow light. Combined, the two genes ChR2 and NpHR can now make neurons obey pulses of light like drivers obey a traffic signal: Blue means "go" (emit a signal), and yellow means "stop" (don't emit).

Light-sensitive proteins can be introduced into cells or live subjects via a number of techniques including electroporation, DNA microinjection, viral delivery, liposomal transfection and calcium-phosphate precipitation.

A third photostimulation technique is chemical modification of ion channels and receptors to render them light-responsive. Some of the most fundamental signaling mechanisms in a cell involve the release and uptake of $Ca^{2+}$ ions. $Ca^{2+}$ is involved in controlling fertilization, differentiation, proliferation, apoptosis, synaptic plasticity, memory, and developing axons. It has been shown that $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Directly controlling a brain cell activity with light is a novel means for experimenting with neural circuits and could lead to therapies for some disorders. This accomplishment is a step toward the goal of mapping neural circuit dynamics on a millisecond timescale to see if impairments in these dynamics underlie severe psychiatric symptoms. Knowing the effects that different neurons have could ultimately help researchers figure out the workings of healthy and unhealthy brain circuits. If use of the technique can show that altered activity in a particular kind of neuron underlies symptoms, for example, this insight will allow development of targeted genetic or pharmaceutical treatments to fix those neurons. Conceivably, direct control of neuronal activity with light could someday become a therapy in itself.

In living organisms, scientists were able to cause worms, *C. elegans*, to stop swimming while their genetically altered motor neurons were exposed to pulses of yellow light intensified through a microscope. In some experiments, exposure to blue light caused the worms to wiggle in ways they weren't moving while unperturbed. When the lights were turned off, the worms resumed their normal behavior.

Meanwhile, in experiments in living brain tissues extracted from mice, the researchers were able to use the technique to cause neurons to signal or stop on the millisecond timescale, just as they do naturally. Other experiments showed that cells appear to suffer no ill effects from exposure to the light. They resume their normal function once the exposure ends.

The most direct application of an optical neuron control is experimenting with neural circuits to determine why unhealthy ones fail and how healthy ones work.

In patients with Parkinson's disease, for example, researchers have shown that electrical "deep brain stimulation" of cells can help patients, but they don't know precisely why. By allowing researchers to selectively stimulate or dampen different neurons in the brain, the light stimulation techniques could help in determining which particular neurons are benefiting from deep brain stimulation. That could lead to making the electrical treatment, which has some unwanted side effects, more targeted.

Another potential application is experimenting with simulating neural communications. Because neurons communicate by generating patterns of signals-sometimes on and sometimes off like the 0s and 1s of binary computer code-flashing blue and yellow lights in these patterns could compel neurons to emit messages that correspond to real neural instructions. In the future, this could allow researchers to test and tune sophisticated neuron behaviors. Much farther down the road, the ability to artificially stimulate neural signals, such as movement instructions, could allow doctors to bridge blockages in damaged spinal columns, perhaps restoring some function to the limbs of paralyzed patients.

Finally, the technique could be useful in teasing out the largely unknown functioning of healthy brains.

Problems with LLLT, Cold Laser Therapy, and Laser Biostimulation

The laser systems currently used for biostimulation do not allow performing photobiomodulation in a region deep within thick tissue without a surgical invasion. Laser therapy is mostly conducted in surface or near surface target cells and tissue because penetration of UV and red-to-N IR radiation used for photobiomodulation and photobiostimulaiton is no more than a few centimeters beneath the surface of the skin. In addition, imaging and stimulation of brain cells is mainly possible in thin brain slices, or a thin monolayer or suspension of cells. For deeper tissue laser therapy in situ, a subject undergoes various invasive surgical procedures, e.g., invasive insertion of a fiber via incisions into a fat layer or veins, implanting a radiation source in deep tissue, or implanting a glass window above the barrel cortex (Huber D., et al., Nature, 451:61-66 (published Jan. 3, 2008)). It is further well recognized that another problem associated with the existing methods of photobiomodulation is in differentiation of normal cells from target cells.

Phototherapy

There are two main types of reactions in phototherapy:

(1) Type I reactions involve electrons and hydrogen atoms, which are transferred between photo-active molecules (also called photosensitizers) and substrates or solvent molecules. Oxygen may participate in subsequent reactions: e.g., psoralens in photopheresis and PUVA.

(2) Type II reactions involve singlet oxygen formation by energy transfer from PA molecules in the lowest triplet state to oxygen in the ground state: e.g., photodynamic therapy (PDT)

Photodynamic therapy (PDT) is a treatment modality that uses a photosensitizing agent and laser light to kill cells. PDT is a relatively new light-based treatment, which has recently been approved by the United States Food & Drug Administration (FDA) for the treatment of both early and late-stage lung cancer. Other countries have approved PDT for treatment of various cancers as well. Unlike chemotherapy, radiation, and surgery, PDT is useful in treating all cell types, whether small cell or non-small cell carcinoma. PDT involves treatment of diseases such as cancer using light action on a special photoactive class of drugs, by photodynamic action in vivo to destroy or modify tissue [Dougherty T. J. and Levy J. G., "Photodynamic Therapy and Clinical Applications", in *Biomedical Photonics Handbook*, Vo-Dinh T., Ed., CRC Press, Boca Raton Fla. (2003)]. PDT, which was originally developed for treatment of various cancers, has now been used to include treatment of pre-cancerous conditions, e.g. actinic keratoses, high-grade dysplasia in Barrett's esophagus, and non-cancerous conditions, e.g. various eye diseases, e.g. age related macular degeneration (AMD). Photodynamic therapy (PDT) is approved for commercialization worldwide both for various cancers (lung, esophagus) and for AMD.

The PDT process requires three elements: (1) a PA drug (i.e., photosensitizer), (2) light that can excite the photosensitizer and (3) endogenous oxygen. The putative cytotoxic agent is singlet oxygen, an electronically excited state of ground state triplet oxygen formed according to the Type II photochemical process, as follows.

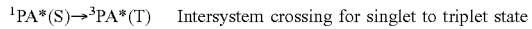

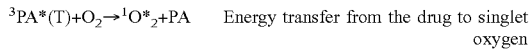

where PA=photo-active drug at the ground state; $^1PA^*(S)$=excited singlet state; $^3PA^*(T)$=excited triplet state; $^1O^*_2$=singlet excited state of oxygen Because the triplet state has a relatively long lifetime (μsec to seconds) only photosensitizers that undergo efficient intersystem crossing to the excited triplet state will have sufficient time for collision with oxygen in order to produce singlet oxygen. The energy difference between ground state and singlet oxygen is 94.2 kJ/mol and corresponds to a transition in the near-infrared at ~1270 nm. Most PA photosensitizers in clinical use have triplet quantum yields in the range of 40-60% with the singlet oxygen yield being slightly lower. Competing processes include loss of energy by deactivation to ground state by fluorescence or internal conversion (loss of energy to the environment or surrounding medium).

However, while a high yield of singlet oxygen is desirable it is by no means sufficient for a photosensitizer to be clinically useful. Pharmacokinetics, pharmacodynamics, stability in vivo and acceptable toxicity play critical roles as well [Henderson B W, Gollnick S O, "*Mechanistic Principles of Photodynamic Therapy*", in *Biomedical Photonics Handbook*, Vo-Dinh T, Ed., CRC Press, Boca Raton Fla. (2003)]. For example, it is desirable to have relatively selective uptake in the tumor or other tissue being treated relative to the normal tissue that necessarily will be exposed to the exciting light as well. Pharmacodynamic issues such as the subcellular localization of the photosensitizer may be important as certain organelles appear to be more sensitive to PDT damage than others (e.g. the mitochondria). Toxicity can become an issue if high doses of photosensitizer are necessary in order to obtain a complete response to treatment. An important mechanism associated with PDT drug activity involves apoptosis in cells. Upon absorption of light, the photosensitiser (PS) initiates chemical reactions that lead to the direct or indirect production of cytotoxic species such as radicals and singlet oxygen. The reaction of the cytotoxic species with subcellular organelles and macromolecules (proteins, DNA, etc) lead to apoptosis and/or necrosis of the cells hosting the PDT drug. The preferential accumulation of PDT drug molecules in cancer cells combined with the localized delivery of light to the tumor, results in the selective destruction of the cancerous lesion. Compared to other traditional anticancer therapies, PDT does not involve generalized destruction of healthy cells. In addition to direct cell killing, PDT can also act on the vasculature, reducing blood flow to the tumor causing its necrosis. In particular cases it can be used as a less invasive alternative to surgery.

There are several chemical species used for PDT including porphyrin-based sensitizers. A purified hematoporphyrin derivative, Photofrin®, has received approval of the US Food and Drug Administration. Porphyrins are generally used for tumors on or just under the skin or on the lining of internal organs or cavities because theses drug molecules absorbs light shorter than 640 nm in wavelength. For tumors occurring deep in tissue, second generation sensitizers, which have absorbance in the NIR region, such as porphyrin-based systems [R. K. Pandey, "*Synthetic Strategies in* designing Porphyrin-Based Photo sensitizers', in *Biomedical Photonics Handbook*, Vo-Dinh T., Ed., CRC Press, Boca Raton Fla. (2003)], chlorines, phthalocyanine, and naphthalocyanine have been investigated.

PDT retains several photosensitizers in tumors for a longer time than in normal tissues, thus offering potential improvement in treatment selectivity. See Corner C., "Determination of [3H]- and [14C] hematoporphyrin derivative distribution in malignant and normal tissue," Cancer Res 1979, 3 9: 146-15 1; Young S W, et al., "Lutetium texaphyrin (PCI-0123) a near-infrared, water-soluble photosensitizer," Photochem Photobiol 1996, 63:892-897; and Berenbaum M C, et al., "Meso-Tetra(hydroxyphenyl)porphyrins, a new class of potent tumor photosensitisers with favorable selectivity," Br J Cancer 1986, 54:717-725. Photodynamic therapy uses light of a specific wavelength to activate the photosensitizing agent. Various light sources have been developed for PDT, which include dye lasers and diode lasers. Light generated by lasers can be coupled to optical fibers that allow the light to be transmitted to the desired site. See Pass 1-11, "Photodynamic therapy in oncology: mechanisms and clinical use," J Natl Cancer Inst 1993, 85:443-456. According to researchers, the cytotoxic effect of PDT is the result of photooxidation reactions, as disclosed in Foote C S, "Mechanisms of photooxygenation," Proa Clin Biol Res 1984, 170:3-18. Light causes excitation of the photosensitizer, in the presence of oxygen, to produce various toxic species, such as singlet oxygen and hydroxyl radicals. It is not clear that direct damage to DNA is a major effect; therefore, this may indicate that photoactivation of DNA crosslinking is not stimulated efficiently.

Furthermore, when laser light is administered via external illumination of tissue surfaces, the treatment effect of PDT is confined to a few millimeters (i.e. superficial). The reason for this superficial limitation is mainly the limited penetration of the visible light used to activate the photosensitizer. Thus, PDT is used to treat the surfaces of critical organs, such as lungs or intra-abdominal organs, without damage to the underlying structures. However, even these treatments require significantly invasive techniques to treat the surface of the affected organs. Clinical situations use the procedure in conjunction with surgical debulking to destroy remnants of microscopic or minimal gross disease. It is possible that the laser light and small amount of remaining microscopic and minimal gross disease results in too little or highly to damaged structures. Pre-clinical data show that some immune response is generated, but clinical trials have reported no auto vaccine effect similar to that produced by extracorporeal photopheresis in clinical conditions. Instead, the immune response appears to be vigorous only under limited conditions and only for a limited duration.

PDT retains several photosensitizers in tumors for a longer time than in normal tissues, thus offering potential improvement in treatment selectivity. See Comer C., "Determination of [3H]- and [14C] hematoporphyrin derivative distribution in malignant and normal tissue," Cancer Res 1979, 3 9: 146-15 1; Young S W, et al., "Lutetium texaphyrin (PCI-0123) a near-infrared, water-soluble photosensitizer," Photochem Photobiol 1996, 63:892-897; and Berenbaum M C, et al., "Meso-Tetra(hydroxyphenyl)porphyrins, a new class of potent tumor photosensitisers with favorable selectivity," Br J Cancer 1986, 54:717-725. Photodynamic therapy uses light of a specific wavelength to activate the photosensitizing agent. Various light sources have been developed for PDT that include dye lasers and diode lasers. Light generated by lasers can be coupled to optical fibers that allow the light to be transmitted to the desired site. See Pass 1-11, "Photodynamic therapy in oncology: mechanisms and clinical use," J Natl Cancer Inst 1993, 85:443-456. According to researchers, the cytotoxic effect of PDT is the result of photooxidation reactions, as disclosed in Foote C S, "Mechanisms of photooxygenation," Proa Clin Biol Res 1984, 170:3-18. Light causes excitation of the photosensitizer, in the presence of oxygen, to produce various toxic species, such as singlet oxygen and hydroxyl radicals. It is not clear that direct damage to DNA is a major effect; therefore, this may indicate that photoactivation of DNA crosslinking is not stimulated efficiently.

Photopheresis has been successfully used for treatment of cell proliferation disorders. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Of these, cancer is perhaps the most well known.

Other successful application of PDT is, for example, cardiac ablation therapy, e.g., treating cardiac arrhythmias and atrial fibrillation which are believed to be a significant cause of cerebral stroke.

U.S. Pat. No. 6,811,562 describes administering a photoactivatable agent and subjecting cardiac tissue containing the administered agent to laser irradiation having a wavelength from 350 to 700 nm using invasive techniques, e.g., a fiber optic element.

Yet, another application of PDT is photoangioplasty for arterial diseases including de novo atherosclerosis and restinosis (Rockson A G, et al., Circulation, 102:591-596 (2000); Hsiang Y N., et al., J. Endovasc. Surg., 2:365-371 (1995)). In human clinical applications, endovascular light (730 nm) is delivered through a cylindrical fiber after intravenous administration of motexafin lutetium. PDT is also used for preventing and treatment of intimal hyperplasia in blood vessels in vivo (see, e.g., U.S. Pat. No. 6,609,014).

Age-related macular degeneration (AMD) is a cause of new blindness. Choroidal neovascularization leads to hemorrhage and fibrosis in a number of ocular diseases. Conventional treatments utilize the argon laser to occlude the leaking vessel by thermal coagulation. However, the percentage of patients eligible for this treatment is limited. PDT is used for treating AMD and involves injecting verteporfin followed by the application of non-thermal light at 692 nm.

Improvement of clinical appearance of psoriatic plaques and palmopustular psoriasis using PUVA with hematopotphyrin was first reported in 1937. Acne, apopecia areata, portwine stains and hair removal also show promise with PDT treatment.

The choice of therapy usually depends on the location and severity of the disorder, the stage of the disease, as well as the patient's response to the treatment.

While some treatments may only seek to manage and alleviate symptoms of the disorder, the ultimate goal of any effective therapy is the complete removal or cure of all disordered cells without damage to the rest of the body.

In one existing treatment known as extracorporeal photopheresis (ECP), excellent results have been observed since its initial approval by the FDA in 1988.

Extracorporeal photopheresis is a leukapheresis-based immunomodulatory therapy that has been approved by the US Food and Drug Administration for the treatment of cutaneous T-cell lymphoma (CTCL). ECP, also known as extracorporeal photochemotherapy, is performed at more than 150 centers worldwide for multiple indications. Long-term follow-up data are available from many investigators that indicate ECP produces disease remission and improved survival for CTCL patients. In addition to CTCL, ECP has been shown to have efficacy in the treatment of other T-cell mediated disorders, including chronic graft versus host disease (GVHD) and solid organ transplant rejection. ECP use for the treatment of autoimmune disease, such as systemic sclerosis and rheumatoid arthritis, is also being explored.

ECP is generally performed using the UVAR XTS Photopheresis System developed by Therakos, Inc (Exton, Pa.). The process is performed through one intravenous access port and has 3 basic stages: (1) leukapheresis, (2) photoactivation, and (3) reinfusion, and takes 3-4 hours to complete. A typical treatment session would resemble the following sequence of events:

(1) One 16-gauge peripheral intravenous line or central venous access is established in the patient;

(2) Blood (225 mL) is passed through 3 cycles of leukapheresis, or 125 mL of blood is passed through 6 cycles, depending on the patient's hematocrit value and body size. At the end of each leukapheresis cycle, the red blood cells and plasma are returned to the patient;

(3) The collected WBCs (including approximately 5% of the peripheral blood mononuclear cells) are mixed with heparin, saline, and 8-methoxypsoralen (8-MOP), which intercalates into the DNA of the lymphocytes upon exposure to UVA light and makes them more susceptible to apoptosis when exposed to UVA radiation;

(4) The mixture is passed as a 1-mm film through a sterile cassette surrounded by UVA bulbs, resulting in an average UVA exposure of 2 $J/cm^2$; and (5) The treated WBC mixture is returned to the patient.

Over the past 20 years, on-going research has explored the mechanism of action of ECP. The combination of 8-MOP and UVA radiation causes apoptosis of the treated T cells and may cause preferential apoptosis of activated or abnormal T cells, thus targeting the pathogenic cells of CTCL or GVHD. However, given that only a small percentage of the body's lymphocytes are treated, this seems unlikely to be the only mechanism of action.

Other evidence suggests that ECP also induces monocytes to differentiate into dendritic cells capable of phagocytosing and processing the apoptotic T-cell antigens. When these activated dendritic cells are reinfused into the systemic circulation, they may cause a systemic cytotoxic $CD8^+$ T-lymphocyte-mediated immune response to the processed apoptotic T-cell antigens.

Finally, animal studies indicate that photopheresis may induce antigen-specific regulatory T cells, which may lead to suppression of allograft rejection or GVHD.

However, there are still many limitations to ECP. For example, ECP requires patient to be connected to a machine for hours per treatment. It requires establishing peripheral intravenous line or central venous access, which may be difficult to do in certain disease states such as systemic sclerosis or arthritis. There is also a risk of infection at the venous or central line site, or in the central line catheter. Further, it requires removing typically several hundred milliliters of whole blood from the patient, hence, the treatment is limited to patients who has sufficiently large initial volume of blood to be withdrawn. The American Association of Blood Blanks recommend a limit of extracorporeal volume to 15% of the patient's whole body blood volume. Therefore, the size of the volume that can be treated generally has to be at least 40 kg or more. Risk of contracting blood-born pathogen (Hepatitis, HIV, etc.) due to exposure to contaminated operating system is also a concern.

Alternatively, a patient can be treated in vivo with a photosensitive agent followed by the withdrawal of a sample from the patient, treatment with UV radiation in vitro (ex vivo), and reinjecting the patient with the treated sample. This method is known for producing an autovaccine. A method c f treating a patient with a photosensitive agent, exposing the patient to an energy source and generating an autovaccine effect wherein all steps are conducted in vivo has not been described. See WO 03/049801, U.S. Pat. Nos. 6,569,467; 6,204,058; 5,980,954; 6,669,965; 4,838,852; 7,045,124, and 6,849,058. Moreover, the side effects of extracorporeal photopheresis are well known and include nausea, vomiting, cutaneous erythema, hypersensitivity to sunlight, and secondary hematologic malignancy. Researchers are attempting to use photopheresis in experimental treatments for patients with cardiac, pulmonary and renal allograft rejection; autoimmune diseases, and ulcerative colitis.

A survey of known treatment methods reveals that these methods tend to face a primary difficulty of differentiating between normal cells and target cells when delivering treatment, often due to the production of singlet oxygen which is known to be non-selective in its attack of cells, as well as the need to perform the processes ex vivo, or through highly invasive procedures, such as surgical procedures in order to reach tissues more than a few centimeters deep within the subject.

U.S. Pat. No. 5,829,448 describes sequential and simultaneous two photon excitation of photo-agents using irradiation with low energy photons such as infrared or near infrared light (NRI). A single photon and simultaneous two photon excitation is compared for psoralen derivatives, wherein cells are treated with the photo agent and are irradiated with NRI or UV radiation. The patent suggests that treating with a low energy irradiation is advantageous because it is absorbed and scattered to a lesser extent than UV radiation. However, the use of NRI or UV radiation is known to penetrate tissue to only a depth of a few centimeters. Thus any treatment deep within the subject would necessarily require the use of ex vivo methods or highly invasive techniques to allow the irradiation source to reach the tissue of interest. Also, this patent does not describe initiation energy sources emitting energy other than UV, visible, and near infrared energy; energy upgrading other than within the range corresponding to UV and IR light, and downgrading from high to low energy.

Chen et al., J. Nanosci. and Nanotech., 6:1159-1166 (2006); Kim et al., JACS, 129:2669-2675 (2007); U.S. 2002/0127224; and U.S. Pat. No. 4,979,935 each describe methods for treatment using various types of energy activation of agents within a subject. However, each suffers from the drawback that the treatment is dependent on the production of singlet oxygen to produce the desired effect on the tissue being treated, and is thus largely indiscriminate in affecting both healthy cells and the diseased tissue desired to be treated.

U.S. Pat. No. 6,908,591 discloses methods for sterilizing tissue with irradiation to reduce the level of one or more active biological contaminants or pathogens, such as viruses, bacteria, yeasts, molds, fungi, spores, prions or similar agents responsible, alone or in combination, for transmissible spongiform encephalopathies and/or single or multicellular parasites, such that the tissue may subsequently be used in transplantation to replace diseased and/or otherwise defective tissue in an animal. The method may include the use of a sensitizer such as psoralen, a psoralen-derivative or other photosensitizer in order to improve the effectiveness of the irradiation or to reduce the exposure necessary to sterilize the tissue. However, the method is not suitable for treating a patient and does not teach any mechanisms for stimulating the photosensitizers, indirectly.

U.S. Pat. No. 5,957,960 discloses a two-photon excitation device for administering a photodynamic therapy to a treatment site within a patient's body using light having an infrared or near infrared waveband. However, the reference fails to disclose any mechanism of photoactivation using energy modulation agent that converts the initiation energy to an energy that activates the activatable pharmaceutical agent and also use of other energy wavebands, e.g., X-rays, gamma-rays, electron beam, microwaves or radio waves.

U.S. Pat. No. 6,235,508 discloses antiviral applications for psoralens and other photoactivatable molecules. It teaches a method for inactivating viral and bacterial contaminants from a biological solution. The method includes mixing blood with a photosensitizer and a blocking agent and irradiating the mixture to stimulate the photosensitizer, inactivating substantially all of the contaminants in the blood, without destroying the red blood cells. The blocking agent prevents or reduces deleterious side reactions of the photosensitizer, which would occur if not in the presence of the blocking agent. The mode of action of the blocking agent is not predominantly in the quenching of any reactive oxygen species, according to the reference.

Also, U.S. Pat. No. 6,235,508 suggests that halogenated photosensitizers and blocking agents might be suitable for replacing 8-methoxypsoralen (8-MOP) in photopheresis and in treatment of certain proliferative cancers, especially solid localized tumors accessible via a fiber optic light device or superficial skin cancers. However, the reference fails to address any specific molecules for use in treating lymphomas or any other cancer. Instead, the reference suggests a process of photopheresis for antiviral treatments of raw blood and plasma.

U.S. Pat. No. 6,235,508 teaches away from 8-MOP and 4'-aminomethyl-4,5',8-trimethylpsoralen (AMT) and many other photoactivatable molecules, which are taught to have certain disadvantages. Fluorescing photosensitizers are said to be preferred, but the reference does not teach how to select a system of fluorescent stimulation or photoactivation using fluorescent photosensitizers. Instead, the fluorescing photosensitizer is limited to the intercalator that is binding to the DNA. The reference suggests that fluorescence indicates that such an intercalator is less likely to stimulate oxygen radicals.

U.S. published application 2002/0127224 discloses a method for a photodynamic therapy comprising administering light-emitting nanoparticles and a photoactivatable agent, which may be activated by the light re-emitted from the nanoparticles via a two-photon activation event. An initiation energy source is usually a light emitting diode, laser, incandescent ramp, or halogen light, which emits light having a wavelength ranging from 350 to 1100 nm. The initiation energy is absorbed by the nanoparticles. The nanoparticles, in turn, re-emit light having a wavelength from 500 to 1100 nm, preferably, UV-A light, wherein the re-emitted energy activates the photoactivatable agent. Kim et al., (JACS, 129:2669-75, Feb. 9, 2007) discloses indirect excitation of a photosensitizing unit (energy acceptor) through fluorescence resonance energy transfer (FRET) from the two-photon absorbing dye unit (energy donor) within an energy range corresponding to 300-850 nm. These references do not describe initiation energy sources emitting energy other than UV, visible, and near infrared energy; energy upgrading other than within the range corresponding to wavelength of 350-1100 nm, and downgrading from high to low energy.

These references fail to disclose any mechanism of photoactivation of an photoactivatable molecules other than by direct photoactivation by UV, visible, and near infrared energy.

Psoralens and Related Compounds

U.S. Pat. No. 6,235,508 further teaches that psoralens are naturally occurring compounds which have been used therapeutically for millennia in Asia and Africa. The action of psoralens and light has been used to treat vitiligo and psoriasis (PUVA therapy; Psoralen Ultra Violet A). Psoralen is capable of binding to nucleic acid double helices by intercalation between base pairs; adenine, guanine, cytosine and thymine (DNA) or uracil (RNA). Upon sequential absorption of two UV-A photons, psoralen in its excited state reacts with a thymine or uracil double bond and covalently attaches to both strands of a nucleic acid helix. The cross-linking reaction appears to be specific for a thymine (DNA) or a uracil (RNA) base. Binding proceeds only if psoralen is intercalated in a site containing thymine or uracil, but an initial photoadduct must absorb a second UVA photon to react with a second thymine or uracil on the opposing strand of the double helix in order to crosslink each of the two strands of the double helix, as shown below. This is a sequential absorption of two single photons as shown, as opposed to simultaneous absorption of two or more photons.

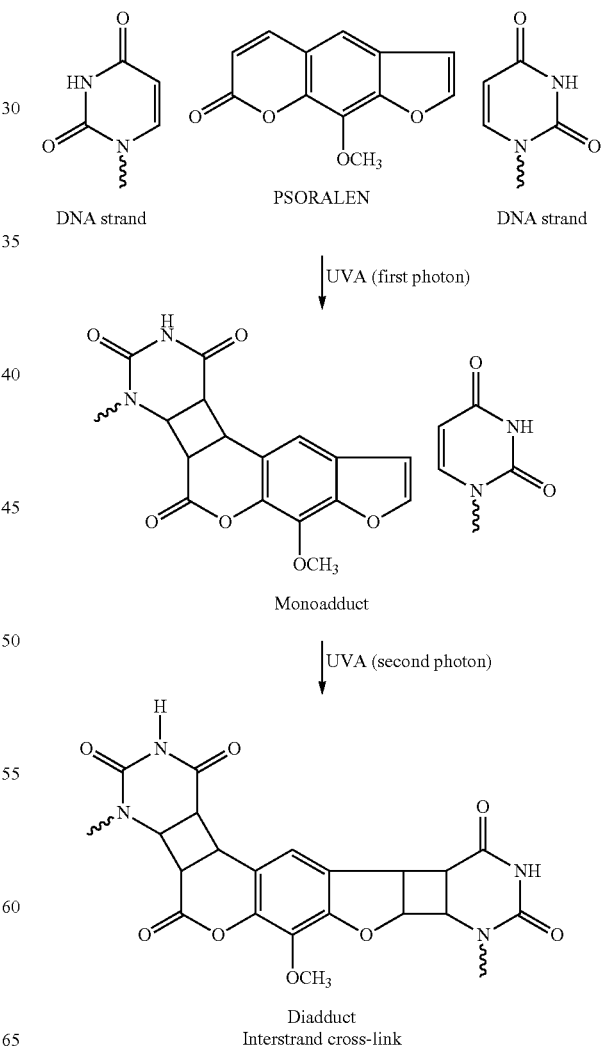

In addition, the reference teaches that 8-MOP is unsuitable for use as an antiviral, because it damages both cells and viruses. Lethal damage to a cell or virus occurs when the psoralen is intercalated into a nucleic acid duplex in sites containing two thymines (or uracils) on opposing strands but only when it sequentially absorbs 2 UVA photons and thymines (or uracils) are present. U.S. Pat. No. 4,748,120 of Wiesehan is an example of the use of certain substituted psoralens by a photochemical decontamination process for the treatment of blood or blood products.

Additives, such as antioxidants are sometimes used with psoralens, such as 8-MOP, AMT and I-IMT, to scavenge singlet oxygen and other highly reactive oxygen species formed during photoactivation of the psoralens. It is well known that UV activation creates such reactive oxygen species, which are capable of seriously damaging otherwise healthy cells. Much of the viral deactivation may be the result of these reactive oxygen species rather than any effect of photoactivation of psoralens. Regardless, it is believed that no auto vaccine effect has been observed.

The best known photoactivatable compounds are derivatives of psoralen or coumarin, which are nucleic acid intercalators. The use of psoralen and coumarin photosensitizers can give rise to alternative chemical pathways for dissipation of the excited state that are either not beneficial to the goal of viral inactivation, or that are actually detrimental to the process. For psoralens and coumarins, this chemical pathway is likely to lead to the formation of a variety of ring-opened species, such as shown below for coumarin:

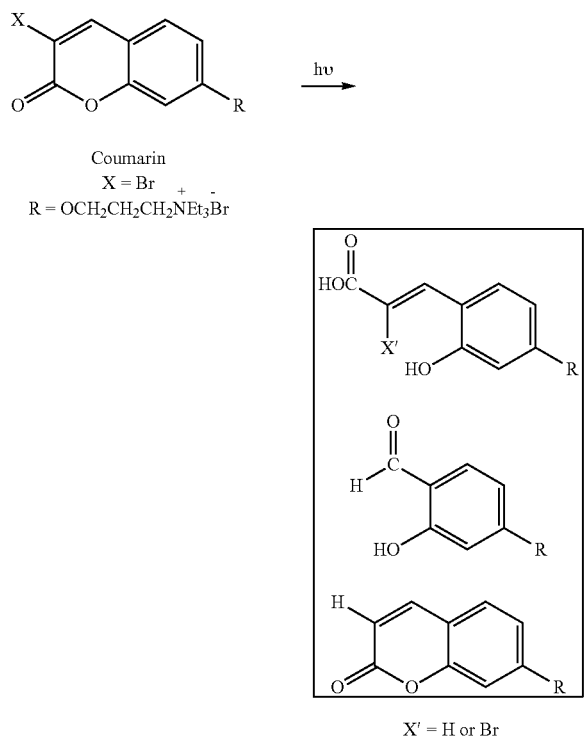

Research in this field over-simplifies mechanisms involved in the photoactivating mechanism and formation of highly reactive oxygen species, such as singlet oxygen. Both may lead to inactivating damage of tumor cells, viruses and healthy cells. However, neither, alone or combined, lead to an auto vaccine effect. This requires an activation of the body's own immune system to identify a malignant cell or virus as threat and to create an immune response capable of lasting cytotoxic effects directed to that threat. It is believed, without being limiting in any way, that photoactivation and the resulting apoptosis of malignant cells that occurs in extracorporeal photopheresis causes the activation of an immune response with cytotoxic effects on untreated malignant cells. While the complexity of the immune response and cytotoxic effects is fully appreciated by researchers, a therapy that harnesses the system to successfully stimulate an auto vaccine effect against a targeted, malignant cell has been elusive, except for extracorporeal photopheresis for treating lymphoma.

Midden (W. R. Midden, Psoralen DNA photobiology, Vol I1 (ed. F. P. Gaspalloco) CRC press, pp. 1. (1988) has presented evidence that psoralens photoreact with unsaturated lipids and photoreact with molecular oxygen to produce active oxygen species such as superoxide and singlet oxygen that cause lethal damage to membranes. U.S. Pat. No. 6,235,508 teaches that 8-MOP and AMT are unacceptable photosensitizers, because each indiscriminately damages both cells and viruses. Studies of the effects of cationic side chains on furocoumarins as photosensitizers are reviewed in Psoralen DNA Photobiology, Vol. I, ed. F. Gaspano, CRC Press, Inc., Boca Raton, Fla., Chapter 2. U.S. Pat. No. 6,235,508 gleans the following from this review: most of the amino compounds had a much lower ability to both bind and form crosslinks to DNA compared to 8-MOP, suggesting that the primary amino functionality is the preferred ionic species for both photobinding and crosslinking.

U.S. Pat. No. 5,216,176 of Heindel discloses a large number of psoralens and coumarins that have some effectiveness as photoactivated inhibitors of epidermal growth factor. Halogens and amines are included among the vast functionalities that could be included in the psoralen/coumarin backbone. This reference is incorporated herein by reference.

U.S. Pat. No. 5,984,887 discloses using extracorporeal photopheresis with 8-MOP to treat blood infected with CMV. The treated cells as well as killed and/or attenuated virus, peptides, native subunits of the virus itself (which are released upon cell break-up and/or shed into the blood) and/or pathogenic noninfectious viruses are then used to generate an immune response against the virus, which was not present prior to the treatment.

Problems with PDT

It is well recognized that a major problem associated with the existing methods of diagnosis and treatment of cell proliferation disorders is in differentiation of normal cells from target cells. Radiation therapy works by irradiating cells with high levels of high energy radiation such as high energy photon, electron, or proton. These high energy beams ionize the atoms which make up a DNA chain, which in turn leads to cell death. Unlike surgery, radiation therapy does not require placing patients under anesthesia and has the ability to treat disorders deep inside the body with minimal invasion of the body. However, the high doses of radiation needed for such therapies damages healthy cells just as effectively as it does diseased cells. Thus, similar to surgery, differentiation between healthy and diseased cells in radiation therapy is only by way of location. There is no intrinsic means for a radiation beam to differentiate between a healthy cell from a diseased cell either. Another problem encountered in PDT therapy is the inability to treat target areas that are more than a few centimeters beneath the surface of the skin without significant invasive techniques.

Therefore, there still exists a need for better and more effective treatments that can more precisely target the diseased cells without causing substantial side-effects or collateral damages to healthy tissues, and which are capable of treating disorders by non-invasive or minimum invasive techniques.

SUMMARY OF THE INVENTION

Accordingly, one object of the present invention is to provide a method for the treatment of a condition, disorder or disease in a subject that permits treatment of a subject in any area of the body while being non-invasive and having high selectivity for targeted cells relative to healthy cells.

A further object of the present invention is to provide a method for treatment of a condition, disorder or disease in a subject which can use any suitable energy source as the initiation energy source to induce a predetermined change in a target structure in a subject in situ to treat said condition, disorder or disease.

A further object of the present invention is to provide a method for treatment of a condition, disorder or disease using a modulation agent which adsorbs, intensifies or modifies the initiation energy into an energy that effects a predetermined change in a target structure.

These and other objects of the present invention, which will become more apparent in conjunction with the following detailed description of the preferred embodiments, either alone or in combinations thereof, have been satisfied by the discovery of a method for treating a condition, disorder or disease in a subject, comprising:

applying an initiation energy from at least one source to a target structure in a subject in need of treatment, wherein the initiation energy contacts the target structure and induces a predetermined change in said target structure in situ, thus treating said condition, disorder or disease.

Yet a further object of the invention is further administer at least one energy modulation agent to said subject which adsorbs, intensifies or modifies said initiation energy into an energy that effects a predetermined change in said target structure.

A further object of the present invention is to provide a method for treatment of a condition, disorder or disease which can use any suitable energy source as the initiation energy source to activate the activatable pharmaceutical agent and thereby cause a predetermined change in a target structure to treat a condition, disorder or disease.

A further object of the present invention is to provide a method for treatment of a condition, disorder or disease using an energy cascade to activate an activatable pharmaceutical agent that then treats cells suffering from a condition, disorder or disease.

A further object of the present invention is to provide a method for generating an autovaccine effect in a subject, which can be in vivo thus avoiding the need for ex vivo treatment of subject tissues or cells, or can be ex vivo.

A further object of the present invention is to provide a method for generating an autovaccine effect in a subject, which can be in vivo thus avoiding the need for ex vivo treatment of subject tissues or cells, or can be ex vivo.

A further object of the present invention is to provide a computer implemented system for performing the methods of the present invention.

A still further object of the present invention is to provide a kit and a pharmaceutical composition for use in the present invention methods.

These and other objects of the present invention, which will become more apparent in conjunction with the following detailed description of the preferred embodiments, either alone or in combinations thereof, have been satisfied by the discovery of a method for modifying a target structure which mediates or is associated with a biological activity comprising:

applying an initiation energy from at least one source to a target structure in a subject in need of treatment, wherein the initiation energy contacts the target structure and induces a predetermined change in said target structure in situ, wherein said predetermined change modifies the target structure and modulates the biological activity of the target structure.

A further object of the present invention is to provide a method for modifying a target structure which mediates or is associated with a biological activity, comprising:

(1) contacting said target structure with at least one activatable pharmaceutical agent (PA) that is capable of effecting a predetermined change in a target structure when activated, optionally in the presence of at least one member selected from the group consisting of energy modulation agents, plasmonics-active agents and combinations thereof; and (2) applying an initiation energy from an initiation energy source to said target structure, wherein the energy modulation agent, if present, upgrades or downgrades the initiation energy to an activation energy capable of activating the at least one activatable pharmaceutical agent;

wherein the plasmonics-active agent, if present, enhances or modifies the applied initiation energy or the activation energy generated by the energy modulation agent, or both; and thus causing the predetermined change to the target structure to occur, wherein said predetermined change modifies the target structure and modulates the biological activity of the target structure;

and a kit for performing the methods, pharmaceutical compositions, computer implemented systems for performing the methods and a method and system for causing an autovaccine effect in a subject.

A further object of the present invention is to provide such methods which can use any suitable energy source as the initiation energy source in combination with plasmonics materials to activate the activatable pharmaceutical agent and thereby cause the predetermined change.

A further object of the present invention is to provide such methods using plasmonics in an energy cascade to activate an activatable pharmaceutical agent that then cause the predetermined change.

A further object of the present invention is to provide such methods for in situ generation of energy which causes, either directly or indirectly, the predetermined change.

A further object of the present invention is to provide a method for the treatment of a cell proliferation disorder that permits treatment of a subject in any area of the body while being non-invasive and having high selectivity for targeted cells relative to healthy cells through the use of exciton-plasmon enhancement.

A further object of the present invention is to provide a method for treatment of a condition, disorder or disease which can use any suitable energy source as the initiation energy source in combination with exciton-plasmon enhancement to activate the activatable pharmaceutical agent and thereby cause a predetermined change to treat cells suffering from a condition, disorder or disease.

A further object of the present invention is to provide a method for treatment of a condition, disorder or disease using exciton-plasmon enhancement in an energy cascade to activate an activatable pharmaceutical agent that then treats cells suffering from a condition, disorder or disease.

Another object of the invention is a method for treating a condition, disorder, or disease associated with a target structure in a subject, comprising:
(1) administering to the subject at least one activatable pharmaceutical agent that is capable of effecting a predetermined change in a target structure when activated and at least one plasmonics-active agent; and
(2) applying an initiation energy from an initiation energy source to the subject,
wherein the plasmonics-active agent enhances or modifies the applied initiation energy, such that the enhanced initiation energy activates the activatable agent in situ, thus causing the predetermined change to the target structure to occur, wherein said predetermined change modifies the target structure and treats said condition, disorder, or disease. The condition, disorder, or disease may be mediated by abnormal cellular proliferation and said predetermined change can ameliorate the abnormal cellular proliferation. Abnormal cellular proliferation may be higher than that of cells from a subject not having said condition, disorder or disease or may be lower.

The treated condition, disorder, or disease may or may not be significantly mediated by abnormal cellular proliferation and said predetermined change does not have to substantially affect cellular proliferation.

Yet another object of the invention is a method for modifying a target structure which mediates or is associated with a biological activity, comprising:
(1) contacting said target structure with at least one activatable pharmaceutical agent that is capable of effecting a predetermined change in a target structure when activated and at least one plasmonics-active agent; and
(2) applying an initiation energy from an initiation energy source to target structure
wherein the plasmonics-active agent enhances or modifies the applied initiation energy, such that the enhanced initiation energy activates the activatable agent,
thus causing the predetermined change to the target structure to occur, wherein said predetermined change modifies the target structure and modulates the biological activity of the target structure. The target structure need not be present inside an organism, but may be one in vitro or ex vivo. The predetermined change may enhance the expression of, promote the growth of, or increase the quantity of the target structure; or the predetermined change can enhance, inhibit or stabilize the usual biological activity of the target structure compared to a similar untreated target structure. For example, the predetermined change can alter the immunological or chemical properties of the target structure which may be a cell, cell membrane, internal cellular structure, polypeptide or non-polypeptide compound which can be modified by said predetermined change to be more or less antigenic or immunogenic. In another embodiment, modifying the target structure can be done without the need for a pharmaceutical agent, or a plasmonics-active agent.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 6A shows silver nanospheres with different radii. FIG. 6B shows nanoshells with different dielectric core/metallic shell radial ratios. [M. M. Kerker, Acc. Chem. Res., 17, 370 (1984)]

FIG. 7 provides representative embodiments of plasmonics photo-active probes useful in the present invention.

FIG. 8 is a graphical explanation of the plasmonics-enhanced effect of photospectral therapy used in the present invention.

FIG. 9 provides representative embodiments of plasmonics-active nanostructures.

FIG. 15A: PA molecules bound to EEC and to plasmonic metal nanoparticles; FIG. 15B: Plasmonic metal nanoparticle with EEC nanocap covered with PA molecules; FIG. 15C: PA-covered nanoparticle with plasmonic metal nanoparticles; FIG. 15D: EEC-containing nanoparticle covered with PA molecules and plasmonic metal nanocap; FIG. 15E: Plasmonic metal nanoparticle core with EEC nanoshell covered with PA molecules; FIG. 15F: PA molecule bound to EEC (attached to plasmonics metal nanoparticle) nanoparticle by detachable biochemical bond.

FIG. 18 is a graphical representation of a plasmonics-enhanced mechanism for a photo-active energy modulation agent-PA probe of the present invention.

FIG. 19 is a graph showing excitation and emission fluorescence spectra of psoralens FIG. 20A shows that an EEC nanoparticle improves delivery of PA molecules (e.g., psoralen) into target disease cells. FIG. 20B shows that, inside the cell, photon radiation releases PA which can go into the nucleus. FIG. 20C shows that radiation of suitable wavelength (NIR to X ray) induces plasmonic field to activate PA intercalated into DNA.

FIG. 21 is a graphical representation of an embodiment of PEPST probes for dual plasmonic excitation.

FIG. 22 is a graphical representation of an embodiment of a use of encapsulated photoactive agents.

FIG. 23 is a simplified graphical representation of the use of the present invention principle of non-invasive PEP ST modality.

FIG. 24 is a photomicrograph showing nanocaps (half-nanoshells) comprising polystyrene nanospheres coated with silver.

FIG. 25 shows various schematic embodiments of basic EIP probes.

FIG. 26A shows fluorescence, excitation, emission, and synchronous spectra of phenanthrene. FIG. 26B shows fluorescence, excitation, emission, and synchronous spectra of anthracene. FIG. 26C shows fluorescence, excitation, emission, and synchronous spectra of perylene. FIG. 26D shows conventional fluorescence spectrum of a mixture of naphthalene, phenanthrene, anthracene, perylene, and tertracene. FIG. 26E shows synchronous spectrum of the mixture. [Source: T. Vo-Dinh, Multicomponent analysis by synchronous luminescence spectrometry, Anal. Chem.; 1978; 50(3) pp 396 401]

FIG. 28 provides further embodiments of schematic designs of EIP probes.

FIG. 29 is a graphical representation of various embodiments of basic EPEP probes.

FIG. 30 is a graphical representation of various embodiments of basic EPEP probes.

FIG. 31 is a graphical representation of various embodiments of EPEP probes having NPs, NWs and NRs.

FIG. 32 is a graphical representation of various embodiments of EPEP probes having NPs, NWs, NRs and bioreceptors.

FIG. 33 is a graphical representation of an embodiment of EPEP probes having NPs and multiple NWs.

FIG. 34A-34G show photo-active probes in which a photo-active molecule is bound to plasmonics probes. FIG. 34A: PA molecules bound to metal nanoparticle; FIG. 34B: X-ray converter nanoparticle covered with metal nanoparticles; FIG. 34C: Metal nanoparticle covered with X-ray converter nanocap; FIG. 34D: X-ray converter nanoparticle covered with metal nanocap; FIG. 34E: Metal nanoparticle covered with X-converter nanoshell; FIG. 34F: X-ray converter nanoparticle covered with metal nanoshell; and FIG. 34G: X-ray converter nanoparticle covered with metal nanoshell with protective coating layer.

FIG. 35A-35G show plasmonics photo-active probes that have a dielectric layer between the metal and the UC materials FIG. 35A: PA molecules bound to metal nanoparticle; FIG. 35B: X-ray converter nanoparticle covered with dielectric layer and metal nanoparticles; FIG. 35C: Metal nanoparticle covered with dielectric layer and X-ray converter nanocap; FIG. 35D: X-ray converter nanoparticle covered with dielectric layer and metal nanocap; FIG. 3 5E: Metal nanoparticle covered with dielectric layer and X-ray converter nanoshell; FIG. 35F: X-ray converter nanoparticle covered with dielectric layer and metal nanoshell; FIG. 35G: X-ray converter nanoparticle covered with dielectric layer, metal nanoshell and protective coating.

DETAILED DESCRIPTION OF THE INVENTION

Figure 1:
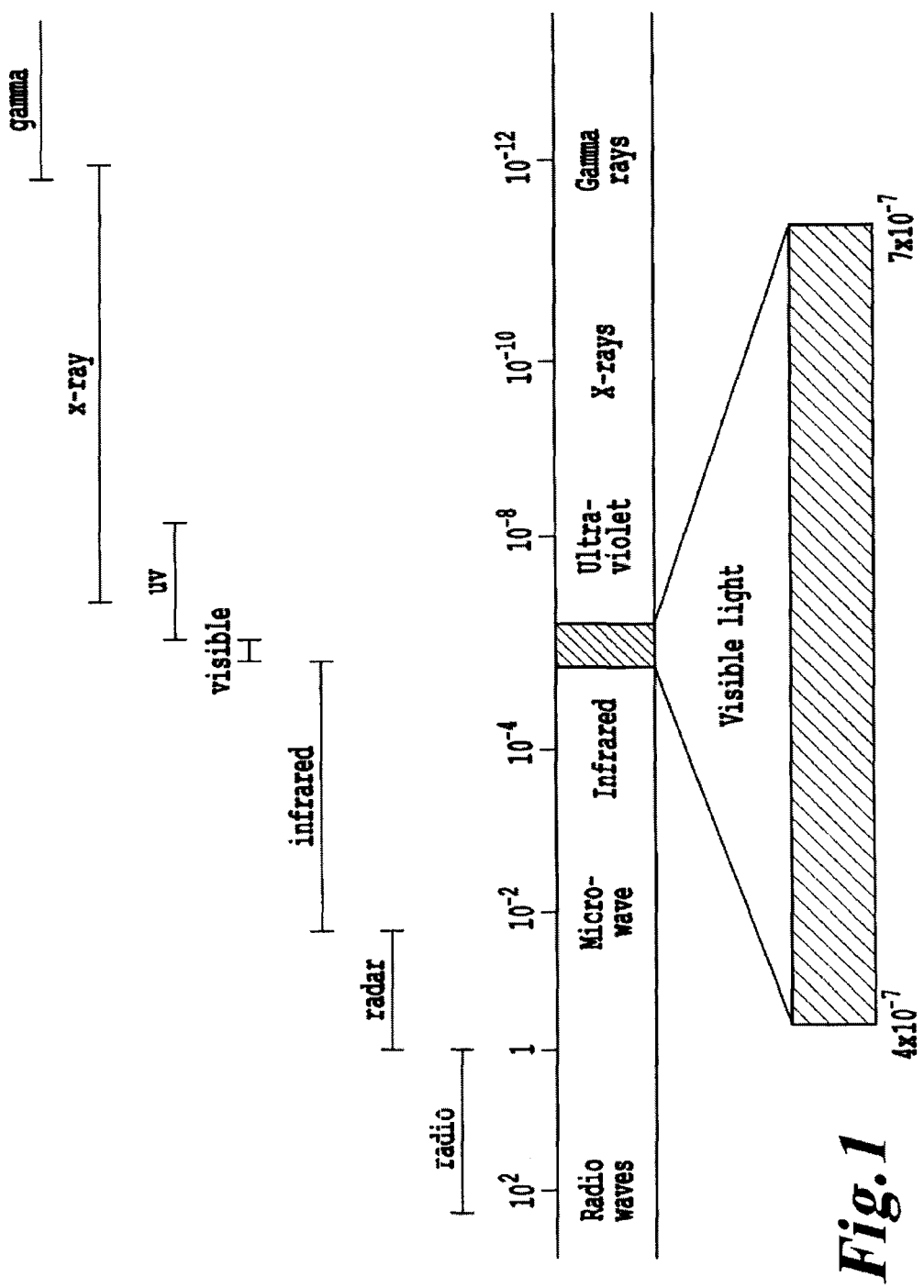
FIG. 1 provides an exemplary electromagnetic spectrum in meters (1 nm equals $10^{-9}$ meters).

The present invention sets forth a novel method of modifying a target structure which mediates or is associated with a biological activity, which includes treating a condition, disorder or disease in a subject, that is effective, specific, and has few side-effects. Those cells suffering from a condition, disorder or disease are referred to herein as the target cells.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

Generally, the present invention provides method for modifying a target structure which mediates or is associated with a biological activity comprising:

applying an initiation energy from at least one source to a target structure in a subject in need of treatment, wherein the initiation energy contacts the target structure and induces a predetermined change in said target structure in situ, wherein said predetermined change modifies the target structure and modulates the biological activity of the target structure.

A further object of the present invention is to provide a method for modifying a target structure which mediates or is associated with a biological activity, comprising:

(1) contacting said target structure with at least one activatable pharmaceutical agent (PA) that is capable of effect: ng a predetermined change in a target structure when activated, optionally in the presence of at least one member selected from the group consisting of energy modulation agents, plasmonics-active agents and combinations thereof; and (2) applying an initiation energy from an initiation energy source to said target structure, wherein the energy modulation agent, if present, upgrades or downgrades the initiation energy to an activation energy capable of activating the at least one activatable pharmaceutical agent;

wherein the plasmonics-active agent, if present, enhances or modifies the applied initiation energy or the activation energy generated by the energy modulation agent, or both; and thus causing the predetermined change to the target structure to occur, wherein said predetermined change modifies the target structure and modulates the biological activity of the target structure.

In a preferred embodiment, the present invention provides methods for the treatment of a condition, disorder or disease, in which an initiation energy source provides an initiation energy that causes the predetermined cellular changes directly to treat target cells within a subject. In one preferred embodiment, the initiation energy source is applied indirectly via an energy modulation agent, preferably in proximity to the target cells. The present invention further provides methods for the treatment of a condition, disorder or disease, in which an initiation energy source provides an initiation energy that activates an activatable pharmaceutical agent to treat target cells within the subject. In one preferred embodiment, the initiation energy source is applied indirectly via an energy modulation agent to the activatable pharmaceutical agent, preferably in proximity to the target cells. The present invention also provides methods for the treatment of a condition, disorder or disease in which an initiation energy source is enhanced or modified by a plasmonic-active agent, such that the enhanced initiation energy activates the pharmaceutical agent in situ.

As noted above, an object of the present invention is to modify a target structure which mediates or is associated with a biological activity, and in a preferred embodiment to treat a condition, disorder or disease, in a subject using photobiomodulation. Exemplary conditions, disorders or diseases may include, but are not limited to, cancer, autoimmune diseases, soft and bone tissue injury, chronic pain, wound healing, nerve regeneration, viral and bacterial infections, fat deposits (liposuction), varicose veins, enlarged prostate, retinal injuries and other ocular diseases, Parkinson's disease, and behavioral, perceptional and cognitive disorders. Exemplary conditions also may include nerve (brain) imaging and stimulation, a direct control of brain cell activity with light, control of cell death (apoptosis), and alteration of cell growth and division.

Accordingly, in one embodiment, the present invention provides methods that are capable of overcoming the shortcomings of the existing methods. In general, a method in accordance with the present invention utilizes an initiation energy from at least one source applied to a target structure in a subject in need of treatment, wherein the initiation energy contacts the target structure and induces a predetermined change in said target structure in situ, thus modifying a target structure which mediates or is associated with a biological activity, preferably treating a condition, disorder or disease. The initiation energy can preferably penetrate completely through the subject and can be applied from a single source or more than one source. Exemplary initiation energy may be UV radiation, visible light, infrared radiation (IR), x-rays, gamma rays, an electron beam, microwaves or radio waves.

In one embodiment, a plasmonics-active agent enhances or modifies the applied initiation energy, such that the enhanced initiation energy causes the predetermined change in said target structure. In a different embodiment, a plasmonics-active agent enhances or modifies the applied initiation energy, such that the enhanced initiation energy is absorbed, intensified or modified by the modulation agent into the energy that effects the predetermined change in said target structure.

In yet another preferred embodiment, a method in accordance with the present invention utilizes the principle of energy transfer to and among molecular agents to control delivery and activation of cellular changes by irradiation such that delivery of the desired effect is more intensified, precise, and effective than the conventional techniques. At least one energy modulation agent can be administered to the subject which adsorbs, intensifies or modifies said initiation energy into an energy that effects a predetermined cellular change in said target structure. The energy modulation agent may be located around, on, or in said target structure. Further, the energy modulation agent can transform a photonic initiation energy into a photonic energy that effects a predetermined change in said target structure. In one preferred embodiment, the energy modulation agent decreases the wavelength of the photonic initiation energy. In another preferred embodiment, the energy modulation agent can increase the wavelength of the photonic initiation energy. In a different embodiment the modulation agent is one or more members selected from a biocompatible fluorescing metal nanoparticle, fluorescing metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

Another object of the present invention is to treat a condition, disorder or disease in a subject using an activatable pharmaceutical agent. Exemplary conditions, disorders or diseases may include, but are not limited to, cancer, autoimmune diseases, cardiac ablasion (e.g., cardiac arrhythmia and atrial fibrillation), photoangioplastic conditions (e.g., de novo atherosclerosis, restinosis), intimal hyperplasia, arteriovenous fistula, macular degeneration, psoriasis, acne, hopecia areata, portwine spots, hair removal, rheumatoid and inflammatory arthrisis, joint conditions, lymph node conditions, and cognitive and behavioral conditions.

Accordingly, in one embodiment, the present invention provides methods utilizing the principle of energy transfer to and among molecular agents to control delivery and activation of pharmaceutically active agents such that delivery of the desired pharmacological effect is more focused, precise, and effective than the conventional techniques.

In yet another preferred embodiment, the initiation energy source is applied directly or indirectly (via a modulation agent) to the activatable pharmaceutical agent, preferably in proximity to the target cells.

Within the context of the present invention, the phrase "applied indirectly" (or variants of this phrase, such as "applying indirectly", "indirectly applies", "indirectly applied", "indirectly applying", etc.), when referring to the application of the initiation energy, means the penetration by the initiation energy into the subject beneath the surface of the subject and to the modulation agent and/or activatable pharmaceutical agent within a subject. In one embodiment, the initiation energy interacts with a previously administered energy modulation agent which then activates the predetermined cellular changes. In another embodiment, the initiation energy interacts with a previously administered energy modulation agent which then activates the activatable pharmaceutical agent. In another embodiment, the initiation energy itself activates the activatable pharmaceutical agent. In either embodiment, the initiation energy source cannot be within line-of-sight of the modulation agent and/or the activatable pharmaceutical agent. By "cannot be within line-of-sight" is meant that if a hypothetical observer were located at the location of the modulation agent or the activatable pharmaceutical agent, that observer would be unable to see the source of the initiation energy.

Although not intending to be bound by any particular theory or be otherwise limited in any way, the following theoretical discussion of scientific principles and definitions are provided to help the reader gain an understanding and appreciation of the present invention.

As used herein, the term "subject" is not intended to be limited to humans, but may also include animals, plants, or any suitable biological organism.

As used herein, the phrase "a disease or condition" refers to a condition, disorder or disease that may include, but are not limited to, cancer, soft and bone tissue injury, chronic pain, wound healing, nerve regeneration, viral and bacterial infections, fat deposits (liposuction), varicose veins, enlarged prostate, retinal injuries and other ocular diseases, Parkinson's disease, and behavioral, perceptional and cognitive disorders. Exemplary conditions also may include nerve (brain) imaging and stimulation, a direct control of brain cell activity with light, control of cell death (apoptosis), and alteration of cell growth and division. Yet other exemplary a condition, disorder or disease may include, but are not limited to, cardiac ablasion (e.g., cardiac arrhythmia and atrial fibrillation), photoangioplastic conditions (e.g., de novo atherosclerosis, restinosis), intimal hyperplasia, arteriovenous fistula, macular degeneration, psoriasis, acne, hopecia areata, portwine spots, hair removal, rheumatoid and inflammatory arthritis, joint conditions, and lymph node conditions.

As used herein, the term "target structure" refers to an eukaryotic cell, prokaryotic cell, a subcellular structure, such as a cell membrane, a nuclear membrane, cell nucleus, nucleic acid, mitochondria, ribosome, or other cellular organelle or component, an extracellular structure, virus or prion, and combinations thereof.

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, regulation of cytochrome c oxidase and flavoproteins, activation of mitochondria, stimulation antioxidant protective pathway, modulation of cell growth and division, alteration of firing pattern of nerves, alteration of redox properties, generation of reactive oxygen species, modulation of the activity, quantity, or number of intracellular components in a cell, modulation of the activity, quantity, or number of extracellular components produced by, excreted by, or associated with a cell, or a combination thereof. Predetermined cellular changes may or may not result in destruction or inactivation of the target structure.

As used herein, an "energy modulation agent" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy. In preferred embodiments, the energy modulation agent receives higher energy (e.g. x-ray) and re-emits in lower energy (e.g. UV-A). Some modulation agents may have a very short energy retention time (on the order of fs, e.g. fluorescent molecules) whereas others may have a very long half-life (on the order of minutes to hours, e.g. luminescent or phosphorescent molecules). Suitable energy modulation agents include, but are not limited to, a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence. Various exemplary uses of these are described below in preferred embodiments.

The modulation agents may further be coupled to a carrier for cellular targeting purposes. For example, a biocompatible molecule, such as a fluorescing metal nanoparticle or fluorescing dye molecule that emits in the UV-A band, may be selected as the energy modulation agent.

The energy modulation agent may be preferably directed to the desired site (e.g. a tumor) by systemic administration to a subject. For example, a UV-A emitting energy modulation agent may be concentrated in the tumor site by physical insertion or by conjugating the UV-A emitting energy modulation agent with a tumor specific carrier, such as a lipid, chitin or chitin-derivative, a chelate or other functionalized carrier that is capable of concentrating the UV-A emitting source in a specific target tumor.

Additionally, the energy modulation agent can be used alone or as a series of two or more energy modulation agents wherein the energy modulation agents provide an energy cascade. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable pharmaceutical agent.

Exemplary energy modulation agents may include, but are not limited to, at least one energy modulation agent selected from the group consisting of a biocompatible fluorescing metal nanoparticle, fluorescing metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

As used herein, an "activatable pharmaceutical agent" is an agent that normally exists in an inactive state in the absence of an activation signal. When the agent is activated by a matching activation signal under activating conditions, it is capable of effecting the desired pharmacological effect on a target cell (i.e. preferably a predetermined cellular change).

Signals that may be used to activate a corresponding agent may include, but are not limited to, photons of specific wavelengths (e.g. x-rays, or visible light), electromagnetic energy (e.g. radio or microwave), thermal energy, acoustic energy, or any combination thereof.

Activation of the agent may be as simple as delivering the signal to the agent or may further premise on a set of activation conditions. For example, in the former case, an activatable pharmaceutical agent, such as a photosensitizer, may be activated by UV-A radiation. Once activated, the agent in its active-state may then directly proceed to effect a cellular change.

Where activation may further premise upon other conditions, mere delivery of the activation signal may not be sufficient to bring about the desired cellular change. For example, a photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors.

Selection of an activatable pharmaceutical agent greatly depends on a number of factors such as the desired cellular change, the desired form of activation, as well as the physical and biochemical constraints that may apply. Exemplary activatable pharmaceutical agents may include, but are not limited to, agents that may be activated by photonic energy, electromagnetic energy, acoustic energy, chemical or enzymatic reactions, thermal energy, or any other suitable activation mechanisms.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

The treatment of the present invention can be by the unique methods described in U.S. application Ser. No. 11/935,655, filed Nov. 6, 2007 (incorporated by reference above), or by a modified version of a conventional treatment such as PDT, but using a plasmonics-active agent to enhance the treatment by modifying or enhancing the applied energy or, in the case of using an energy modulation agent, modifying either the applied energy, the emitted energy from the energy modulation agent, or both.

In one preferred embodiment, the activatable pharmaceutical agent is capable of chemically binding to the DNA or mitochondria at a therapeutically effective amount. In this embodiment, the activatable pharmaceutical agent, preferably a photoactivatable agent, is exposed in situ to an activating energy emitted from an energy modulation agent, which, in turn receives energy from an initiation energy source.

Suitable activatable agents include, but are not limited to, photoactive agents, sono-active agents, thermo-active agents, and radio/microwave-active agents. An activatable agent may be a small molecule; a biological molecule such as a protein, a nucleic acid or lipid; a supramolecular assembly; a nanoparticle; or any other molecular entity having a pharmaceutical activity once activated.

The activatable agent may be derived from a natural or synthetic origin. Any such molecular entity that may be activated by a suitable activation signal source to effect a predetermined cellular change may be advantageously employed in the present invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

Table 1 lists some photoactivatable molecules capable of being photoactivated to induce an auto vaccine effect.

TABLE 1

| | | | | | | | | | | |
|---|---|---|---|---|---|---|---|---|---|---|
| SSET and TTET rate constants for bichromophoric peptides | | | | | | | | | | |
| Compound | $\lambda_{ex}$ (nm) | $E_{SSET}$ | $K_s$ of donor $(S^{-1})$ | $K_{SSET}(S^{-1})$ | $K_{SSET}(S^{-1})$ (Average) | $R_O$ (Å) | R (Å) | $R_{model}$(Å) (Average) | $E_{TTET}$ | $k_{TTET}(S^{-1})$ |
| 1B | 224 | 96.3 | $9.5 \times 10^0$ | $2.44 \times 10^8$ | $1.87 \times 10^8$ | 14.7 | 9 | 9.5 | | |
|  | 266 | 95 | | $1.8 \times 10^8$ | | | | | 2.5 | $5 \times 10^2$ |
|  | 280 | 94 | | $1.36 \times 10^8$ | | | | | | |
| 1A | 224 | 80 | $9.5 \times 10^0$ | $3.8 \times 10^7$ | $3.67 \times 10^7$ | 14.7 | 11.8 | 14.1 | | |
|  | 266 | 79 | | $3.6 \times 10^7$ | | | | | 2 | $3.6 \times 10^2$ |
|  | 280 | 79 | | $3.6 \times 10^7$ | | | | | | |

TABLE 1-continued
SSET and TTET rate constants for bichromophoric peptides
| Compound | $\lambda_{ex}$ (nm) | $E_{SSET}$ | $K_s$ of donor $(S^{-1})$ | $K_{SSET}(S^{-1})$ | $K_{SSET}(S^{-1})$ (Average) | $R_O$ (Å) | $R$ (Å) | $R_{model}$(Å) (Average) | $E_{TTET}$ | $k_{TTET}(S^{-1})$ |
|---|---|---|---|---|---|---|---|---|---|---|
| 2B | 224 | 77 | $9.5 \times 10^0$ | $3.1 \times 10^7$ | $3.9 \times 10^7$ | 14.7 | 11.9 | 5.5 | | |
|  | 266 | 81 |  | $3.9 \times 10^7$ |  |  |  |  | 32 | $9.4 \times 10^3$ |
|  | 280 | 83 |  | $4.7 \times 10^7$ |  |  |  |  |  |  |
| 2A | 224 | 69 | $9.5 \times 10^0$ | $2.1 \times 10^7$ | $3 \times 10^7$ | 14.7 | 12.2 | 8.1 | 74.3 | $5.7 \times 10^4$ |
|  | 266 | 80 |  | $3.7 \times 10^7$ |  |  |  |  |  |  |
|  | 280 | 77 |  | $3.2 \times 10^7$ |  |  |  |  |  |  |
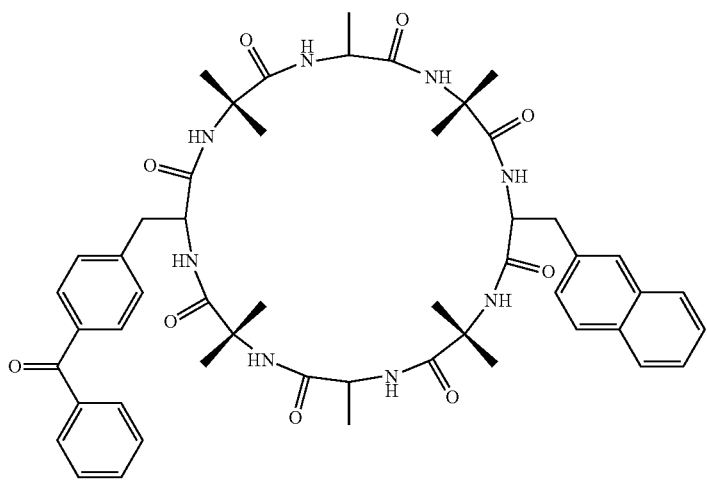
1A
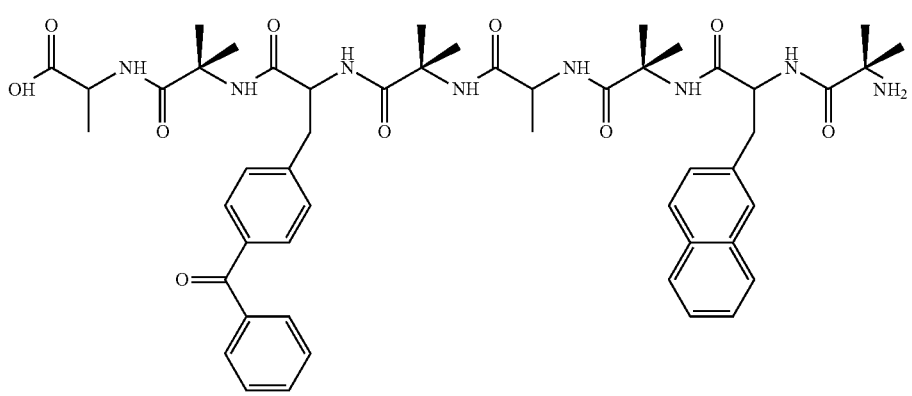
1B -continued

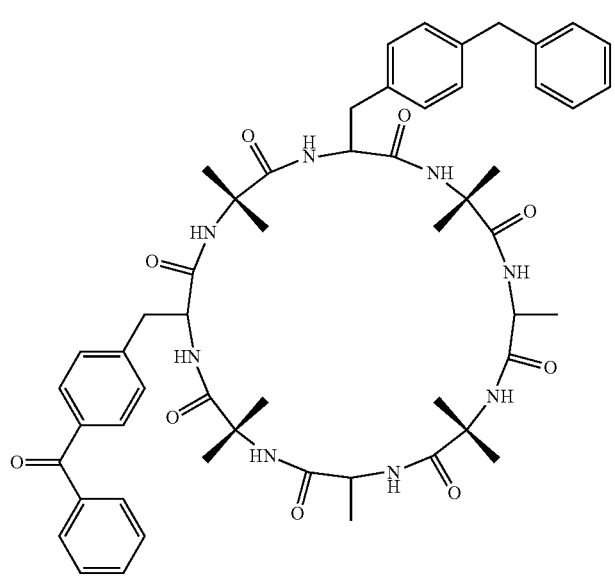

2A

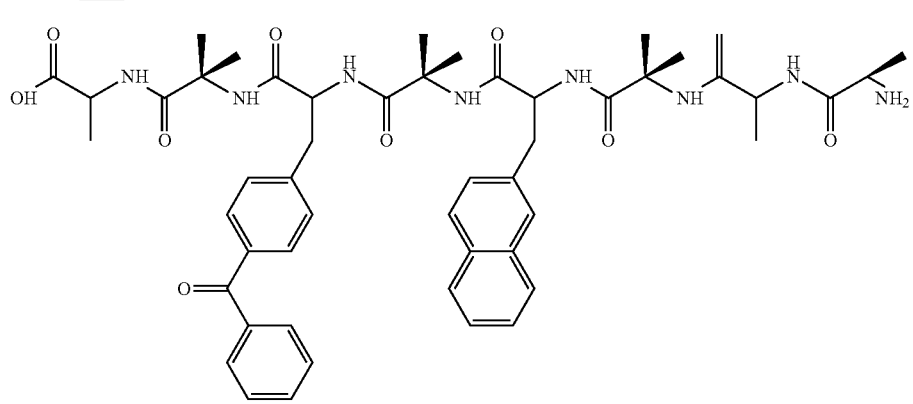

2B

Table 2 lists some additional endogenous photoactivatable molecules.

TABLE 2

Biocompatible, endogenous fluorophore emitters.

| Endogenous Fluorophores | Excitation Max. (nm) | Emission Max. (nm) |
|---|---|---|
| Amino acids: | | |
| Tryptophan | 280 | 350 |
| Tyrosine | 275 | 300 |
| Phenylalanine | 260 | 280 |
| Structural Proteins: | | |
| Collagen | 325, 360 | 400, 405 |
| Elastin | 290, 325 | 340, 400 |
| Enzymes and Coenzymes: | | |
| flavin adenine dinucleotide | 450 | 535 |
| reduced nicotinamide dinucelotide | 290, 351 | 440, 460 |
| reduced nicotinamide dinucleotide phosphate | 336 | 464 |
| Vitamins: | | |
| Vitamins A | 327 | 510 |
| Vitamins K | 335 | 480 |
| Vitamins D | 390 | 480 |

TABLE 2-continued

Biocompatible, endogenous fluorophore emitters.

| Endogenous Fluorophores | Excitation Max. (nm) | Emission Max. (nm) |
|---|---|---|
| Vitamins $B_6$ compounds: | | |
| Pyridoxine | 332, 340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin $B_{12}$ | 275 | 305 |
| Lipids: | | |
| Phospholipids | 436 | 540, 560 |
| Lipofuscin | 340-395 | 540, 430-460 |
| Ceroid | 340-395 | 430-460, 540 |
| Porphyrins | 400-450 | 630, 690 |

FIG. 1 provides an exemplary electromagnetic spectrum in meters (1 nm equals meters).

Although the activatable pharmaceutical agent and the energy modulation agent can be distinct and separate, it will be understood that the two agents need not be independent and separate entities. In fact, the two agents may be associated with each other via a number of different configurations. Where the two agents are independent and separately movable from each other, they generally interact with each other via diffusion and chance encounters within a common surrounding medium. Where the activatable pharmaceutical agent and the energy modulation agent are not separate, they may be combined into one single entity.

The initiation energy source can be any energy source capable of providing energy at a level sufficient to cause cellular changes directly or via a modulation agent which transfer the initiation energy to energy capable of causing the predetermined cellular changes. Also, the initiation energy source can be any energy source capable of providing energy at a level sufficient activate the activatable agent directly, or to provide the energy to a modulation agent with the input needed to emit the activation energy for the activatable agent (indirect activation). Preferable initiation energy sources include, but are not limited to, UV-A lamps or fiber optic lines, a light needle, an endoscope, and a linear accelerator that generates x-ray, gamma-ray, or electron beams. In a preferred embodiment the initiation energy capable of penetrating completely through the subject. Within the context of the present invention, the phrase "capable of penetrating completely through the subject" is used to refer to energy that can penetrate to any depth within the subject to activate the activatable pharmaceutical agent. It is not required that the any of the energy applied actually pass completely through the subject, merely that it be capable of doing so in order to permit penetration to any desired depth to activate the activatable pharmaceutical agent. Exemplary initiation energy sources that are capable of penetrating completely through the subject include, but are not limited to, UV light, visible light, IR radiation, x-rays, gamma rays, electron beams, microwaves and radio waves.

An additional embodiment of the present invention is to provide a method for treatment of a condition, disease or disorder by the in-situ generation of energy in a subject in need thereof, where the energy generated can be used directly to effect a change thereby treating the condition, disease or disorder, or the energy can be used to activate an activatable pharmaceutical agent, which upon activation effects a change thereby treating the condition, disease or disorder. The energy can be generated in-situ by any desired method, including, but not limited to, chemical reaction such as chemiluminescence, or by conversion of an energy applied to the subject externally, which is converted in-situ to a different energy (of lower or higher energy than that applied), through the use of one or more energy modulation agents.

A further embodiment of the present invention combines the treatment of a condition, disease or disorder with the generation of heat in the affected target structure in order to enhance the effect of the treatment. For example, in the treatment of a cell proliferation disorder using a photoactivatable pharmaceutical agent (such as a psoralen or derivative thereof), one can activate the photoactivatable pharmaceutical agent by applying an initiation energy which, directly or indirectly, activates the pharmaceutical agent. As noted elsewhere in the present application, this initiation energy can be of any type, so long as it can be converted to an energy suitable for activating the pharmaceutical compound. In addition to applying this initiation energy, in this embodiment of the present invention, an energy is applied that causes heating of the target structure. In the case of a cell proliferation disorder such as cancer, the heating would increase the proliferation rate of the cancer cells. While this may seem counterintuitive at first, when the cell proliferation disorder is being treated using a DNA intercalation agent, such as psoralen or a derivative thereof, this increase in cell proliferation can actually assist the psoralen in causing apoptosis. In particular, when psoralen becomes intercalated into DNA, apoptosis occurs when the cell goes through its next division cycle. By increasing the rate at which the cells divide, one can use the present invention methods to enhance the onset of apoptosis.

For this embodiment, the heat can be generated in any desired manner. Preferably, the heat can be generated using the application of microwaves or NIR energy to the target structure or by the use of use of nanoparticles of metal or having metal shells. In the nanoparticles embodiment, as is done in tumor thermotherapy, magnetic metal nanoparticles can be targeted to cancer cells using conventional techniques, then used to generate heat by application of a magnetic field to the subject under controlled conditions. (DeNardo S J, DeNardo G L, Natarajan A et al.: Thermal dosimetry predictive of efficacy of 111In-ChL6 NPAMF-induced thermoablative therapy for human breast cancer in mice. J. Nucl. Med. 48(3), 437-444 (2007).)

Alternatively, one can generate heat through the application of NIR to nanoparticles having metal shells which is converted into thermal energy. (Hirsch L R, Stafford R J, Bankson J et al.: Nanoshell-mediated near-infrared thermal therapy of tumors under magnetic resonance guidance. Proc. Natl Acad. Sci. USA 100(23), 13549-13554 (2003)).

In one embodiment, the source of the initiation energy can be a radiowave emitting nanotube, such as those described by K. Jensen, J. Weldon, H. Garcia, and A. Zettl in the Department of Physics at the University of California at Berkeley (see http://socrates.berkeley.edu/~argon/nanoradio/radio.html, the entire contents of which are hereby incorporated by reference). These nanotubes can be administered to the subject, and preferably would be coupled to the activatable pharmaceutical agent or the energy modulation agent, or both, or be located in proximity of a target cell such that upon application of the initiation energy, the nanotubes would accept the initiation energy (preferably radiowaves), then emit radiowaves in close proximity to the activatable pharmaceutical agent, or in close proximity to the energy modulation agent, or to the target cell to then cause the predetermined cellular changes or activation of the activatable pharmaceutical agent. In such an embodiment, the nanotubes would act essentially as a radiowave focusing or amplification device in close proximity to the activatable pharmaceutical agent or energy modulation agent or the target cell.

Alternatively, the energy emitting source may be an energy modulation agent that emits energy in a form suitable for absorption by the transfer agent or a target cell. For example, the initiation energy source may be acoustic energy and one energy modulation agent may be capable of receiving acoustic energy and emitting photonic energy (e.g. sonoluminescent molecules) to be received by another energy modulation agent that is capable of receiving photonic energy. Other examples include transfer agents that receive energy at x-ray wavelength and emit energy at UV wavelength, preferably at UV-A wavelength. As noted above, a plurality of such energy modulation agents may be used to form a cascade to transfer energy from initiation energy source via a series of energy modulation agents to activate the activatable agent or the predetermined cellular change.

Signal transduction schemes as a drug delivery vehicle may be advantageously developed by careful modeling of the cascade events coupled with metabolic pathway knowledge to sequentially or simultaneously cause the predetermined cellular change or activate multiple activatable pharmaceutical agents to achieve multiple-point alterations in cellular function.

Photoactivatable agents may be stimulated by an energy source, such as irradiation, resonance energy transfer, exciton migration, electron injection, or chemical reaction, to an activated energy state that is capable of effecting the predetermined cellular change desired. In a preferred embodiment, the photoactivatable agent, upon activation, binds to DNA or RNA or other structures in a cell. The activated energy state of the agent is capable of causing damage to cells, inducing apoptosis.

One preferred method of treating a condition, disorder or disease mediated by a target structure in a subject comprises:
 (1) administering to the subject at least one activatable pharmaceutical agent that is capable of effecting a predetermined change to the target structure when activated; and
 (2) applying an initiation energy from an initiation energy source to the subject,
 wherein the applied initiation energy activates the activatable agent in situ,
 thus causing the predetermined change to the target structure to occur, wherein said predetermined change treats the condition, disorder, or disease.

Another preferred method for treating a condition, disorder or disease mediated by a target structure in a subject, comprises:
 (1) administering to the subject at least one activatable pharmaceutical agent that is capable of activation by a multi photon absorption event and of effecting a predetermined change in said target when activated; and
 (2) applying an initiation energy from an initiation energy source to the subject,
 wherein the applied initiation energy activates the activatable agent by the multi photon absorption event in situ,
 thus causing the predetermined change to occur, wherein said predetermined change treats the condition, disorder, or disease.

The concept of multi-photon excitation is based on the idea that two or more photons of low energy can excite a fluorophore in a quantum event, resulting in the emission of a fluorescence photon, typically at a higher energy than the two or more excitatory photons. This concept was first described by Maria Göppert-Mayer in her 1931 doctoral dissertation. However, the probability of the near-simultaneous absorption of two or more photons is extremely low. Therefore a high flux of excitation photons is typically required, usually a femtosecond laser. This had limited the range of practical applications for the concept.

Perhaps the most well-known application of the multi-photon excitation concept is the two-photon microscopy pioneered by Winfried Denk in the lab of Watt W. Webb at Cornell University. He combined the idea of two-photon absorption with the use of a laser scanner.

There is an important difference between "sequential" and "simultaneous" two-photon excitation. In sequential two-photon excitation to a higher allowed energy level, the individual energies of both the first photon and the second photon must be appropriate to promote the molecule directly to the second allowed electronic energy level and the third allowed electronic energy level. In contrast, simultaneous two-photon excitation requires only that the combined energy of the first of two photons and the second of two photons be sufficient to promote the molecule to a second allowed electronic energy level.

In two-photon excitation microscopy, an infrared laser beam is focused through an objective lens. The Ti-sapphire laser normally used has a pulse width of approximately 100 femtoseconds and a repetition rate of about 80 MHz, allowing the high photon density and flux required for two photons absorption and is tunable across a wide range of wavelengths. Two-photon technology is patented by Winfried Denk, James Strickler and Watt Webb at Cornell University.

Two known applications are two-photon excited fluorescence (TPEF) and non-linear transmission (NLT). The most commonly used fluorophores have excitation spectra in the 400-500 nm range, whereas the laser used to excite the fluorophores lies in the ~700-1000 nm (infrared) range. If the fluorophore absorbs two infrared photons simultaneously, it will absorb enough energy to be raised into the excited state. The fluorophore will then emit a single photon with a wavelength that depends on the type of fluorophore used (typically in the visible spectrum). Because two photons need to be absorbed to excite a fluorophore, the probability of emission is related to the intensity squared of the excitation beam. Therefore, much more two-photon fluorescence is generated where the laser beam is tightly focused than where it is more diffuse. Effectively, fluorescence is observed in any appreciable amount in the focal volume, resulting in a high degree of rejection of out-of-focus objects. The fluorescence from the sample is then collected by a high-sensitivity detector, such as a photomultiplier tube. This observed light intensity becomes one pixel in the eventual image; the focal point is scanned throughout a desired region of the sample to form all the pixels of the image. Two-photon absorption can be measured by several techniques.

Accordingly, in one aspect, the radiative signal may be of the exact energy required to active the photoactive agent. In this aspect, the radiative energy may be directly targeted at the desired coordinate or region where the photoactive agent is present. The initiation energy source in this embodiment may be, for example, x-rays, gamma rays, an electron beam, microwaves or radio waves.

In another aspect, the radiative signal may be of a lower energy than the excitation energy of the photoactive agent. In this aspect, the radiative signal does not have sufficient energy to activate the photoactive agent in a conventional way. Activation of the photoactive agent may be achieved via an "energy upgrade" mechanism such as the multi-photon mechanism described above. Activation of the photoactive agent may further be mediated by an intermediary energy transformation agent. For example, the radiative energy may first excite a fluorophore that emits a photon at the right energy that excites the photoactive agent. The signal is delivered to the target photoactive agent by way of this intermediary agent. In this way, in addition to energy upgrading (and downgrading, as described below), a signal relay mechanism is also introduced. The initiation energy source may be x-rays, gamma rays, an electron beam, microwaves or radio waves. Also, in one embodiment, if the initiation energy is an infrared energy, the energy activating the activatable agent is not UV or visible light energy. Thus, another preferred method for treating a condition, disease, or disorder mediated by a target structure in a subject, comprises:
 (1) administering to the subject at least one energy modulation agent and at least one activatable pharmaceutical agent that is capable of activation by multi photon absorption and of effecting a predetermined cellular change when activated; and (2) applying an initiation energy from an initiation energy source to the subject, wherein the energy modulation agent upgrades the applied initiation energy to an energy, which then activates the activatable agent by a multi photon absorption event in situ, thus causing the predetermined cellular change to occur, wherein said predetermined cellular change treats the condition, disease or disorder.

In one embodiment, the energy upgrades are obtained via 2, 3, 4, or 5 simultaneous photon absorptions.

Yet another preferred method for treating a condition, diseases, or disorder mediated by a target structure in a subject, comprises:

(1) administering to the subject at least one energy modulation agent and at least one activatable pharmaceutical agent that is capable effecting a predetermined cellular change when activated; and (2) applying an initiation energy from an initiation energy source to the subject, wherein the energy modulation agent upgrades the applied initiation energy to an energy, which then activates the activatable agent in situ, thus causing the predetermined cellular change to occur, wherein said predetermined cellular change treats the condition, disease or disorder.

In yet another aspect, the radiative energy may be of a higher energy than the excitation energy of the photoactive agent. In this aspect, the photoactive agent may be activated via an "energy downgrade" mechanism. In one scenario, via the multi-photon mechanism, two lower energy photons having energy x may be absorbed by an agent to excite the agent from ground state E0 to a higher energy state E2. The agent may then relax down to an intermediate energy state E1 by emitting a photon having an energy y that is equal to the energy gap between E2 and E1, where y is less than x. Other mechanisms of energy downgrade may be mediated by energy transformation agents such as quantum dots, nanotubes, or other agents having suitable photo-radiation properties. The initiation energy source may be, for example, UV radiation, visible light, infrared radiation, x-rays, gamma rays, an electron beam, microwaves or radio waves. Thus, yet another preferred method for treating a condition, disease, or disorder mediated by a target structure in a subject, comprises:

(1) administering to the subject at least one energy modulation agent and at least one activatable pharmaceutical agent that is capable of activation by multi photon absorption and of effecting a predetermined cellular change when activated; and (2) applying an initiation energy from an initiation energy source to the subject, wherein the energy modulation agent downgrades the applied initiation energy to an energy, which then activates the activatable agent by a multi photon absorption event in situ, thus causing the predetermined cellular change to occur, wherein said predetermined cellular change treats the condition, disease, or disorder.

Thus, yet another preferred method for treating a condition, disease, or disorder mediated by a target structure in a subject, comprises:

(1) administering to the subject at least one energy modulation agent and at least one activatable pharmaceutical agent that is capable of effecting a predetermined cellular change when activated; and (2) applying an initiation energy from an initiation energy source to the subject, wherein the energy modulation agent downgrades the applied initiation energy to an energy, which then activates the activatable agent in situ, thus causing the predetermined cellular change to occur, wherein said predetermined cellular change treats the condition, disorder or disease.

In a further preferred embodiment, the present invention provides a method for treating a condition, disorder or disease mediated by a target structure in a subject, comprising:

(1) administering to the subject an activatable pharmaceutical agent that is capable of effecting a predetermined change in said target structure when activated; and (2) applying an initiation energy from an initiation energy source to the subject, wherein the initiation energy applied and activatable pharmaceutical agent upon activation produce insufficient singlet oxygen in the subject to produce cell lysis, and wherein the initiation energy activates the activatable pharmaceutical agent in situ, thus causing the predetermined change to occur via said target structure, wherein said predetermined change targets the condition, disorder or disease.

In a different preferred embodiment, the present invention provides a method for treating a condition, disorder or disease mediated by a target structure in a subject, comprising:

(1) administering to the subject an activatable pharmaceutical agent that is capable of activation by multi photon absorption and effecting a predetermined change in said target structure when activated; and (2) applying an initiation energy from an initiation energy source to the subject, wherein the initiation energy applied and activatable pharmaceutical agent upon activation produce insufficient singlet oxygen in the subject to produce cell lysis, and wherein the initiation energy activates the activatable pharmaceutical agent by the multi photon absorption event in situ, thus causing the predetermined change to occur via said target structure, wherein said predetermined change targets the condition, disorder or disease.

Work in the area of photodynamic therapy has shown that the amount of singlet oxygen required to cause cell lysis, and thus cell death, is $0.32 \times 10^{-3}$ mol/liter or more, or $10^9$ singlet oxygen molecules/cell or more. In one preferred embodiment, it is preferable to avoid production of an amount of singlet oxygen that would cause cell lysis, due to its indiscriminate nature of attack, lysing both target cells and healthy cells. Accordingly, it is preferred in one preferred embodiment that the level of singlet oxygen production caused by the initiation energy used or activatable pharmaceutical agent upon activation be less than level needed to cause cell lysis.

One advantage is that multiple wavelengths of emitted radiation may be used to selectively stimulate one or more photoactivatable agents or energy modulation agents capable of stimulating the one or more photoactivatable agents. The energy modulation agent is preferably stimulated at a wavelength and energy that causes little or no damage to healthy cells, with the energy from one or more energy modulation agents being transferred, such as by Foerster Resonance Energy Transfer, to the photoactivatable agents that damage the cell and cause the onset of the desired cellular change, e.g., apoptosis of the cells.

Another advantage is that side effects can be greatly reduced by limiting the production of free radicals, singlet oxygen, hydroxides and other highly reactive groups that are known to damage healthy cells. Furthermore, additional additives, such as antioxidants, may be used to further reduce undesired effects of irradiation.

Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a photoactivatable molecule.

Alternatively, one can administer the initiation energy source to the subject. Within the context of the present invention, the administering of the initiation energy source means the administration of an agent, that itself produces the initiation energy, in a manner that permits the agent to arrive at the target cell within the subject without being surgically inserted into the subject. The administration can take any form, including, but not limited to, oral, intravenous, intraperitoneal, inhalation, etc. Further, the initiation energy source in this embodiment can be in any form, including, but not limited to, tablet, powder, liquid solution, liquid suspension, liquid dispersion, gas or vapor, etc. In this embodiment, the initiation energy source includes, but is not limited to, chemical energy sources, nanoemitters, nanochips, and other nanomachines that produce and emit energy of a desired frequency. Recent advances in nanotechnology have provided examples of various devices that are nanoscale and produce or emit energy, such as the Molecular Switch (or Mol-Switch) work by Dr. Keith Firman of the EC Research and Development Project, or the work of Cornell et al. (1997) who describe the construction of nanomachines based around ion-channel switches only 1.5 nm in size, which use ion channels formed in an artificial membrane by two gramicidin molecules: one in the lower layer of the membrane attached to a gold electrode and one in the upper layer tethered to biological receptors such as antibodies or nucleotides. When the receptor captures a target molecule or cell, the ion channel is broken, its conductivity drops, and the biochemical signal is converted into an electrical signal. These nanodevices could also be coupled with the present invention to provide targeting of the target cell, to deliver the initiation energy source directly at the desired site.

In another embodiment, the present invention includes the administration of a source of chemical energy such as chemiluminescence, phosphorescence or bioluminescence. The source of chemical energy can be a chemical reaction between two or more compounds, or can be induced by activating a chemiluminescent, phosphorescent or bioluminescent compound with an appropriate activation energy, either outside the subject or inside the subject, with the chemiluminescence, phosphorescence or bioluminescence being allowed to activate the activatable pharmaceutical agent in vivo after administration. In one embodiment, the activatable pharmaceutical agent and the source of chemical energy can be administered. The administration can be performed sequentially in any order or simultaneously. In the case of certain sources of such chemical energy, the administration of the chemical energy source can be performed after activation outside the subject, with the lifetime of the emission of the energy being up to several hours for certain types of phosphorescent materials for example. There are no known previous efforts to use resonance energy transfer of any kind to activate an intercalator to bind DNA.

Yet another example is that nanoparticles or nanoclusters of certain atoms may be introduced such that are capable of resonance energy transfer over comparatively large distances, such as greater than one nanometer, more preferably greater than five nanometers, even more preferably at least 10 nanometers. Functionally, resonance energy transfer may have a large enough "Foerster" distance ($R_0$), such that nanoparticles in one part of a cell are capable of stimulating activation of photoactivatable agents disposed in a distant portion of the cell, so long as the distance does not greatly exceed $R_0$. For example, gold nanospheres having a size of 5 atoms of gold have been shown to have an emission band in the ultraviolet range, recently.

In one embodiment, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death, even if exposed to photoactivated agents, provided that such photoactivated agents degenerate from the excited state to a lower energy state prior to binding, mitosis or other mechanisms for creating damage to the cells of a substantial fraction of the healthy stem cells. Thus, an auto-immune response may not be induced.

Alternatively, a blocking agent may be used that prevents or reduces damage to stem cells or healthy cells, selectively, which would otherwise be impaired. The blocking agent is selected or is administered such that the blocking agent does not impart a similar benefit to malignant cells, for example.

In one embodiment, stem cells are targeted, specifically, for destruction with the intention of replacing the stem cells with a donor cell line or previously stored, healthy cells of the patient. In this case, no blocking agent is used. Instead, a carrier or photosensitizer is used that specifically targets the stem cells.

Any of the photoactivatable agents may be exposed to an excitation energy source implanted in a subject preferably near a target site. The photoactive agent may be directed to a receptor site by a carrier having a strong affinity for the receptor site. Within the context of the present invention, a "strong affinity" is preferably an affinity having an equilibrium dissociation constant, $K_j$, at least in the nanomolar, nM, range or higher. Preferably, the carrier may be a polypeptide and may form a covalent bond with a photoactive agent, for example. The polypeptide may be an insulin, interleukin, thymopoietin or transferrin, for example. Alternatively, a photoactive agent may have a strong affinity for the target cell without binding to a carrier.

A receptor site may be any of the following: nucleic acids of nucleated blood cells, molecule receptor sites of nucleated blood cells, the antigenic sites on nucleated blood cells, epitopes, or other sites where photoactive agents are capable of destroying a targeted cell.

In one embodiment, thin fiber optic lines are inserted in the subject and laser light is used to photoactivate the agents. In another embodiment, a plurality of sources for supplying electromagnetic radiation energy or energy transfer are provided by one or more molecules administered to a patient. The molecules may emit stimulating radiation in the correct band of wavelength to stimulate the target structure directly or to simulate the photoactivatable agents, or the molecules may transfer energy by a resonance energy transfer or other mechanism directly to he target structure or the photoactivatable agent or indirectly by a cascade effect via other molecular interactions.

The phenomenon of ultra weak emission from cellular systems has been a topic of various inquiries since the 1900s. This topic can be traced back to the early investigations of the Russian biologist Gurwitsch Alexander G. Gurwitsch more than seventy years ago, who speculated that ultraweak photon emission transmit information in cells [A. G. Gurwitsch, S. S. Grabje, and S. Salkind, "Die Natur des spezifischen Erregers der Zellteilung," *Arch. Entwicklungsmech. Org.* 100, 11-40, 1923].

In the 1970s, this area of research was investigated by a number of investigators. The presence of biological radiation from a variety of cells was later investigated by several research groups in Europe and Japan using low-noise, sensitive photon-counting detection systems [B. Ruth and F.-A. Popp, "Experimentelle Untersuchungen zur ultraschwachen Photonenemission biologischer Systeme," *Z. Naturforsch., A: Phys. Sci.* 31c, 741-745, 1976; T. I. Quickenden and S. S. Que-Hee, "The spectral distribution of the luminescence emitted during growth of the yeast *Saccharomyces cerevisiae* and its relationship to mitogenetic radiation," *Photochem. Photobiol.* 23, 201-204, 1976; H. Inaba, Y. Shimizu, Y. Tsuji, and A. Yamagishi, "Photon counting spectral analysing system of extra-weak chemi- and bioluminescence for biochemical applications," *Photochem. Photobiol.* 30, 169-175, 1979]. Popp and coworkers suggested the evidence of some 'informational character' associated with the ultra-weak photon emission from biological systems, often referred by Popp as "bio-photons". Other studies reported ultra-weak photon emission from various species including plant, and animals cells [H. J. Niggli, C. Scaletta, Y. Yan, F.-A. Popp, and L. A. Applegate, "Ultraweak photon emission in assessing bone growth factor efficiency using fibroblastic differentiation," *J. Photochem. Photobiol., B,* 64, 62-68, 2001;]. Results of experiments of UV-irradiated skin fibroblasts indicated that repair deficient xeroderma pigmentosum cells show an efficient increase of ultraweak photon emission in contrast to normal cells. [H. J. Niggli, "Artificial sunlight irradiation induces ultraweak photon emission in human skin fibroblasts," *J. Photochem. Photobiol., B* 18, 281-285 (1993)].

A delayed luminescence emission was also observed in biological systems [F.-A. Popp and Y. Yan, "Delayed luminescence of biological systems in terms of coherent states," *Phys. Lett. A* 293, 93-97 (2002); A. Scordino, A. Triglia, F. Musumeci, F. Grasso, and Z. Rajfur, "Influence of the presence of Atrazine in water on in-vivo delayed luminescence of acetabularium acetabulum," *J. Photochem. Photobiol., B,* 32, 11-17 (1996); This delayed luminescence was used in quality control of vegetable products [A. Triglia, G. La Malfa, F. Musumeci, C. Leonardi, and A. Scordino, "Delayed luminescence as an indicator of tomato fruit quality," *J. Food. Sci.* 63, 512-515 (1998)] or for assessing the quality or quality changes of biological tissues [Yu Yan, Fritz-Albert Popp *, Sibylle Sigrist, Daniel Schlesinger, Andreas Dolf, Zhongchen Yan, Sophie Cohen, Amodsen Chotia, "Further analysis of delayed luminescence of plants", *Journal of Photochemistry and Photobiology B: Biology* 78, 235-244 (2005)].

It was reported that UV excitation can further enhance the ultra-weak emission and a method for detecting UV-A-laser-induced ultra-weak photon emission was used to evaluate differences between cancer and normal cells. [H. J. Niggli et al, Laser-ultraviolet-A-induced ultraweak photon emission in mammalian cells, *Journal of Biomedical Optics* 10(2), 024006 (2005)].

Accordingly, in one embodiment of the present invention, upon applying an initiation energy from at least one source to a target structure in a subject in need of treatment, the initiation energy contacts the target structure and induces a predetermined change in said target structure in situ, wherein the predetermined change is the enhancement of energy emission from the target, which then mediates, initiates or enhances a biological activity of other target structures in the subject, or of a second type of target structure (e.g., a different cell type).

In another embodiment, the patient's own cells are removed and genetically modified to provide photonic emissions. For example, tumor or healthy cells may be removed, genetically modified to induce bioluminescence and may be reinserted at the site of the disease or condition to be treated. The modified, bioluminescent cells may be further modified to prevent further division of the cells or division of the cells only so long as a regulating agent is present.

In a further embodiment, a biocompatible emitting source, such as a fluorescing metal nanoparticle or fluorescing dye molecule, is selected that emits in the UV-A band. The UV-A emitting source is directed to the site of a disease or condition. The UV-A emitting source may be directed to the site of the disease or condition by systemically administering the UV-A emitting source. Preferably, the UV-A emitting source is concentrated in the target site, such as by physical insertion or by conjugating the UV-A emitting molecule with a specific carrier that is capable of concentrating the UV-A emitting source in a specific target structure, as is known in the art.

In one preferred embodiment, the UV-A emitting source is a gold nanoparticle comprising a cluster of 5 gold atoms, such as a water soluble quantum dot encapsulated by polyamidoamine dendrimers. The gold atom clusters may be produced through a slow reduction of gold salts (e.g. $HAuCl_4$ or $AuBr_3$) or other encapsulating amines, for example. One advantage of such a gold nanoparticle is the increased Foerster distance (i.e. $R_o$), which may be greater than 100 angstroms. The equation for determining the Foerster distance is substantially different from that for molecular fluorescence, which is limited to use at distances less than 100 angstroms. It is believed that the gold nanoparticles are governed by nanoparticle surface to dipole equations with a $1/R^4$ distance dependence rather than a $1/R^6$ distance dependence. For example, this permits cytoplasmic to nuclear energy transfer between metal nanoparticles and a photoactivatable molecule, such as a psoralen and more preferably an 8-methoxypsoralen (8-MOP) administered orally to a patient, which is known to be safe and effective at inducing an apoptosis of leukocytes.

In another embodiment, a UV- or light-emitting luciferase is selected as the emitting source for exciting a photoactivatable agent. A luciferase may be combined with ATP or another molecule, which may then be oxygenated with additional molecules to stimulate light emission at a desired wavelength. Alternatively, a phosphorescent emitting source may be used. One advantage of a phosphorescent emitting source is that the phosphorescent emitting molecules or other source may be electroactivated or photoactivated prior to insertion into a target site either by systemic administration or direct insertion into the region of the target site. Alternatively, some of these materials can be activated, with the energy being "stored" in the activated material, until emission is stimulated by application of another energy. For example, see the discussion of U.S. Pat. No. 4,705,952 below with respect to infrared-triggered phosphors.

Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

Among various materials, luminescent nanoparticles have attracted increasing technological and industrial interest. In the context of the present invention, nanoparticle refers to a particle having a size less than one micron. While the description of the invention describes specific examples using nanoparticles, the present invention in many embodiments is not limited to particles having a size less than one micron. However, in many of the embodiments, the size range of having a size less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

U.S. Pat. No. 4,705,952 (the contents of which are hereby incorporated herein by reference) describes an infrared-triggered phosphor that stored energy in the form of visible light of a first wavelength and released energy in the form of visible light of a second wavelength when triggered by infrared light. In some cases, U.S. Pat. No. 4,705,952 describes that "the upconversion continues for as long as several days before a new short recharge is required." The phosphors in U.S. Pat. No. 4,705,952 were compositions of alkaline earth metal sulfides. rare earth dopants, and fusible salts. The phosphors in U.S. Pat. No. 4,705,952 were more specifically phosphors made from strontium sulfide, barium sulfide and mixtures thereof including a dopant from the rare earth series and europium oxide, and mixtures thereof; and including a fusible salt of fluorides, chlorides, bromides, and iodides of lithium, sodium, potassium, cesium, magnesium, calcium, strontium, and barium, and mixtures thereof. The materials described in U.S. Pat. No. 4,705,952 are useful in various embodiments of the invention.

In some cases, U.S. Pat. No. 4,705,952 describes that "the storage times become extremely long, on the order of years." The material is thus adapted to receive infrared photons and to emit higher energy photons in a close to 1:1 relation. With storage times this long, these infrared-triggered phosphors can be used in various embodiments of the present invention as a viable mechanism where commercial IR lasers are used to activate phosphorescence in a medium, thereby in a patient generating visible or ultraviolet light.

In another embodiment, a combined electromagnetic energy harvester molecule is designed, such as the combined light harvester disclosed in J. Am. Chem. Soc. 2005, 127, 9760-9768, the entire contents of which are hereby incorporated by reference. By combining a group of fluorescent molecules in a molecular structure, a resonance energy transfer cascade may be used to harvest a wide band of electromagnetic radiation resulting in emission of a narrow band of fluorescent energy. By pairing a combined energy harvester with a photoactivatable molecule, a further energy resonance transfer excites the photoactivatable molecule, when the photoactivatable molecule is nearby stimulated combined energy harvester molecules. Another example of a harvester molecule is disclosed in FIG. 4 of "Singlet-Singlet and Triplet-Triplet Energy Transfer in Bichromophoric Cyclic Peptides," M. S. Thesis by M. O. Guler, Worcester Polytechnic Institute, May 18, 2002, which is incorporated herein by reference.

In another embodiment, a Stokes shift of an emitting source or a series of emitting sources arranged in a cascade is selected to convert a shorter wavelength energy, such as X-rays, to a longer wavelength fluorescence emission such a optical or UV-A, which is used to stimulate a photoactivatable molecule at the location of the target structure. Preferably, the photoactivatable molecule is selected to cause the predetermined change in target structure without causing substantial harm to normal, healthy cells.

In an additional embodiment, the photoactivatable agent can be a photocaged complex having an active agent contained within a photocage. The active agent is bulked up with other molecules that prevent it from binding to specific targets, thus masking its activity. When the photocage complex is photoactivated, the bulk falls off, exposing the active agent. In such a photocage complex, the photocage molecules can be photoactive (i.e. when photoactivated, they are caused to dissociate from the photocage complex, thus exposing the active agent within), or the active agent can be the photoactivatable agent (which when photoactivated causes the photocage to fall off), or both the photocage and the active agent are photoactivated, with the same or different wavelengths. For example, a toxic chemotherapeutic agent can be photocaged, which will reduce the systemic toxicity when delivered. Once the agent is concentrated in the tumor, the agent is irradiated with an activation energy. This causes the "cage" to fall off, leaving a cytotoxic agent in the tumor cell. Suitable photocages include those disclosed by Young and Deiters in "Photochemical Control of Biological Processes", *Org. Biomol. Chem.*, 5, pp. 999-1005 (2007) and "Photochemical Hammerhead Ribozyme Activation", *Bioorganic & Medicinal Chemistry Letters*, 16(10), pp. 2658-2661 (2006), the contents of which are hereby incorporated by reference.

In one preferred embodiment, the use of light for uncaging a compound or agent is used for elucidation of neuron functions and imaging, for example, two-photon glutamine uncaging (Harvey C D, et al., Nature, 450:1195-1202 (2007); Eder M, et al., Rev. Neurosci., 15:167-183 (2004)). Other signaling molecules can be released by UV light stimulation, e.g., GABA, secondary messengers (e.g., $Ca^{2+}$ and $Mg^{2+}$), carbachol, capsaicin, and ATP (Zhang F., et al., 2006). Chemical modifications of ion channels and receptors may be carried out to render them light-responsive. $Ca^{2+}$ is involved in controlling fertilization, differentiation, proliferation, apoptosis, synaptic plasticity, memory, and developing axons. In yet another preferred embodiment, $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Genetic targeting allows morphologically and electrophysipologically characterization of genetically defined cell populations. Accordingly, in an additional embodiment, a light-sensitive protein is introduced into cells or live subjects via a number of techniques including electroporation, DNA microinjection, viral delivery, liposomal transfection, creation of transgenic lines and calcium-phosphate precipitation. For example, lentiviral technology provides a convenient combination a conventional combination of stable long-term expression, ease of high-titer vector production and low immunogenicity. The light-sensitive protein may be, for example, channelrhodopsin-2 (ChR2) and chloride pump ha Lorhodopsin (NpHR). The light protein encoding gene(s) along with a cell-specific promoter can be incorporated into the lentiviral vector or other vector providing delivery of the light-sensitive protein encoding gene into a target cell. ChR2 containing a light sensor and a cation channel, provides electrical stimulation of appropriate speed and magnitude to activate neuronal spike firing, when the cells harboring Ch2R are pulsed with light.

In one embodiment, a lanthanide chelate capable of intense luminescence is used. For example, a lanthanide chelator may be covalently joined to a coumarin or coumarin derivative or a quinolone or quinolone-derivative sensitizer. Sensitizers may be a 2- or 4-quinolone, a 2- or 4-coumarin, or derivatives or combinations of these examples. A carbostyril 124 (7-amino-4-methyl-2-quinolone), a coumarin 120 (7-amino-4-methyl-2-coumarin), a coumarin 124 (7-amino-4-(trifluoromethyl)-2-coumarin), aminoethyltrimethylpsoralen or other similar sensitizer may be used. Chelates may be selected to form high affinity complexes with lanthanides, such as terbium or europium, through chelator groups, such as DTPA. Such chelates may be coupled to any of a wide variety of well known probes or carriers, and may be used for resonance energy transfer to a psoralen or psoralen-derivative, such as 8-MOP, or other photoactive molecules capable of binding DNA. In one alternative example, the lanthanide chelate is localized at the site of the disease using an appropriate carrier molecule, particle or polymer, and a source of electromagnetic energy is introduced by minimally invasive procedures to irradiate the target structure, after exposure to the lanthanide chelate and a photoactive molecule.

In another embodiment, a biocompatible, endogenous fluorophore emitter is selected to stimulate resonance energy transfer to a photoactivatable molecule. A biocompatible emitter with an emission maxima within the absorption range of the biocompatible, endogenous fluorophore emitter may be selected to stimulate an excited state in fluorophore emitter. One or more halogen atoms may be added to any cyclic ring structure capable of intercalation between the stacked nucleotide bases in a nucleic acid (either DNA or RNA) to confer new photoactive properties to the intercalator. Any intercalating molecule (psoralens, coumarins, or other polycyclic ring structures) may be selectively modified by halogenation or addition of non-hydrogen bonding ionic substituents to impart advantages in its reaction photochemistry and its competitive binding affinity for nucleic acids over cell membranes or charged proteins, as is known in the art.

Skin photosensitivity is a major toxicity of photosensitizers. Severe sunburn occurs if skin is exposed to direct sunlight for even a few minutes. Early murine research hinted at a vigorous and long term stimulation of immune response; however, actual clinical testing has failed to achieve the early promises of photodynamic therapies. The early photosensitizers for photodynamic therapies targeted type II responses, which created singlet oxygen when photoactivated in the presence of oxygen. The singlet oxygen caused cellular necrosis and was associated with inflammation and an immune response. Some additional photosensitizers have been developed to induce type I responses, directly damaging cellular structures.

Porfimer sodium (Photofrin; QLT Therapeutics, Vancouver, BC, Canada), is a partially purified preparation of hematoporphyrin derivative (HpD). Photofrin has been approved by the US Food and Drug Administration for the treatment of obstructing esophageal cancer, microinvasive endobronchial non-small cell lung cancer, and obstructing endobronchial non-small cell lung cancer. Photofrin is activated with 630 nm, which has a tissue penetration of approximately 2 to 5 mm. Photofrin has a relatively long duration of skin photosensitivity (approximately 4 to 6 weeks).

Tetra (m-hydroxyphenyl) chlorin (Foscan; Scotia Pharmaceuticals, Stirling, UK), is a synthetic chlorine compound that is activated by 652 nm light. Clinical studies have demonstrated a tissue effect of up to 10 mm with Foscan and 652 nm light. Foscan is more selectively a photosensitizer in tumors than normal tissues, and requires a comparatively short light activation time. A recommended dose of 0.1 mg/kg is comparatively low and comparatively low doses of light may be used. Nevertheless, duration of skin photosensitivity is reasonable (approximately 2 weeks). However, Foscan induces a comparatively high yield of singlet oxygen, which may be the primary mechanism of DNA damage for this molecule.

Figure 2A:
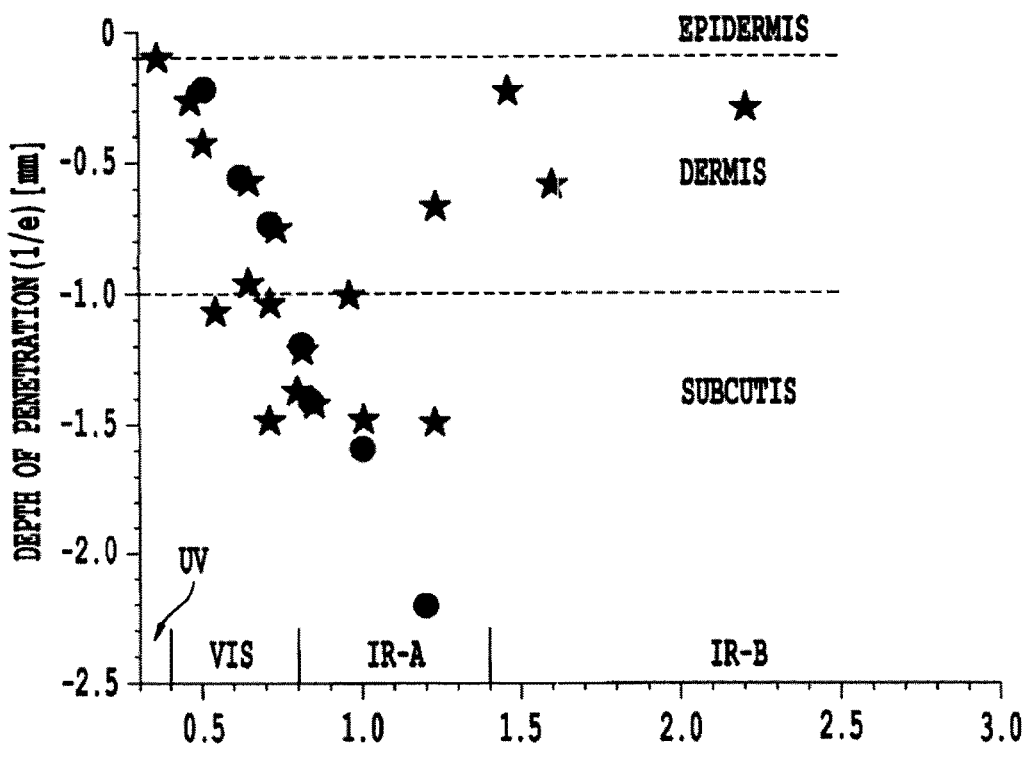
FIG. 2A and FIG. 2B are graphical representations of the depth of penetration of various wavelengths of energy into living tissue
Figure 2B:
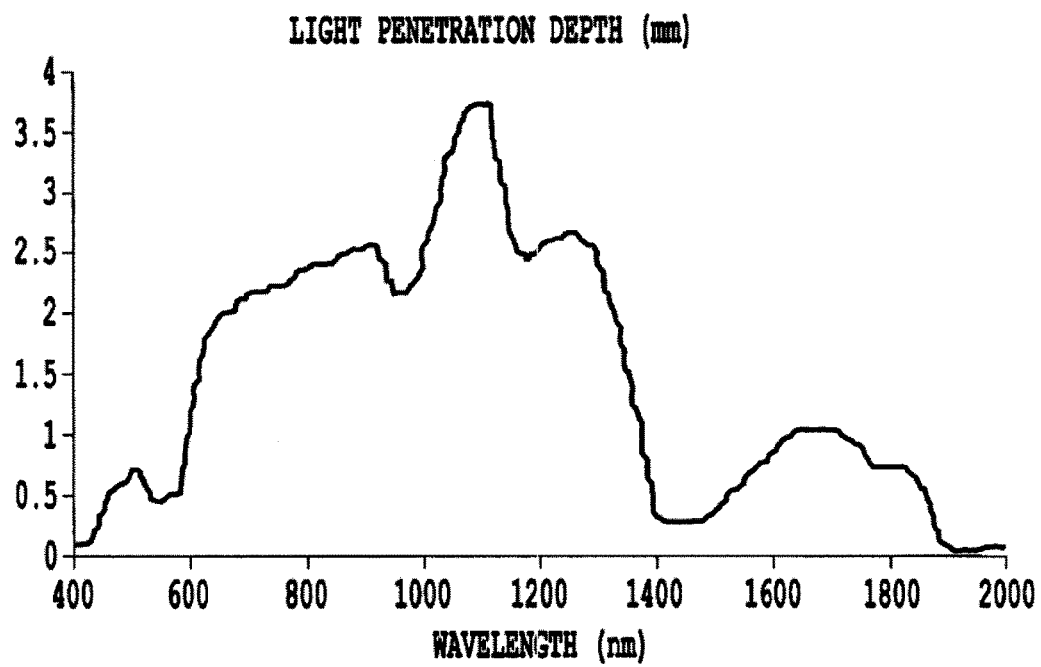

Motexafin lutetium (Lutetium texaphyrin) is activated by light in the near infared region (732 nm). Absorption at this wavelength has the advantage of potentially deeper penetration into tissues, compared with the amount of light used to activate other photosensitizers (FIGS. 2A and 2B). Lutetium texaphyrin also has one of the greatest reported selectivities for tumors compared to selectivities of normal tissues. Young S W, et al.: Lutetium texaphyrin (PCI-0123) a near-infrared, water-soluble photosensitizer. Photochem Photobiol 1996, 63:892-897. In addition, its clinical use is associated with a shorter duration of skin photosensitivity (24 to 48 hours). Lutetium texaphyrin has been evaluated for metastatic skin cancers. It is currently under investigation for treatment of recurrent breast cancer and for locally recurrent prostate cancer. The high selectivity for tumors promises improved results in clinical trials.

In general, the approach may be used with any source for the excitation of higher electronic energy states, such as electrical, chemical and/or radiation, individually or combined into a system for activating an activatable molecule. The process may be a photopheresis process or may be similar to photophoresis. While photophoresis is generally thought to be limited to photonic excitation, such as by UV-light, other forms of radiation may be used as a part of a system to activate an activatable molecule. Radiation includes ionizing radiation which is high energy radiation, such as an X-ray or a gamma ray, which interacts to produce ion pairs in matter. Radiation also includes high linear energy transfer irradiation, low linear energy transfer irradiation, alpha rays, beta rays, neutron beams, accelerated electron beams, and ultraviolet rays. Radiation also includes proton, photon and fission-spectrum neutrons. Higher energy ionizing radiation may be combined with chemical processes to produce energy states favorable for resonance energy transfer, for example. Other combinations and variations of these sources of excitation energy may be combined as is known in the art, in order to stimulate the activation of an activatable molecule, such as 8-MOP. In one example, ionizing radiation is directed at a solid tumor and stimulates, directly or indirectly, activation of 8-MOP, as well as directly damaging the DNA of malignant tumor cells. In this example, either the effect of ionizing radiation or the photophoresis-like activation of 8-MOP may be thought of as an adjuvant therapy to the other.

In one embodiment, the present invention provides a method for treating a condition, disease or disorder mediated by a target structure in a subject, comprising:
(1) administering to the subject an activatable pharmaceutical agent that is capable of effecting a predetermined change when activated; and
(2) applying an initiation energy from an initiation energy source to the subject,
wherein the initiation energy source is a source of energy capable of penetrating completely through the subject, and wherein the applying activates the activatable agent in situ,
thus causing the predetermined change to occur, wherein occurrence of the predetermined change in the target structure causes an increase in rate or decrease in rate of cell division and/or growth to treat the condition, disease or disorder.

In a further embodiment, the present invention provides a method for treating a condition, disease or disorder mediated by a target structure in a subject, comprising:
(1) administering to the subject one or more energy modulation agents and an activatable pharmaceutical agent that is capable of effecting a predetermined change in the target structure when activated; and
(2) applying an initiation energy from an initiation energy source to the subject,
wherein the one or more energy modulation a agents convert the initiation energy applied to UV-A or visible energy, which then activates the activatable agent in situ,
thus causing the predetermined change to occur, wherein occurrence of the predetermined change causes an increase in rate or decrease in rate of cell division and/or growth to treat the condition, disease or disorder.

In a different embodiment, the activatable pharmaceutical agent can be activated by a single or multiphoton absorption event.

Work in the area of photodynamic therapy has shown that the amount of singlet oxygen required to cause cell lysis, and thus cell death, is $0.32 \times 10^{-3}$ mol/liter or more, or $10^9$ singlet oxygen molecules/cell or more. However, in the present invention, it is most preferable to avoid production of an amount of singlet oxygen that would cause cell lysis, due to its indiscriminate nature of attack, lysing both target cells and healthy cells. Accordingly, it is most preferred in the present invention that the level of singlet oxygen production caused by the initiation energy used or activatable pharmaceutical agent upon activation be less than level needed to cause cell lysis.

In yet another embodiment, the activatable pharmaceutical agent, preferably a photoactive agent, is directed to a receptor site by a carrier having a strong affinity for the receptor site. The carrier may be a polypeptide and may form a covalent bond with a photo active agent, for example. The polypeptide may be an insulin, interleukin, thymopoietin or transferrin, for example. Alternatively, a photoactive pharmaceutical agent may have a strong affinity for the target cell without a binding to a carrier.

For example, a treatment may be applied that acts to slow or pause mitosis. Such a treatment is capable of slowing the division of rapidly dividing healthy cells or stem cells without pausing mitosis of cancerous cells. Thus, the difference in growth rate between the non-target cells and target cells are further differentiated to enhance the effectiveness of the methods of the present invention.

In a further embodiment, methods in accordance with the present invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

In another aspect, the present invention also provides methods for producing an autovaccine, including: (1) providing a population of targeted cells; (2) treating the cells ex vivo with a psoralen or a derivative thereof; (3) activating the psoralen with an initiation energy source to induce a predetermined change in a target structure in the population of the target cells; and (4) returning the treated cells back to the host to induce an autovaccine effect against the targeted cell, wherein the treated cells cause an autovaccine effect.

In a different embodiment, a method for generating an autovaccine for a subject, comprises:
(1) providing a population of target cells;
(2) treating the target cells ex vivo in an environment separate and isolated from the subject with an activatable pharmaceutical agent capable of activation by a multi photon absorption event;
(3) exposing the treated target cells to an energy source;
(4) activating the activatable pharmaceutical agent with the energy source by the multi photon absorption event to induce a predetermined change in at least one target structure in the target cells; and
(5) returning the thus changed cells back to the subject to induce in the subject an autovaccine effect against the target cell,
wherein the changed cells act as an autovaccine and the energy source is x-rays, gamma rays, an electron beam, microwaves or radio waves.

In a further embodiment, methods in accordance with the present invention may further include a method for modifying a target structure which mediates or is associated with a biological activity, comprising:
(1) contacting said target structure with at least one activatable pharmaceutical agent that is capable of effecting a predetermined change in a target structure when activated and at least one plasmonics-active agent; and
(2) applying an initiation energy from an initiation energy source to target structure
wherein the plasmonics-active agent enhances or modulates the applied initiation energy, such that the enhanced initiation energy activates the activatable agent
thus causing the predetermined change to the target structure to occur, wherein said predetermined change modifies the target structure and modulates the biological activity of the target structure.

In a different embodiment, the predetermined change enhances the expression of, promotes the growth of, or increases the quantity of said target structure; enhances, inhibits or stabilizes the usual biological activity of said target structure compared to a similar untreated target structure, and/or alters the immunological or chemical properties of said target structure. In a different embodiment, said target structure is a compound that is modified by said predetermined change to be more or less antigenic or immunogenic The activatable pharmaceutical agent and derivatives thereof as well as the energy modulation agent, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Methods of administering agents according to the present invention are not limited to the conventional means such as injection or oral infusion, but include more advanced and complex forms of energy transfer. For example, genetically engineered cells that carry and express energy modulation agents may be used. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection.

Such transfected cells may be inserted or otherwise targeted at the site where diseased cells are located. In this embodiment, the initiation energy source may be a biochemical source as such ATP, in which case the initiation energy source is considered to be directly implanted in the transfected cell. Alternatively, a conventional micro-emitter device capable of acting as an initiation energy source may be transplanted at the site of the diseased cells.

It will also be understood that the order of administering the different agents is not particularly limited. Thus in some embodiments the activatable pharmaceutical agent may be administered before the energy modulation agent, while in other embodiments the energy modulation agent may be administered prior to the activatable pharmaceutical agent. It will be appreciated that different combinations of ordering may be advantageously employed depending on factors such as the absorption rate of the agents, the localization and molecular trafficking properties of the agents, and other pharmacokinetics or pharmacodynamics considerations.

A further embodiment is the use of the present invention for the treatment of skin cancer. In this example, a photoactivatable agent, preferably psoralen, is given to the patient, and is delivered to the skin lesion via the blood supply. An activation source having limited penetration ability (such as UV or IR) is shined directly on the skin—in the case of psoralen, it would be a UV light, or an IR source. With the use of an IR source, the irradiation would penetrate deeper and generate UV via two single photon events with psoralen.

In a further embodiment, methods according to this aspect of the present invention further include a step of separating the components of the treated cells into fractions and testing each fraction for autovaccine effect in a host. The components thus isolated and identified may then serve as an effective autovaccine to stimulate the host's immune system to suppress growth of the targeted cells.

In another aspect, the present invention further provides systems and kits for practicing the above described methods.

In one embodiment, a system for producing an autovaccine in a subject, comprises:
  at least one activatable pharmaceutical agent that is capable of activation by a multiphoton absorption event and of inducing a predetermined cellular change via at least one target structure in a target cell in said subject;
  means for placing said at least one activatable pharmaceutical agent in said subject; and
  an initiation energy source to provide initiation energy capable of activating the at least one activatable pharmaceutical agent in said target cell by the multi photon absorption event, wherein activation is either direct or indirect.

Figure 3:
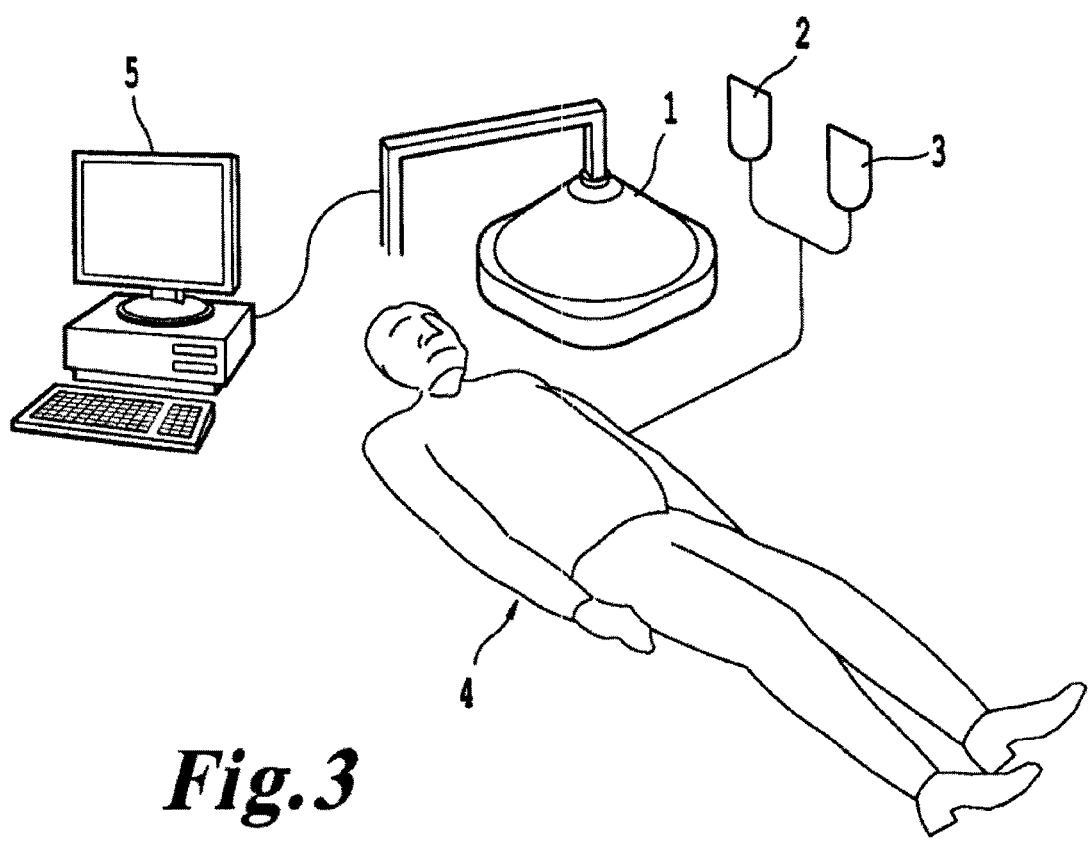
FIG. 3 illustrates a system according to one exemplary embodiment of the present invention.

In a different embodiment, a system in accordance with the present invention may include: (1) an initiation energy source; and (2) one or more energy modulation agents. The system may further comprise (3) one or more activatable pharmaceutical agents. In an additional embodiment, the system may comprise only (1) the initiation energy source. In yet another embodiment, the system may comprise (1) an initiation energy source; and (3) one or more activatable pharmaceutical agents. FIG. 3 illustrates a system according to one exemplary embodiment of the present invention. Referring to FIG. 3, an exemplary system according to one embodiment of the present invention may have an initiation energy source 1 directed at the subject 4. An activatable pharmaceutical agent 2 and an energy modulation agent 3 are administered to the subject 4. The initiation energy source may additionally be controlled by a computer system 5 that is capable of directing the delivery of the initiation energy.

In preferred embodiments, the initiation energy source may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.).

In other embodiments, endoscopic or laproscopic devices equipped with appropriate initiation energy emitter may be used as the initiation energy source. In such systems, the initiation energy may be navigated and positioned at the pre-selected coordinate to deliver the desired amount of initiation energy to the site.

In further embodiments, dose calculation and robotic manipulation devices may also be included in the system.

In yet another embodiment, there is also provided a computer implemented system for designing and selecting suitable combinations of initiation energy source, energy transfer agent, and activatable pharmaceutical agent, comprising:
  a central processing unit (CPU) having a storage medium on which is provided:
    a database of excitable compounds;
    a first computation module for identifying and designing an excitable compound that is capable of binding with a target cellular structure or component; and
    a second computation module predicting the resonance absorption energy of the excitable compound,
  wherein the system, upon selection of a target cellular structure or component, computes an excitable compound that is capable of binding with the target structure followed by a computation to predict the resonance absorption energy of the excitable compound.

Figure 4:
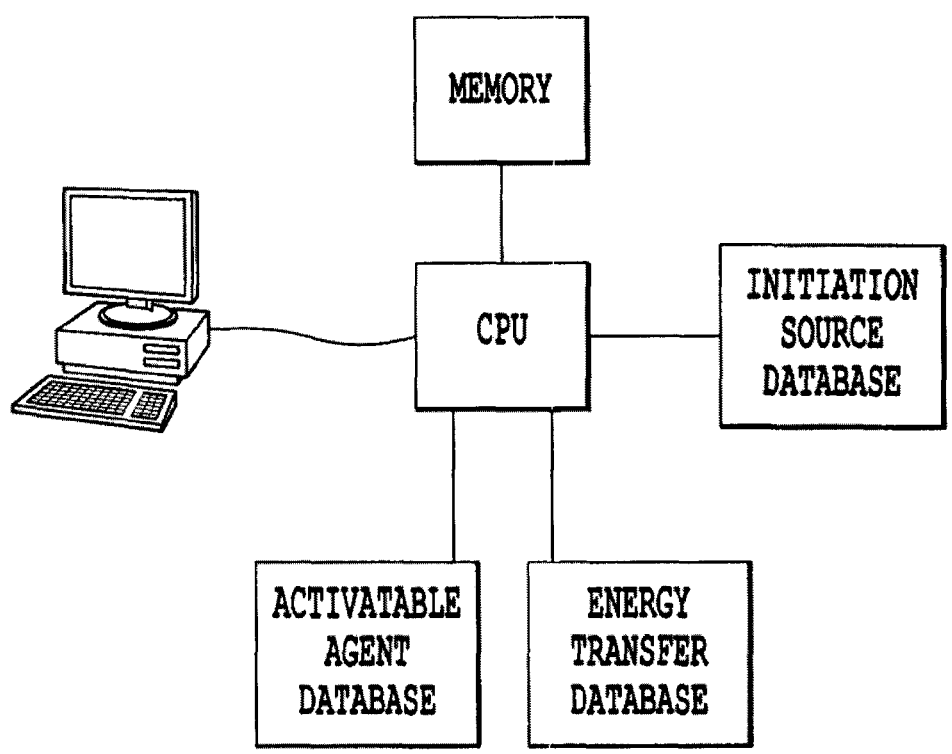
FIG. 4 illustrates an exemplary computer implemented system according to an embodiment of the present invention.

FIG. 4 illustrates an exemplary computer implemented system according to this embodiment of the present invention. Referring to FIG. 4, an exemplary computer-implemented system according to one embodiment of the present invention may have a central processing unit (CPU) connected to a memory unit, configured such that the CPU is capable of processing user inputs and selecting a combination of initiation source, activatable pharmaceutical agent, and energy transfer agent based on an energy spectrum comparison for use in a method of the present invention.

Figure 5:
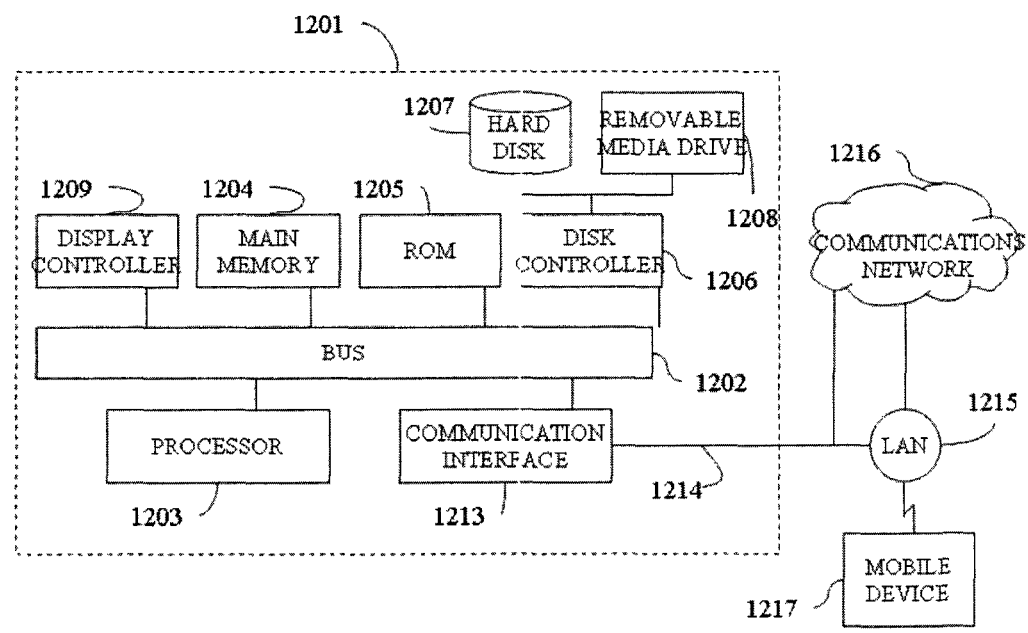
FIG. 5 illustrates an exemplary computer system (1201) for implementing various embodiments of the present invention.

FIG. 5 illustrates a computer system 1201 for implementing various embodiments of the present invention. The computer system 1201 may be used as the controller 55 to perform any or all of the functions of the CPU described above. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as a cathode ray tube (CRT), for displaying information to a computer user. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210. In addition, a printer may provide printed listings of data stored and/or generated by the computer system 1201.

The computer system 1201 performs a portion or all of the processing steps of the invention (such as for example those described in relation to FIG. 5) in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 1201, for driving a device or devices for implementing the invention, and for enabling the computer system 1201 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to, scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

The exemplary energy spectrum previously noted in FIG. 1 may also be used in this computer-implemented system.

The reagents and chemicals useful for methods and systems of the present invention may be packaged in kits to facilitate application of the present invention. In one exemplary embodiment, a kit including a psoralen, and fractionating containers for easy fractionation and isolation of autovaccines is contemplated. A further embodiment of kit would comprise at least one activatable pharmaceutical agent capable of causing a predetermined cellular change, at least one energy modulation agent capable of activating the at least one activatable agent when energized, and containers suitable for storing the agents in stable form, and preferably further comprising instructions for administering the at least one activatable pharmaceutical agent and at least one energy modulation agent to a subject, and for applying an initiation energy from an initiation energy source to activate the activatable pharmaceutical agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

In different aspect of the invention, a kit for modifying a target structure which mediates or is associated with a biological activity, comprising:

at least one agent selected from the group consisting of energy modulation agents, plasmonics-active agents and combinations thereof;

wherein the energy modulation agent, if present, upgrades or downgrades an initiation energy to an activation energy capable of causing, either directly or indirectly, a predetermined change in the target structure;

wherein the plasmonics-active agent, if present, enhances or modifies the applied initiation energy or the activation energy generated by the energy modulation agent, or both; and one or more containers suitable for storing the agents in stable forms.

In a different embodiment, a kit for performing a condition, disorder or disease treatment, comprises:

at least one energy modulation agent capable of adsorbing, intensifying or modifying an initiation energy into an energy that is capable of causing a predetermined change in a target structure; and containers suitable for storing the agents in stable form.

In yet another embodiment, the kit may further comprise instructions for administering the at least one energy modulation agent to a subject.

Plasmonics Enhanced Photospectral Therapy

In the PEPST embodiment of the present invention, the present invention is significantly different from the phototherapy technique often referred to Photothermal Therapy (PTT). To illustrate the difference between the present invention PEPST, a form of photospectral therapy (PST) and the PTT technique, the photochemical processes involved in PST and PPT is discussed below.

When drug molecules absorb excitation light, electrons undergo transitions from the ground state to an excited electronic state. The electronic excitation energy subsequently relaxes via radiative emission (luminescence) and radiationless decay channels. When a molecule absorbs excitation energy, it is elevated from $S_0$ to some vibrational level of one of the excited singlet states, $S_n$, in the manifold $S_1, \ldots, S_n$. In condensed media (tissue), the molecules in the $S_n$ state deactivate rapidly, within $10^{-13}$ to $10^{-11}$ s via vibrational relaxation (VR) processes, ensuring that they are in the lowest vibrational levels of $S_n$ possible. Since the VR process is faster than electronic transitions, any excess vibrational energy is rapidly lost as the molecules are deactivated to lower vibronic levels of the corresponding excited electronic state. This excess VR energy is released as thermal energy to the surrounding medium. From the $S_n$ state, the molecule deactivates rapidly to the isoenergetic vibrational level of a lower electronic state such as $S_{n-1}$ via an internal conversion (IC) process. IC processes are transitions between states of the same multiplicity. The molecule subsequently deactivates to the lowest vibronic levels of $S_{n-1}$ via a VR process. By a succession of IC processes immediately followed by VR processes, the molecule deactivates rapidly to the ground state $S_1$. This process results in excess VR and IC energy released as thermal energy to the surrounding medium leading to the overheating of the local environment surrounding the light absorbing drug molecules. The heat produced results in local cell or tissue destruction. The light absorbing species include natural chromophores in tissue or exogenous dye compounds such as indocyanine green, naphthalocyanines, and porphyrins coordinated with transition metals and metallic nanoparticles and nanoshells of metals. Natural chromophores, however, suffer from very low absorption. The choice of the exogenous photothermal agents is made on the basis of their strong absorption cross sections and highly efficient light-to-heat conversion. This feature greatly minimizes the amount of laser energy needed to induce local damage of the diseased cells, making the therapy method less invasive. A problem associated with the use of dye molecules is their photobleaching under laser irradiation. Therefore, nanoparticles such as gold nanoparticles and nanoshells have recently been used. The promising role of nanoshells in photothermal therapy of tumors has been demonstrated [Hirsch, L. R., Stafford, R. J., Bankson, J. A., Sershen, S. R., Rivera, B., Price, R. E., Hazle, J. D., Halas, N. J., and West, J. L., Nanoshell-mediated near-infrared thermal therapy of tumors under magnetic resonance guidance. PNAS, 2003. 100(23): p. 13549-13554]. The use of plasmonics-enhanced photothermal properties of metal nanoparticles for photothermal therapy has also been reviewed (Xiaohua Huang & Prashant K Jain & Ivan H. El-Sayed & Mostafa A. El-Sayed, "*Plasmonic photothermal therapy (PPTT) using gold nanoparticles*", Lasers in Medical Science, August 2007)

The PST method of the present invention, however, is based on the radiative processes (fluorescence, phosphorescence, luminescence, Raman, etc) whereas the PTT method is based on the radiationless processes (IC, VR and heat conversion) in molecules.

Basic Principle of Plasmonics and Enhanced Electromagnetic Fields

Whereas the photothermal properties of plasmonics metal nanoparticles have been used, the spectroscopic absorption and emission of plasmonics-active nanoparticles in phototherapy have not been reported.

In the present invention PEPST, the plasmonics-enhanced spectroscopic properties (spectral absorption, emission, scattering) are the major factors involved in the treatment.

The PEPST principle is based on the enhancement mechanisms of the electromagnetic field effect. There are two main sources of electromagnetic enhancement: (1) first, the laser electromagnetic field is enhanced due to the addition of a field caused by the polarization of the metal particle; (2) in addition to the enhancement of the excitation laser field, there is also another enhancement due to the molecule radiating an amplified emission (luminescence, Raman, etc.) field, which further polarizes the metal particle, thereby acting as an antenna to further amplify the Raman/Luminescence signal.

Electromagnetic enhancements are divided into two main classes: a) enhancements that occur only in the presence of a radiation field, and b) enhancements that occur even without a radiation field. The first class of enhancements is further divided into several processes. Plasma resonances on the substrate surfaces, also called surface plasmons, provide a major contribution to electromagnetic enhancement. An effective type of plasmonics-active substrate comprises nanostructured metal particles, protrusions, or rough surfaces of metallic materials. Incident light irradiating these surfaces excites conduction electrons in the metal, and induces excitation of surface plasmons leading to Raman/luminescence enhancement. At the plasmon frequency, the metal nanoparticles (or nanostructured roughness) become polarized, resulting in large field-induced polarizations and thus large local fields on the surface. These local fields increase the luminescence/Raman emission intensity, which is proportional to the square of the applied field at the molecule. As a result, the effective electromagnetic field experienced by the analyte molecule on these surfaces is much larger than the actual applied field. This field decreases as $1/r^3$ away from the surface. Therefore, in the electromagnetic models, the luminescence/Raman-active analyte molecule is not required to be in contact with the metallic surface but can be located anywhere within the range of the enhanced local field, which can polarize this molecule. The dipole oscillating at the wavelength λ of Raman or luminescence can, in turn, polarize the metallic nanostructures and, if λ is in resonance with the localized surface plasmons, the nanostructures can enhance the observed emission light (Raman or luminescence).

There are two main sources of electromagnetic enhancement: (1) first, the laser electromagnetic field is enhanced due to the addition of a field caused by the polarization of the metal particle; (2) in addition to the enhancement of the excitation laser field, there is also another enhancement due to the molecule radiating an amplified Raman/luminescence field, which further polarizes the metal particle, thereby acting as an antenna to further amplify the Raman/luminescence signal. Plasmonics-active metal nanoparticles also exhibit strongly enhanced visible and near-infrared light absorption, several orders of magnitude more intense compared to conventional laser phototherapy agents. The use of plasmonic nanoparticles as highly enhanced photoabsorbing agents thus provides a selective and efficient phototherapy strategy. The tunability of the spectral properties of the metal nanoparticles and the biotargeting abilities of the plasmonic nanostructures make the PEPST method promising.

Figure 6A:
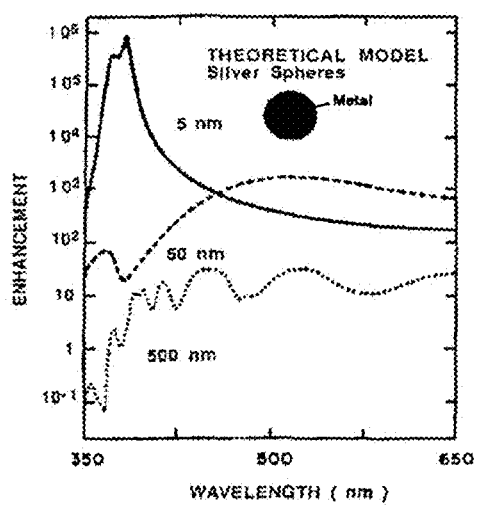
FIGS. 6A and 6B are graphical representations of plasmonic nanostructures and their theoretical electromagnetic enhancement at different excitation wavelengths.
Figure 6B:
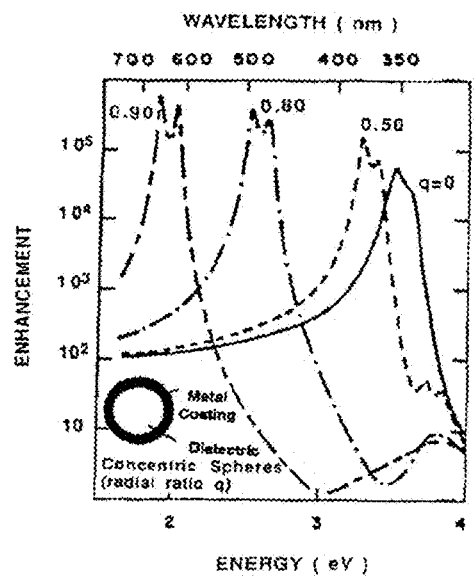

The present invention PEPST is based on several important mechanisms:

Increased absorption of the excitation light by the plasmonic metal nanoparticles, resulting in enhanced photoactivation of drug molecules Increased absorption of the excitation light by the plasmonic metal nanoparticles that serve as more efficient energy modulation agent systems, yielding more light for increased excitation of PA molecules Increased absorption of the excitation light by the photoactive drug system adsorbed on or near the plasmonic metal nanoparticles Increased light absorption of the energy modulation agent molecules adsorbed on or near the metal nanoparticles Amplified light emission from the energy modulation agent molecules adsorbed on or near the metal nanoparticles Increased absorption of emission light emitted from the energy modulation agent by the PA molecule One of several phenomena that can enhance the efficiency of light emitted (Raman or luminescence) from molecules adsorbed or near a metal nanostructures Raman scatter is the surface-enhanced Raman scattering (SERS) effect. In 1984, the general applicability of SERS as an analytical technique was first reported by one of the present inventors, and the possibility of SERS measurement for a variety of chemicals including several homocyclic and heterocyclic polyaromatic compounds [T. Vo-Dinh, MY. K. Hiromoto, G. M Begun and R. L. Moody, "*Surface-enhanced Raman spectroscopy for trace organic analysis,*" Anal. Chem., vol. 56, 1667, 1984]. Extensive research has been devoted to understanding and modeling the Raman enhancement in SERS since the mid 1980's. FIG. 6, for example, shows the early work by Kerker modeling electromagnetic field enhancements for spherical silver nanoparticles and metallic nanoshells around dielectric cores as far back as 1984 [M. M. Kerker, Acc. Chem. Res., 17, 370 (1984)]. This figure shows the result of theoretical calculations of electromagnetic enhancements for isolated spherical nanospheres and nanoshells at different excitation wavelengths. The intensity of the normally weak Raman scattering process is increased by factors as large as $10^{13}$ or $10^{15}$ for compounds adsorbed onto a SERS substrate, allowing for single-molecule detection. As a result of the electromagnetic field enhancements produced near nanostructured metal surfaces, nanoparticles have found increased use as fluorescence and Raman nanoprobes.

The theoretical models indicate that it is possible to tune the size of the nanoparticles and the nanoshells to the excitation wavelength. Experimental evidence suggests that the origin of the $10^6$- to $10^{15}$-fold Raman enhancement primarily arises from two mechanisms: a) an electromagnetic "lightning rod" effect occurring near metal surface structures associated with large local fields caused by electromagnetic resonances, often referred to as "surface plasmons"; and b) a chemical effect associated with direct energy transfer between the molecule and the metal surface.

According to classical electromagnetic theory, electromagnetic fields can be locally amplified when light is incident on metal nanostructures. These field enhancements can be quite large (typically $10^6$- to $10^7$-fold, but up to $10^{15}$-fold enhancement at "hot spots"). When a nanostructured metallic surface is irradiated by an electromagnetic field (e.g., a laser beam), electrons within the conduction band begin to oscillate at a frequency equal to that of the incident light. These oscillating electrons, called "surface plasmons," produce a secondary electric field which adds to the incident field. If these oscillating electrons are spatially confined, as is the case for isolated metallic nanospheres or roughened metallic surfaces (nanostructures), there is a characteristic frequency (the plasmon frequency) at which there is a resonant response of the collective oscillations to the incident field. This condition yields intense localized field enhancements that can interact with molecules on or near the metal surface. In an effect analogous to a "lightning rod," secondary fields are typically most concentrated at points of high curvature on the roughened metal surface.

Design, Fabrication and Operation of PEPST Probes

FIG. 7 shows a number of the various embodiments of PEPST probes that can be designed:

(A) probe comprising PA molecules bound to a metal (gold) nanoparticle;

(B) PA-containing nanoparticle covered with metal nanoparticles;

(C) Metal nanoparticle covered with PA nanocap;

(D) PA-containing nanoparticle covered with metal nanocap;

(E) Metal nanoparticle covered with PA nanoshell;

(F) PA-containing nanoparticle covered with metal nanoshell; and (G) PA-containing nanoparticle covered with metal nanoshell with protective coating layer.

A basic embodiment of the PEPST probe is shown in FIG. 7A. This probe comprises PA molecules bound to a metal (e.g., gold) nanoparticle. FIG. 8 illustrates the plasmonics-enhancement effect of the PEPSI' probe. The gold nanoparticles can serve as a drug delivery platform. Gold nanoparticles have been described as a novel technology in the field of particle-based tumor-targeted drug delivery [Giulio F. Paciotti and Lonnie Myer, DavidWeinreich, Dan Goia, Nicolae Pavel, Richard E. McLaughlin, Lawrence Tamarkin, "*Colloidal Gold: A Novel Nanoparticle Vector for Tumor Directed Drug Delivery, Drug Delivery*, 11:169-183, 2004]. Particle delivery systems capable of escaping phagocytic clearance by the reticuloendothelial system (RES) can facilitate targeting cancer therapeutics to solid tumors. Such delivery systems could preferentially accumulate within the tumor microenvironment under ideal conditions. A particle delivery system capable of sequestering a phototherapeutic drug selectively within a tumor may also reduce the accumulation of the drug in healthy organs. Consequently, these delivery systems may increase the relative efficacy or safety of therapy (less radiation energy and intensity), and therefore, will increase the drug's therapeutic efficiency.

Radiation of suitable energy is used to excite the PA drug molecules (e.g., aminolevulinic acid (ALA), porphyrins) and make them photoactive. For example, with the PDT drug ALA, light of a HeNe laser (632.8-nm excitation) can be used for excitation. In this case the metal nanoparticles are designed to exhibit strong plasmon resonance band around 632.8 nm. The surface plasmon resonance effect amplifies the excitation light at the nanoparticles, resulting in increased photoactivation of the PA drug molecules and improved therapy efficiency. The plasmonics-enhanced mechanism can also be used with the other PEPST probes in FIGS. 7B, 7C, 7D, 7E, 7F and 7G.

FIG. 34 shows yet other embodiment of plasmonics photo-active probes. FIG. 35 shows yet other embodiment of plasmonics photo-active probes that have a dielectric layer between the metal and the UC materials.

In one embodiment, a method for treating a condition, disorder or disease in accordance with the present invention comprises:

(1) administering to the subject at least one activatable pharmaceutical agent that is capable of effecting a predetermined change in a target structure when activated and at least one plasmonics-active agent; and (2) applying an initiation energy from an initiation energy source to the subject, wherein the plasmonics-active agent enhances or modifies the applied initiation energy, such that the enhanced initiation energy activates the activatable agent in situ, thus causing the predetermined change to the target structure to occur, wherein said predetermined change modifies the target structure and treats said condition, disorder, or disease.

In a different embodiment, a method in accordance with the present invention comprises:

(1) contacting said target structure with at least one activatable pharmaceutical agent that is capable of effecting a predetermined change in a target structure when activated and at least one plasmonics-active agent; and (2) applying an initiation energy from an initiation energy source to target structure wherein the plasmonics-active agent enhances or modifies the applied initiation energy, such that the enhanced initiation energy activates the activatable agent thus causing the predetermined change to the target structure to occur, wherein said predetermined change modifies the target structure and modulates the biological activity of the target structure.

In a different embodiment, at least one energy modulation agent and/or excitation-generating energy modulation agent material may be also added. In one embodiment, the energy modulation agent or excitation-generating energy modulation agent material may adsorb, intensify or modify the initiation energy which is then enhanced by at least one plasmonic agent. In a different embodiment, the energy modulation agent or excitation-generating energy modulation agent material may adsorb, intensify or modify energy enhanced by the at least plasmonics-active agent and emit an energy that is capable to activate the pharmaceutical activatable agent.

In another embodiment, the predetermined change enhances the expression of, promotes the growth of, or increases the quantity of said target structure. In yet, different embodiment, the predetermined change enhances, inhibits or stabilizes the usual biological activity of said target structure compared to a similar untreated target structure. In a different embodiment, the predetermined change alters the immunological or chemical properties of said target structure. In a different embodiment, the target structure is a compound that is modified by said predetermined change to be more or less antigenic or immunogenic.

Structures of Plasmonics-Active Metal Nanostructures

Plasmon resonances arise within a metallic nanoparticle from the collective oscillation of free electrons driven by an incident optical field. The plasmonic response of nanoparticles have played a role in a growing number of applications, including surface-enhanced Raman scattering (SERS), chemical sensing, drug delivery, photothermal cancer therapy and new photonic devices. The investigation and application of plasmonics nanosubstrates for SERS detection has been used by one of the present inventors for over two decades [T. Vo-Dinh, "Surface-Enhanced Raman Spectroscopy Using Metallic Nanostructures," *Trends in Anal. Chem.*, 17, 557 (1998)]. The first report by one of the present inventors on the practical analytical use of the SERS techniques for trace analysis of a variety of chemicals including several homocyclic and heterocyclic polyaromatic compounds was in 1984 [T. Vo-Dinh, MY. K. Hiromoto, G. M Begun and R. L. Moody, "*Surface-enhanced Raman spectroscopy for trace organic analysis,*" *Anal. Chem.*, vol. 56, 1667, 1984]. Since then, the development of SERS technologies for applications in chemical sensing, biological analysis and medical diagnostics has been ongoing. The substrates involve nanoparticles and semi-nanoshells comprising a layer of nanoparticles coated by a metal (such as silver) on one side (nanocaps or half-shells). Several groups have shown that plasmon resonances of spherical shells can be tuned by controlling the shell thickness and aspect ratios of the nanoshell structures [M. M. Kerker, *Acc. Chem. Res.*, 17, 370 (1984); J. B. Jackson, S. L. Westcott, L. R. Hirsch, J. L. West and N H. Halas, "*Controlling the surface enhanced Raman effect via the nanoshell geometry,*" *Appl. Phys. Lett.*, vol. 82, 257-259, 2003; S. J. Norton and T Vo-Dinh, "Plasmonic Resonances of nanoshells of Spheroidal Shape", IEEE Trans. Nanotechnology, 6, 627-638 (2007)]. These shells typically comprise a metallic layer over a dielectric core. In one embodiment of the present invention, these shells comprise spheroidal shells, since the plasmon resonances (both longitudinal and transverse modes) are influenced by both shell thickness and aspect ratio. A number of researchers have examined the plasmonic response of the solid spheroidal particle in their analysis of surface-enhanced Raman scattering, although the spheroidal shell appears not to have been investigated. The present invention also includes prolate and oblate spheroidal shells, which show some interesting qualitative features in their plasmon resonances. The spheroidal shell presents two degrees of freedom for tuning: the shell thickness and the shell aspect ratio [S. J. Norton and T Vo-Dinh, "*Plasmonic Resonances of Nanoshells of Spheroidal Shape*", IEEE Trans. Nanotechnology, 6, 627-638 (2007)].

FIG. 9 shows some of the various embodiments of plasmonics-active nanostructures that can be designed, and are preferred embodiments of the present invention:

(A) Metal nanoparticle;
(B) Dielectric nanoparticle core covered with metal nanocap;
(C) Spherical metal nanoshell covering dielectric spheroid core;
(D) Oblate metal nanoshell covering dielectric spheroid core;
(E) Metal nanoparticle core covered with dielectric nanoshell;
(F) Metal nanoshell with protective coating layer;
(G) Multi layer metal nanoshells covering dielectric spheroid core;
(H) Multi-nanoparticle structures;
(I) Metal nanocube and nanotriangle/nanoprism; and
(J) Metal cylinder.

PEPST Probes with Remotely-Activated Drug Release

Figure 10:
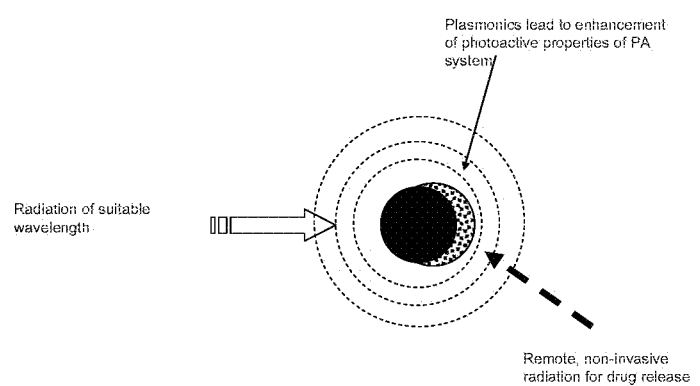
FIG. 10 is a graphical representation of one embodiment of a PEPST probe with remote drug release. Plasmonics excitation of metal nanoparticles enhances photo-active probes with remote drug release mechanism. Radiation of suitable wavelength (RF, MW, IR, NIR, VIS, UV to X ray and y ray) is used to excited PA and or nanoparticles.

In a further embodiment of the present invention, the PA drug molecules can be incorporated into a material (e.g., biocompatible polymer) that can form a nanocap onto the metal (gold) nanoparticles. The material can be a gel or biocompatible polymer that can have long-term continuous drug release properties. Suitable gel or biocompatible polymers include, but are not limited to poly(esters) based on polylactide (PLA), polyglycolide (PGA), polycarpolactone (PCL), and their copolymers, as well as poly(hydroxyalkanoate)s of the PHB-PHV class, additional poly(ester)s, natural polymers, particularly, modified poly(saccharide)s, e.g., starch, cellulose, and chitosan, polyethylene oxides, poly(ether)(ester) block copolymers, and ethylene vinyl acetate copolymers. The drug release mechanism can also be triggered by non-invasive techniques, such as RF, MW, ultrasound, photon (FIG. 10).

Figure 11:
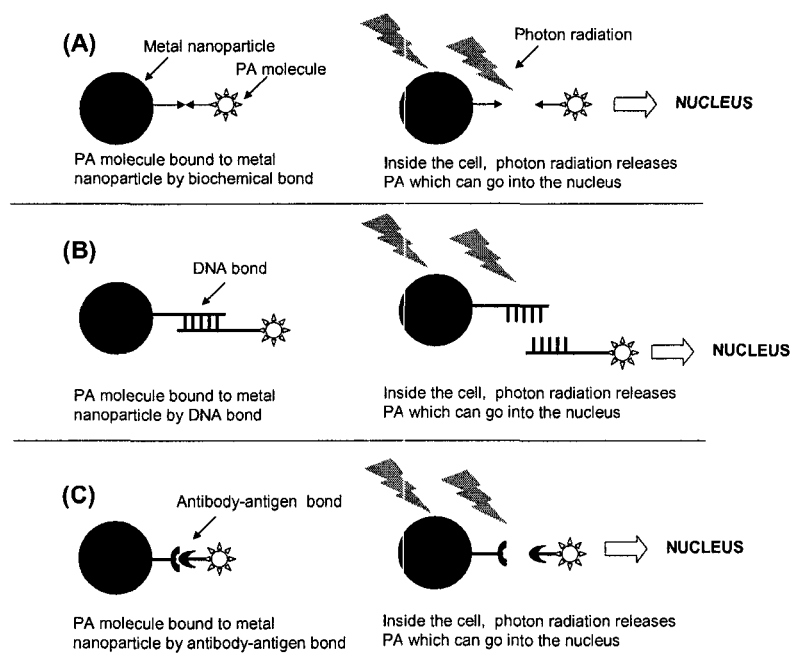
FIG. 11 is a graphical representation of several embodiments of PEPST probes with various linkers for remote drug release.

FIG. 11 shows other possible embodiments where the PA drug molecule is bound to the metal nanoparticles via a linker that can be cut by a photon radiation. Such a linker includes, but is not limited to, a biochemical bond (FIG. 11A), a DNA bond (FIG. 11B), or an antibody-antigen bond (FIG. 11C). In another embodiment, the linker is a chemically labile bond that will be broken by the chemical environment inside the cell. These types of probes are useful for therapy modalities where the PA molecules have to enter the nucleus (e.g., psoralen molecules need to enter the nucleus of cells and intercalate onto DNA). Since it is more difficult for metal nanoparticles to enter the cell nucleus than for smaller molecules, it is desirable to PEPST probes that have releasable PA molecules.

Disease-Targeted PEPST Probes

Aggregation of metal (such as silver or gold) nanoparticles (nanopsheres, nanorods, etc) is often a problem, especially with citrate-capped gold nanospheres, cetyl trimethylammonium bromide (CTAB)-capped gold nanospheres and nanorods and nanoshells because they have poor stability when they are dispersed in buffer solution due to the aggregating effect of salt ions. The biocompatibility can be improved and nanoparticle aggregation prevented by capping the nanoparticles with polyethylene glycol (PEG) (by conjugation of thiol-functionalized PEG with metal nanoparticles). Furthermore, PEGylated nanoparticles are preferentially accumulated into tumor tissues due to the enhanced permeability and retention effect, known as the "EPR" effect [Maedaa H, Fanga J, Inutsukaa T, Kitamoto Y (2003) *Vascular permeability enhancement in solid tumor: various factors, mechanisms involved and its implications. Int Immunopharmacol* 3:319-328; Paciotti G F, Myer L, Weinreich D, Goia D, Pavel N, McLaughlin R E, Tamarkin L (2004) *Colloidal gold: a novel nanoparticles vector for tumor directed drug delivery. Drug Deliv* 11:169-183]. Blood vessels in tumor tissue are more "leaky" than in normal tissue, and as a result, particles, or large macromolecular species or polymeric species preferentially extravasate into tumor tissue. Particles and large molecules tend to stay a longer time in tumor tissue due to the decreased lymphatic system, whereas they are rapidly cleared out in normal tissue. This tumor targeting strategy is often referred to as passive targeting whereas the antibody-targeting strategy is called active targeting.

To specifically target diseased cells, specific genes or protein markers, the drug systems of the present invention can be bound to a bioreceptor (e.g., antibody, synthetic molecular imprint systems, DNA, proteins, lipids, cell-surface receptors, aptamers, etc.). Immunotargeting modalities to deliver PA agents selectively to the diseased cells and tissue provide efficient strategies to achieving specificity, minimizing nonspecific injury to healthy cells, and reducing the radiation intensity used. Biofunctionalization of metal nanoparticles (e.g., gold, silver) can be performed using commonly developed and widely used procedures. There are several targeting strategies that can be used in the present invention: (a) nanoparticles conjugated to antibodies that recognize biomarkers specific to the diseased cells; (b) nanoparticles passivated by poly (ethylene) glycol (PEG), which is used to increase the biocompatibility and biostability of nanoparticles and impart them an increased blood retention time.

PEPST Probes with Bioreceptors

Figure 12:
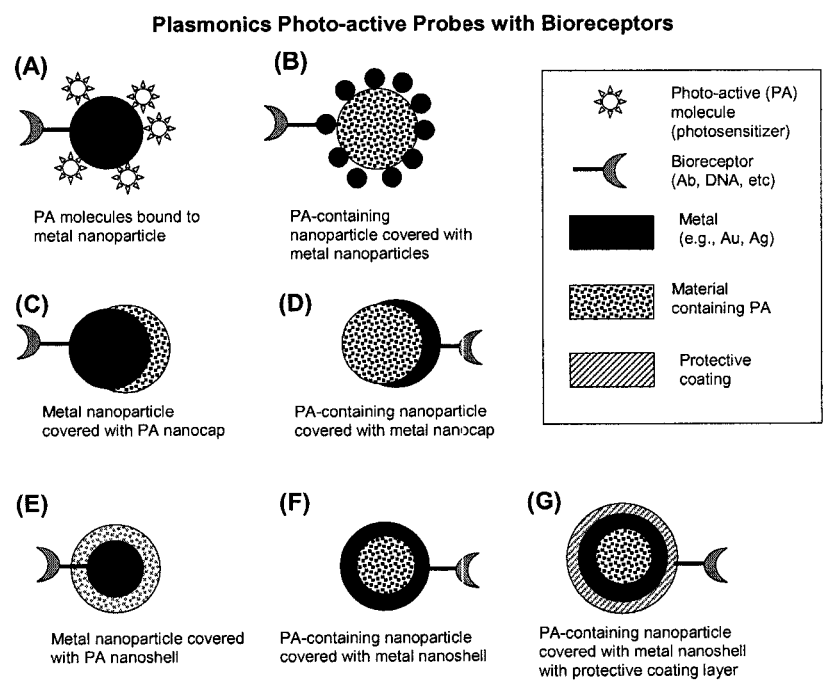
FIG. 12 is a graphical representation of several embodiments of plasmonics photo-active probes with bioreceptors.

Bioreceptors are the key to specificity for targeting disease cells, mutated genes or specific biomarkers. They are responsible for binding the biotarget of interest to the drug system for therapy. These bioreceptors can take many forms and the different bioreceptors that have been used are as numerous as the different analytes that have been monitored using biosensors. However, bioreceptors can generally be classified into five different major categories. These categories include: 1) antibody/antigen, 2) enzymes, 3) nucleic acids/DNA, 4) cellular structures/cells and 5) biomimetic. FIG. 12 illustrates a number of embodiments of the various PEPST probes with bioreceptors that can be designed. The probes are similar to those in FIG. 2 but have also a bioreceptor for tumor targeting.

Antibody Probes.

Antibody based targeting is highly active, specific and efficient. The antibodies are selected to target a specific tumor marker (e.g., anti-epidermal growth factor receptor (EGFR) antibodies targeted against overexpressed EGFR on oral and cervical cancer cells; anti-Her2 antibodies against overexpressed Her2 on breast cancer cells) Antibodies are biological molecules that exhibit very specific binding capabilities for specific structures. This is very important due to the complex nature of most biological systems. An antibody is a complex biomolecule, made up of hundreds of individual amino acids arranged in a highly ordered sequence. For an immune response to be produced against a particular molecule, a certain molecular size and complexity are necessary: proteins with molecular weights greater then 5000 Da are generally immunogenic. The way in which an antigen and its antigen-specific antibody interact may be understood as analogous to a lock and key fit, by which specific geometrical configurations of a unique key enables it to open a lock. In the same way, an antigen-specific antibody "fits" its unique antigen in a highly specific manner. This unique property of antibodies is the key to their usefulness in immunosensors where only the specific analyte of interest, the antigen, fits into the antibody binding site.

DNA Probes.

The operation of gene probes is based on the hybridization process. Hybridization involves the joining of a single strand of nucleic acid with a complementary probe sequence. Hybridization of a nucleic acid probe to DNA biotargets (e.g., gene sequences of a mutation, etc) offers a very high degree of accuracy for identifying DNA sequences complementary to that of the probe. Nucleic acid strands tend to be paired to their complements in the corresponding double-stranded structure. Therefore, a single-stranded DNA molecule will seek out its complement in a complex mixture of DNA containing large numbers of other nucleic acid molecules. Hence, nucleic acid probe (i.e., gene probe) detection methods are very specific to DNA sequences. Factors affecting the hybridization or reassociation of two complementary DNA strands include temperature, contact time, salt concentration, and the degree of mismatch between the base pairs, and the length and concentration of the target and probe sequences.

Biologically active DNA probes can be directly or indirectly immobilized onto a drug system, such as the energy modulation agent system (e.g., gold nanoparticle, a semiconductor, quantum dot, a glass/quartz nanoparticles, etc.) surface to ensure optimal contact and maximum binding. When immobilized onto gold nanoparticles, the gene probes are stabilized and, therefore, can be reused repetitively. Several methods can be used to bind DNA to different supports. The method commonly used for binding DNA to glass involves silanization of the glass surface followed by activation with carbodiimide or glutaraldehyde. The silanization methods have been used for binding to glass surfaces using 3 glycidoxypropyltrimethoxysilane (GOP) or aminopropyltrimethoxysilane (APTS), followed by covalently linking DNA via amino linkers incorporated either at the 3' or 5' end of the molecule during DNA synthesis.

Enzyme Probes.

Enzymes are often chosen as bioreceptors based on their specific binding capabilities as well as their catalytic activity. In biocatalytic recognition mechanisms, the detection is amplified by a reaction catalyzed by macromolecules called biocatalysts. With the exception of a small group of catalytic ribonucleic acid molecules, all enzymes are proteins. Some enzymes require no chemical groups other than their amino acid residues for activity. Others require an additional chemical component called a cofactor, which may be either one or more inorganic ions, such as $Fe^{2+}$, $Mg^{2+}$, $Mn^{2+}$, or $Zn^{2+}$, or a more complex organic or metalloorganic molecule called a coenzyme. The catalytic activity provided by enzymes allows for much lower limits of detection than would be obtained with common binding techniques. The catalytic activity of enzymes depends upon the integrity of their native protein conformation. If an enzyme is denatured, dissociated into its subunits, or broken down into its component amino acids, its catalytic activity is destroyed. Enzyme-coupled receptors can also be used to modify the recognition mechanisms.

PEGylated-Vectors for PEPST Probes

The synthesis of these particles was first reported by Michael Faraday, who, in 1857, described the chemical process for the production of nanosized particles of Au0 from gold chloride and sodium citrate (Faraday 1857). Initial formulations of the vector, manufactured by binding only TNF to the particles, were less toxic than native TNF and effective in reducing tumor burden in a murine model. Subsequent studies revealed that the safety of this vector was primarily due to its rapid uptake and clearance in the RES. This vector was reformulated to include molecules of thiol-derivatized polyethylene glycol (PEG-THIOL) that were bound with molecules of TNF on the gold nanoparticles surface. The new vector, PT-cAu-TNF, avoids detection and clearance by the RES, and actively and specifically sequesters TNF within a solid tumor. The altered biodistribution correlated to improvements. In the present invention, a preferred embodiment includes the use of PEGylated-Au nanoparticles-PA drug systems to avoid detection and clearance by the RES.

Immobilization of Biomolecules to Metal Nanoparticles

The immobilization of biomolecules (PA molecules, drugs, proteins, enzymes, antibodies, DNA, etc.) to a solid support can use a wide variety of methods published in the literature. Binding can be performed through covalent bonds taking advantage of reactive groups such as amine ($-NH_2$) or sulfide ($-SH$) that naturally are present or can be incorporated into the biomolecule structure. Amines can react with carboxylic acid or ester moieties in high yield to form stable amide bonds. Thiols can participate in maleimide coupling, yielding stable dialkylsulfides.

A solid support of interest in the present invention is the metal (preferably gold or silver) nanoparticles. The majority of immobilization schemes involving metal surfaces, such as gold or silver, utilize a prior derivatization of the surface with alkylthiols, forming stable linkages. Alkylthiols readily form self-assembled monolayers (SAM) onto silver surfaces in micromolar concentrations. The terminus of the alkylthiol chain can be used to bind biomolecules, or can be easily modified to do so. The length of the alkylthiol chain has been found to be an important parameter, keeping the biomolecules away from the surface, with lengths of the alkyl group from 4 to 20 carbons being preferred. For example, in the case for DNA hybridization this has been shown to displace nonspecifically adsorbed HS—(CH2)6-ss-DNA and reorient chemically attached HS—(CH2)6-ss-DNA in such a way to make the majority of surface bound probes accessible for hybridization (M. Culha, D. L. Stokes, an dT. Vo-Dinh, "Surface-Enhanced Raman Scattering for Cancer Diagnostics: Detection of the BLC2 Gene," Expert Rev. Mol. Diagnostics, 3, 669-675 (2003)). Furthermore, to avoid direct, non-specific DNA adsorption onto the surface, alkylthiols have been used to block further access to the surface, allowing only covalent immobilization through the linker [Steel, A. B.; Herne, T. M.; Tarlov, M. J. Anal. Chem. 1998, 70, 4670-7; Herne, T. M.; Tarlov, M. J. J. Am. Chem. Soc. 1997, 119, 8916-20]

There are many methods related to the preparation of stable oligonucleotide conjugates with gold particles by using thiol-functionalized biomolecules that had previously been shown to form strong gold-thiol bonds. Oligonucleotides with 5'-terminal alkanethiol functional groups as anchors can be bound to the surface of gold nanoparticles, and the resulting labels were robust and stable to both high and low temperature conditions [R. Elghanian, J. J. Storhoff, R. C. Mucic, R. L. Letsinger and C. A. Mirkin, *Selective colorimetric detection of polynucleotides based on the distance-dependent optical properties of gold nanoparticles. Science* 277 (1997), pp. 1078-1081]. A cyclic dithiane-epiandrosterone di sulfide linker has been developed for binding oligonucleotides to gold surfaces [R. Elghanian, J. J. Storhoff, R. C. Mucic, R. L. Letsinger and C. A. Mirkin, *Selective colorimetric detection of polynucleotides based on the distance-dependent optical properties of gold nanoparticles. Science* 277 (1997), pp. 1078-1081]. Li et al. have reported a trithiol-capped oligonucleotide that can stabilize gold metal nanoparticles having diameters ≥100 nm, while retaining hybridization properties that are comparable to acyclic or dithiol-oligonucleotide modified particles [Z. Li, R. C. Jin, C. A. Mirkin and R. L. Letsinger, *Multiple thiol-anchor capped DNA-gold nanoparticle conjugates. Nucleic Acids Res.* 30 (2002), pp. 1558-1562].

In general silver nanoparticles cannot be effectively passivated by alkylthiol-modified oligonucleotides using the established experimental protocols that were developed for gold particles. A method of generating core-shell particles comprising a core of silver and a thin shell of gold has allowed silver nanoparticles to be readily functionalized with alkylthiol-oligonucleotides using the proven methods used to prepare pure gold particle-oligonucleotide conjugates. [Y. W. Cao, R. Jin and C. A. Mirkin, *DNA-modified core-shell Ag/Au nanoparticles. J. Am. Chem. Soc.* 123 (2001), pp. 7961-7962].

To facilitate the use of biomolecule-conjugated plasmonics-active nanoprobes (PAN) it is important that the recognition region of the biomolecule is fully accessible to the biotarget. Commonly a polynucleotide extension sequence is incorporated to serve as a spacer between the PAN and the oligonucleotide recognition region. To achieve high sensitivity and selectivity in assays based on DNA hybridization it is important that the PAN label colloidal solution is stable. Recently, Storhoff et al. [LI Storhoff, R. Elghanian, C. A. Mirkin and R. L. Letsinger, *Sequence-dependent stability of DNA-modified gold nanoparticles. Langmuir* 18 (2002), pp. 6666-6670] have shown that the base composition of the oligonucleotide has a significant effect on colloid stability and on oligonucleotide surface coverage. Otsuka et al. have used a heterobifunctional thiol-PEG (polyethylene glycol) derivative as a linker to stabilize gold PRPs [H. Otsuka, Y Akiyama, Y Nagasaki and K Kataoka, *Quantitative and reversible lectin-induced association of gold nanoparticles modified with a-lactosyl-ω-mercapto-poly(ethylene glycol). J. Am. Chem. Soc.* 123 (2001), pp. 8226-8230].

Proteins are usually bound to PANs using non-covalent, passive absorption. Alternatively, a mercapto-undecanoic acid linker/spacer molecule can be used to attach NeutrAvidin covalently to gold and silver segmented nanorods [I. D. Walton, S. M. Norton, A. Balasingham, L. He, D. F. Oviso, D. Gupta, P. A. Raju, M. J. Natan and R. G. Freeman, *Particles for multiplexed analysis in solution: detection and identification of striped metallic particles using optical* microscopy. *Anal. Chem.* 74 (2002), pp. 2240-2247]. The thiol groups bind to the metal surface, and the carboxyl functional groups on the particle surface are activated using EDC and s-NHS reagents and then cross-linked to the amino groups in NeutrAvidin. The ability to fabricate core-shell particles where the core is metal and the shell is composed of latex, silica, polystyrene or other non-metal material provides a promising alternative approach to immobilizing biomolecules and engineering particle surfaces [T. K. Mandal, M. S. Fleming and D. R. Walt, *Preparation of polymer coated gold nanoparticles by surface-confined living radical polymerization at ambient temperature. Nano Letters* 2 (2002), pp. 3-7; S. O. Obare, N. R. Jana and C. J. Murphy, *Preparation of polystyrene-and silica-coated gold nanorods and their use as templates for the synthesis of hollow nanotubes. Nano Letters* 1 (2001), pp. 601-603; C. Radloff and N. J. Halas, *Enhanced thermal stability of silica-encapsulated metal nanoshells. Appl. Phys. Lett.* 79 (2001), pp. 674-676; L. Quaroni and G. Chumanov, *Preparation of polymer-coated functionalized silver nanoparticles. J. Am. Chem. Soc.* 121 (1999), pp. 10642-10643p; F. Caruso, *Nanoengineering of particle surfaces. Adv. Mater.* 13 (2001), pp. 11-22].

Silver surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold [Burges, J. D.; Hawkridge, F. M. Langmuir 1997, 13, 3781-6]. After self-assembled monolayer (SAM) formation on gold/silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds. As a general rule, a more active intermediate (labile ester) is first formed with the carboxylic acid moiety and in a later stage reacted with the free amine, increasing the coupling yield. Successful coupling procedures include, but are not limited to:

Binding Procedure Using N-Hydroxysuccinimide (NHS) and its Derivatives

The coupling approach involves the esterification under mild conditions of a carboxylic acid with a labile group, an N-hydroxysuccinimide (NHS) derivative, and further reaction with free amine groups in a polypeptide (enzymes, antibodies, antigens, etc) or amine-labeled DNA, producing a stable amide [Boncheva, M.; Scheibler, L.; Lincoln, P.; Vogel, H.; Akerman, B. Langmuir 1999, 15, 4317-20]. NHS reacts almost exclusively with primary amine groups. Covalent immobilization can be achieved in as little as 30 minutes. Since $H_2O$ competes with $—NH_2$ in reactions involving these very labile esters, it is important to consider the hydrolysis kinetics of the available esters used in this type of coupling. The derivative of NHS, O—(N-succinimidyl)-N,N,N',N'-tetramethyluronium tetrafluoroborate, increases the coupling yield by utilizing a leaving group that is converted to urea during the carboxylic acid activation, hence favorably increasing the negative enthalpy of the reaction.

Binding Procedure Using Maleimide

Maleimide can be used to immobilize biomolecules through available —SH moieties. Coupling schemes with maleimide have been proven useful for the site-specific immobilization of antibodies, Fab fragments, peptides, and SH-modified DNA strands. Sample preparation for the maleimide coupling of a protein involves the simple reduction of disulfide bonds between two cysteine residues with a mild reducing agent, such as dithiothreitol, 2-mercaptoethanol or tris(2-carboxyethyl)phosphine hydrochloride. However, disulfide reduction will usually lead to the protein losing its natural conformation, and might impair enzymatic activity or antibody recognition. The modification of primary amine groups with 2-iminothiolane hydrochloride (Traut's reagent) to introduce sulfydryl groups is an alternative for biomolecules lacking them. Free sulfhydryls are immobilized to the maleimide surface by an addition reaction to unsaturated carbon-carbon bonds [Jordan, C. E., et al., 1997].

Binding Procedure Using Carbodiimide.

Surfaces modified with mercaptoalkyldiols can be activated with 1,1'-carbonyldiimidazole (CDI) to form a carbonylimidazole intermediate. A biomolecule with an available amine group displaces the imidazole to form a carbamate linkage to the alkylthiol tethered to the surface [Potyrailo, R. A., et al., 1998].

Other Experimental Procedures to Conjugate Biomolecules to Metal (e.g., Silver, Gold) Nanoparticles.

In one preferred embodiment, nanoparticles of metal colloid hydrosols are prepared by rapidly mixing a solution of $AgNO_3$ with ice-cold $NaBH_4$. For developing a SMP probes, a DNA segment is bound to a nanoparticle of silver or gold. The immobilization of biomolecules (e.g., DNA, antibodies, enzymes, etc.) to a solid support through covalent bonds usually takes advantage of reactive groups such as amine ($—NH_2$) or sulfide (—SH) that naturally are present or can be incorporated into the biomolecule structure. Amines can react with carboxylic acid or ester moieties in high yield to form stable amide bonds. Thiols can participate in maleimide coupling yielding stable dialkylsulfides.

In one preferred embodiment, silver nano particles are used. In one preferred embodiment, the immobilization schemes involving Ag surfaces utilize a prior derivatization of the surface with alkylthiols, forming stable linkages are used. Alkylthiols readily form self-assembled monolayers (SAM) onto silver surfaces in micromolar concentrations. The terminus of the alkylthiol chain can be directly used to bind biomolecules, or can be easily modified to do so. The length of the alkylthiol chain was found to be an important parameter, keeping the biomolecules away from the surface. Furthermore, to avoid direct, non-specific DNA adsorption onto the surface, alkylthiols were used to block further access to the surface, allowing only covalent immobilization through the linker.

Silver/gold surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold.

After SAM formation on silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds. In one embodiment, more active intermediate (labile ester) is first formed with the carboxylic acid moiety and in a later stage reacted with the free amine, increasing the coupling yield. Successful coupling procedures include:

The coupling approach used to bind DNA to a silver nanoparticle involves the esterification under mild conditions of a carboxylic acid with a labile group, an N-hydroxysuccinimide (NHS) derivative, and further reaction with free amine groups in a polypeptide (enzymes, antibodies, antigens, etc) or amine-labeled DNA, producing a stable amide [4]. NHS reacts almost exclusively with primary amine groups. Covalent immobilization can be achieved in as little as 30 minutes. Since $H_2O$ competes with —$NH_2$ in reactions involving these very labile esters, it is important to consider the hydrolysis kinetics of the available esters used in this type of coupling. The derivative of NHS used in FIG. 101, O—(N-succinimidyl)-N,N,N',N'-tetramethyluronium tetrafluoroborate, increases the coupling yield by utilizing a leaving group that is converted to urea during the carboxylic acid activation, hence favorably increasing the negative enthalpy of the reaction.

Spectral Range of Light Used for PEPST

A plasmonics enhanced effect can occur throughout the electromagnetic region provided the suitable nanostructures, nanoscale dimensions, metal types are used. Therefore, the PEPST concept is valid for the entire electromagnetic spectrum, i.e, energy, ranging from gamma rays and X rays throughout ultraviolet, visible, infrared, microwave and radio frequency energy. However, for practical reasons, visible and NIR light are used for silver and gold nanoparticles, since the plasmon resonances for silver and gold occur in the visible and NIR region, respectively. Especially for gold nanoparticles, the NIR region is very appropriate for non-invasive therapy.

Photon Excitation in the Therapeutic Window of Tissue

Figure 13:
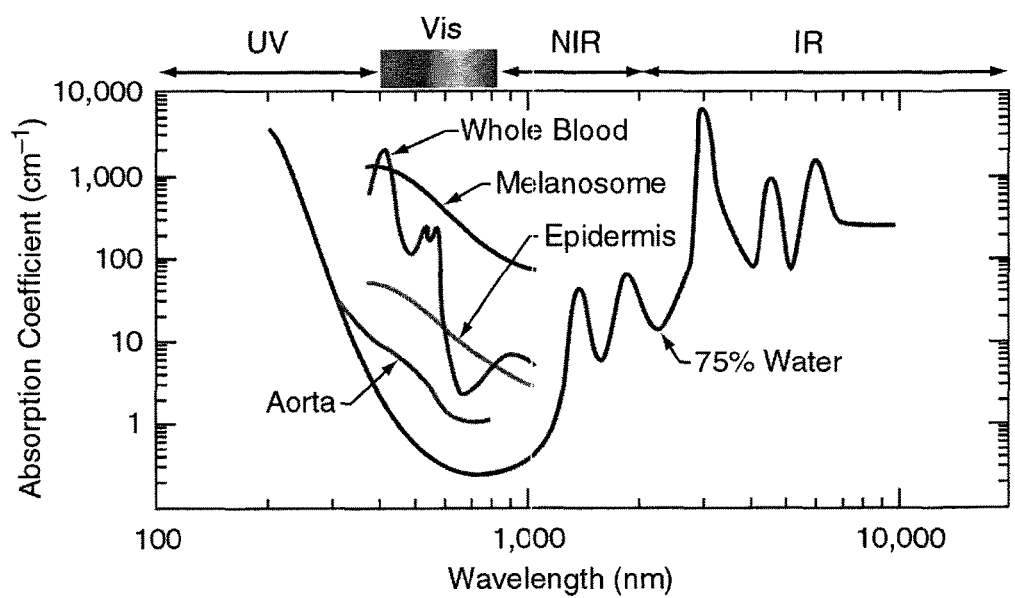
FIG. 13 is a graphical representation of the "therapeutic window" in tissue and absorption spectra of biological components.

There are several methods using light to excite photoactivate compounds non-invasively. We can use light having wavelengths within the so-called "therapeutic window" (700-1300 nm). The ability of light to penetrate tissues depends on absorption. Within the spectral range known as the therapeutic window (or diagnostic window), most tissues are sufficiently weak absorbers to permit significant penetration of light. This window extends from 600 to 1300 nm, from the orange/red region of the visible spectrum into the NIR. At the short-wavelength end, the window is bound by the absorption of hemoglobin, in both its oxygenated and deoxygenated forms. The absorption of oxygenated hemoglobin increases approximately two orders of magnitude as the wavelength shortens in the region around 600 nm. At shorter wavelengths many more absorbing biomolecules become important, including DNA and the amino acids tryptophan and tyrosine. At the infrared (IR) end of the window, penetration is limited by the absorption properties of water. Within the therapeutic window, scattering is dominant over absorption, and so the propagating light becomes diffuse, although not necessarily entering into the diffusion limit. FIG. 13 shows a diagram of the therapeutic window of tissue. The following section discusses the use of one-photon and multi-photon techniques for therapy.

Light Excitation Methods: Single-Photon and Multi-Photon Excitation

Two methods can be used, one-photon or multi-photon excitation. If the two-photon technique is used, one can excite the PA molecules with light at 700-1000 nm, which can penetrate deep inside tissue, in order to excite molecules that absorb in the 350-500 nm spectral region. This approach can excite the psoralen compounds, which absorb in the 290-350 nm spectral region and emit in the visible. With the one-photon method, the photo-activator (PA) drug molecules can directly absorb excitation light at 600-1300 nm. In this case we can design a psoralen-related system (e.g., psoralens having additional aromatic rings or other conjugation to alter the ability to absorb at different wavelengths) or use other PA systems: photodynamic therapy drugs, ALA, etc.

PEPST Modality for Photopheresis Using X Ray Excitation

Need for X-Ray Excitation

Photopheresis has been demonstrated to be an effective treatment for a number of diseases. However, there is a strong need to develop non-invasive modalities where the excitation light can directly irradiate the photoactive compounds without the need for removal and reinfusion of blood from patients. One method for an improved and practical modality for such therapy was described in U.S. Ser. No. 11/935,655, filed Nov. 6, 2007, the entire contents of which are hereby incorporated by reference.

Although X-ray can excite compounds in deep tissue non-invasively, X-ray is not easily absorbed by organic drug compounds. The present invention provides a solution to that problem, by the providing of a molecular system that can absorb the X-ray energy and change that energy into other energies that can be used to activate drug molecules. More specifically, the molecular system that can absorb and change the X-ray energy in the present invention is the PEPST probes comprising nanoparticles.

Figure 14:
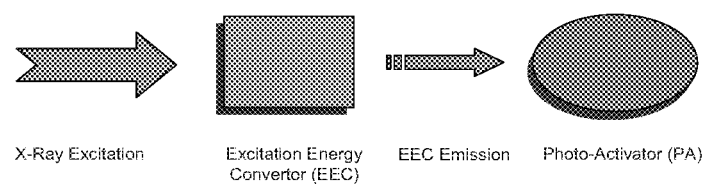
FIG. 14 is a graphical representation of an embodiment of the energy modulation agent (or excitation energy converter/EEC)-photo activator (PA) system of the present invention. X-ray is used to excite an "excitation energy converter" (EEC) molecular system. The EEC absorbs the X-ray energy and emits light that is absorbed by the "photo-activator" (PA) molecule. The PA molecule becomes an activated drug for disease treatment.

In this embodiment, the present invention uses X-rays for excitation. The advantage is the ability to excite molecules non-invasively since X-ray can penetrate deep in tissue. However, the limitation is the fact that X-ray does not interact with most molecules. In one embodiment of the present invention, the drug molecule (or PA) is bound to a molecular entity, referred to as an "energy modulation agent" that can interact with the X-rays, and then emit light that can be absorbed by the PA drug molecules. (FIG. 14)

PEPST Probes for X Ray Excitation

In the previous sections, the advantage of gold nanoparticles as plasmonics-active systems have been discussed. Furthermore, gold nanoparticles are also good energy modulation agent systems since they are biocompatible and have been shown to be a possible candidate for contrast agents for X-ray [Hainfeld et al, *The British Journal of radiology*, 79, 248, 2006]. The concept of using high-Z materials for dose enhancement in cancer radiotherapy was advanced over 20 years ago. The use of gold nanoparticles as a dose enhancer seems more promising than the earlier attempts using microspheres and other materials for two primary reasons. First, gold has a higher Z number than iodine (I, Z=53) or gadolinium (Gd, Z=64), while showing little toxicity, up to at least 3% by weight, on either the rodent or human tumor cells. The gold nanoparticles were non-toxic to mice and were largely cleared from the body through the kidneys. This novel use of small gold nanoparticles permitted achievement of the high metal content in tumors necessary for significant high-Z radioenhancement [James F Hainfeld, Daniel N Slatkin and Henry M Smilowitz, *The use of gold nanoparticles to enhance radiotherapy in mice, Phys. Med. Biol.* 49 (2004)]

Delivering a lethal dose of radiation to a tumor while minimizing radiation exposure of nearby normal tissues remains the greatest challenge in radiation therapy. The dose delivered to a tumor during photon-based radiation therapy can be enhanced by loading high atomic number (Z) materials such as gold (Au, Z=79) into the tumor, resulting in greater photoelectric absorption within the tumor than in surrounding tissues. Thus, gold clearly leads to a higher tumor dose than either iodine or gadolinium. Second, nanoparticles provide a better mechanism than microspheres, in terms of delivering high-Z materials to the tumor, overcoming some of the difficulties found during an earlier attempt using gold microspheres [Sang Hyun Cho, *Estimation of tumor dose enhancement due to gold nanoparticles during typical radiation treatments: a preliminary Monte Carlo study, Phys. Med. Biol.* 50 (2005)]

Gold (or metal) complexes with PA ligands: Gold (or metal) complexes with PA can preferably be used in the present invention. The metal can be used as an energy modulation agent system. For example, gold complexes with psoralen-related ligands can be used as a hybrid energy modulation agent-PA system. The gold molecules serve as the energy modulation agent system and the ligand molecules serve as the PA drug system. Previous studies indicated that gold(I) complexes with diphosphine and bipyridine ligands exhibit X-ray excited luminescence [Ref 3: Kim et al, *Inorg. Chem.*, 46, 949, 2007].

Figure 15:
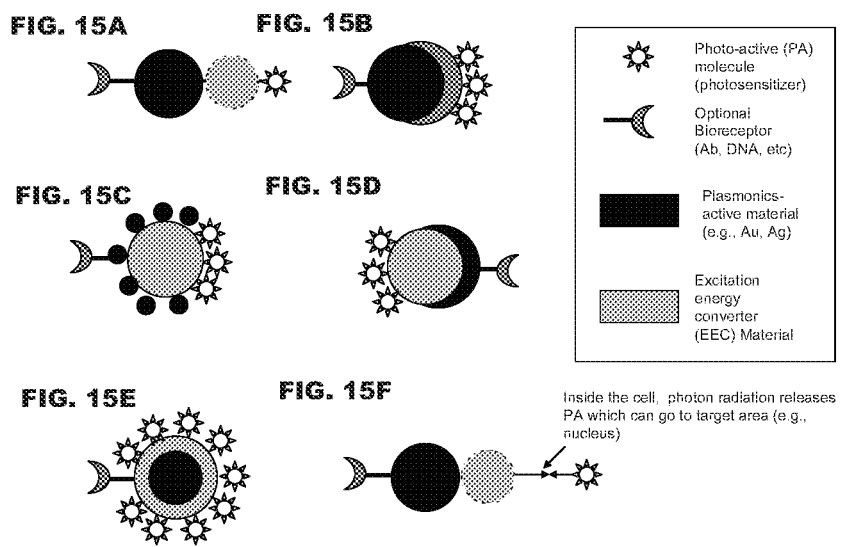
FIGS. 15A-15F are graphical representations of several embodiments of plasmonics photo-active energy modulation agent-PA probes.

FIG. 15 shows a number of the various embodiments of PEPST probes that can be preferably used for X ray excitation of energy modulation agent-PA system. These probes comprise:

(A) PA molecules bound to energy modulation agent and to plasmonic metal nanoparticle;
(B) Plasmonic metal nanoparticle with energy modulation agent nanocap covered with PA molecules;
(C) PA-covered nanoparticle with plasmonic metal nanoparticles;
(D) Energy modulation agent-containing nanoparticle covered with PA molecules and plasmonic metal nanocap;
(E) Plasmonic metal nanoparticle core with energy modulation agent nanoshell covered with PA molecule; and
(F) PA molecule bound to energy modulation agent (attached to plasmonics metal nanoparticle) nanoparticle by detachable biochemical bond.

Examples of PEPST System Based on Energy Modulation Agent-PA

For purposes of simplification, the following discussion is centered on gold as the metal material and CdS as the energy modulation agent material (which can also be used as DNA stabilized CdS, see Ma et al, *Langmuir*, 23 (26), 12783-12787 (2007)) and psoralen as the PA molecule. However, it is to be understood that many other embodiments of metal material, energy modulation agent and PA molecule are possible within the bounds of the present invention, and the following discussion is for exemplary purposes only. Suitable metals that can be used in plasmon resonating shells or other plasmon resonating structures can be include, but are not limited to, gold, silver, platinum, palladium, nickel, ruthenium, rhenium, copper, and cobalt.

In the embodiment of FIG. 15A, the PEPST system comprises gold nanoparticles, an energy modulation agent nanoparticle (e.g., CdS) linked to a PA drug molecule (e.g., psoralen). X ray is irradiated to CdS, which absorbs X rays [Hua et al, *Rev. Sci. Instrum.*, 73, 1379, 2002] and emits CdS XEOL light (at 350-400 nm) that is plasmonics-enhanced by the gold nanoparticle. This enhanced XEOL light is used to photoactivate psoralen (PA molecule). In this case the nanostructure of the gold nanoparticle is designed to enhance the XEOL light at 350-400 nm.

In the embodiment of FIG. 15B, the PEPST system comprises a plasmonics-active metal (gold) nanoparticle with energy modulation agent nanocap (CdS) covered with PA molecules (e.g., psoralen). X ray is irradiated to CdS, which absorbs X ray and emits XEOL light that is plasmonics-enhanced by the gold nanoparticle. This enhanced XEOL light is used to photoactivate psoralen (PA molecule).

In the embodiment of FIG. 15C, the PEPST system comprises a PA (e.g., psoralen)-covered CdS nanoparticle with smaller plasmonic metal (gold) nanoparticles. X ray is irradiated to CdS, which absorbs X ray and emits XEOL light that is plasmonics-enhanced by the gold nanoparticle. This enhanced XEOL light is used to photoactivate psoralen (PA molecule).

In the embodiment of FIG. 15D, the energy modulation agent core comprises CdS or CsCl nanoparticles covered with a nanocap of gold. X ray is irradiated to CdS or CsCl, which absorbs X ray [Jaegle et al, *J. Appl. Phys.*, 81, 2406, 1997] and emits XEOL light that is plasmonics-enhanced by the gold nanocap structure. This enhanced XEOL light is used to photoactivate psoralen (PA molecule).

Similarly, the embodiment in FIG. 15E comprises a spherical gold core covered by a shell of CdS or CsCl. X ray is irradiated to CdS or CsCl material, which absorbs X ray [Jaegle et al, *J. Appl. Phys.*, 81, 2406, 1997] and emits XEOL light that is plasmonics-enhanced by the gold nanosphere. This enhanced XEOL light is used to photoactivate psoralen (PA molecule).

In the embodiment of FIG. 15F, the PEPST system comprises gold nanoparticles, and an energy modulation agent nanoparticle (e.g., CdS) linked to a PA drug molecule (e.g., psoralen) by a link that can be detached by radiation. X ray is irradiated to CdS, which absorbs X ray and emits CdS XEOL light (at 350-400 nm) that is plasmonics-enhanced by the gold nanoparticle. This enhanced XEOL light is used to photoactivate psoralen (PA molecule). In this case the nanostructure of the gold nanoparticle is designed to enhance the XEOL light at 350-400 nm.

In alternative embodiments, the metal nanoparticles or single nanoshells are replaced by multi layers of nanoshells [Kun Chen, Yang Liu, Guillermo Ameer, Vadim Backman, *Optimal design of structured nanospheres for ultrasharp light-scattering resonances as molecular imaging multilabels, Journal of Biomedical Optics*, 10(2), 024005 (March/April 2005)].

In other alternative embodiments the metal nanoparticles are covered with a layer (1-30 nm) of dielectric material (e.g. silica). The dielectric layer (or nanoshell) is designed to prevent quenching of the luminescence light emitted by the energy modulation agent (also referred to as EEC) molecule(s) due to direct contact of the metal with the energy modulation agent molecules. In yet other alternative embodiments, the energy modulation agent molecules or materials are bound to (or in proximity of) a metal nanoparticle via a spacer (linker). The spacer is designed to prevent quenching of the luminescence light emitted by the energy modulation agent molecules or materials.

Other Useable Materials

The energy modulation agent materials can include any materials that can absorb X ray and emit light in order to excite the PA molecule. The energy modulation agent materials include, but are not limited to:

metals (gold, silver, etc);
quantum dots;
semiconductor materials;
scintillation and phosphor materials;
materials that exhibit X-ray excited luminescence (XEOL);
organic solids, metal complexes, inorganic solids, crystals, rare earth materials (lanthanides), polymers, scintillators, phosphor materials, etc.; and
materials that exhibit excitonic properties.

Quantum dots, semiconductor nanostructures. Various materials related to quantum dots, semiconductor materials, etc. can be used as energy modulation agent systems. For example CdS-related nanostructures have been shown to exhibit X-ray excited luminescence in the UV-visible region [Hua et al, *Rev. Sci. Instrum.*, 73, 1379, 2002].

Scintillator Materials as energy modulation agent systems. Various scintillator materials can be used as energy modulation agents since they absorb X-ray and emit luminescence emission, which can be used to excite the PA system. For example, single crystals of molybdates can be excited by X-ray and emit luminescence around 400 nm [Mirkhin et al, *Nuclear Instrum. Meth. In Physics Res. A*, 486, 295 (2002)].

Solid Materials as energy modulation agent systems: Various solid materials can be used as energy modulation agents due to their X-ray excited luminescence properties. For example CdS (or CsCl) exhibit luminescence when excited by soft X-ray [Jaegle et al, *J. Appl. Phys.*, 81, 2406, 1997].

XEOL materials: lanthanides or rare earth materials [L. Soderholm, G. K. Liu, Mark R. Antonioc, F. W. Lytle, *X-ray excited optical luminescence .XEOL. detection of x-ray absorption fine structure .XAFZ, J. Chem. Phys*, 109, 6745, 1998], Masashi Ishiia, Yoshihito Tanaka and Tetsuya Ishikawa, Shuji Komuro and Takitaro Morikawa, Yoshinobu Aoyagi, *Site-selective x-ray absorption fine structure analysis of an optically active center in Er-doped semiconductor thin film using x-ray-excited optical luminescence, Appl. Phys. Lett*, 78, 183, 2001]

Figure 16:
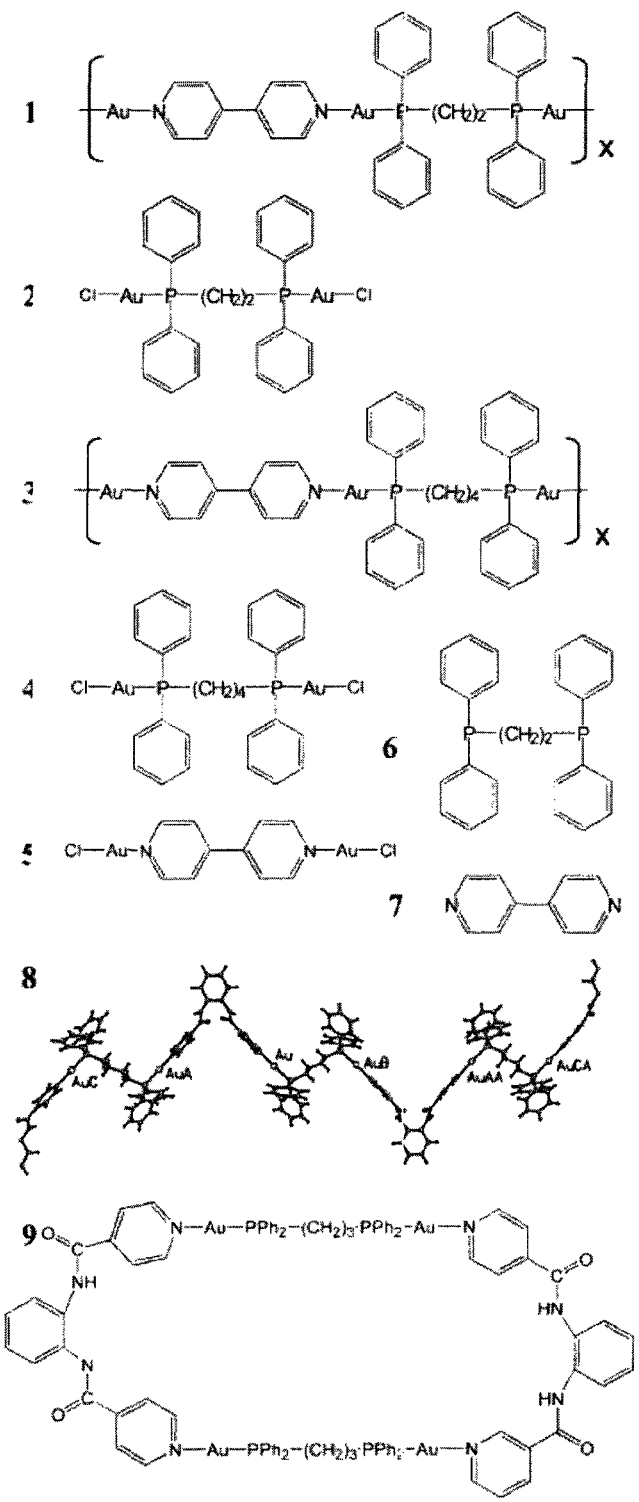
FIG. 16 shows structures of various preferred embodiments of gold complexes exhibiting XEOL.
Figure 17:
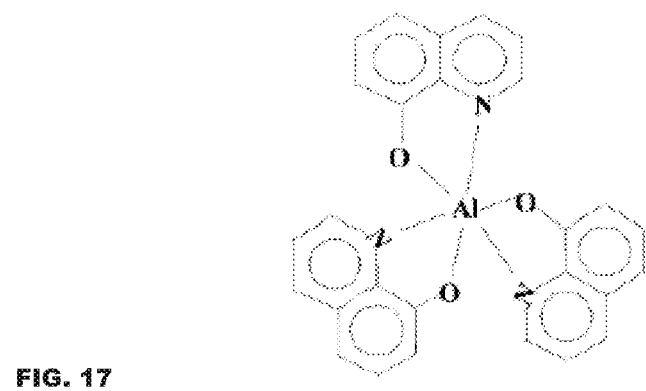
FIG. 17 shows the structure of a further embodiment of compound exhibiting XEOL, namely a tris-8-hydroxyquinolinealuminum complex. [Taken from: S. J. Naftel, P. Zhang, P.-S. Kim, and T. K. Sham, I. Coulthard, W. J. Antel, Jr., J. W. Freeland, and S. P. Frigo, M.-K. Fung and S. T. Lee, Y. F. Hu and B. W. Yates, Soft x-ray-excited luminescence and optical x-ray absorption fine structures of tris 8-hydroxyquinoline. Aluminum, Appl. Phys. Lett, 78, 1844, 2001]

Some examples of metal complexes exhibiting XEOL which can be used as energy modulation agent systems are shown in FIGS. 16 and 17. Such structures can be modified by replacing the metal atom with metal nanoparticles in order to fabricate a plasmonics-enhance PEPST probe. In the present invention, the experimental parameters including size, shape and metal type of the nano structure can be selected based upon the excitation radiation (NIR or X ray excitation), the photoactivation radiation (UVB), and/or the emission process from the energy modulation agent system (visible NIR).

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as $Er^{3+}$ doped $BaTiO_3$ nanoparticles and $Yb^{3+}$ doped $CsMnCl_3$) are suitable in various embodiments of the invention.

Further materials suitable as energy modulation agents include, but are not limited to, CdTe, CdSe, ZnO, CdS, $Y_2O_3$, MgS, CaS, SrS and BaS. Such materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}MnS_y$, $Ca_{1-x}Mn_xS_y$, $Ba_{1-x}Mn_xS_y$ and $Sr_{1-x}$, etc. (wherein, $0<x\leq1$ and $0<y\leq1$). Complex compounds of the above-described semiconductors are also contemplated for use in the invention—e.g. $(M_{1-z}N_z)_{1-x}Mn_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; $0<x\leq1$, $0<y\leq1$, $0<z\leq1$). Two examples of such complex compounds are $Zn_{0.4}Cd_{0.4}Mn_{0.2}S$ and $Zn_{0.9}Mn_{0.1}S_{0.8}Se_{0.2}$. Additional energy modulation materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nano particles, such as ZnS; Mn; Er; ZnSe; Mn, Er; MgS; Mn, Er; CaS; Mn, Er; ZnS; Mn, Yb; ZnSe; Mn,Yb; MgS; Mn, Yb; CaS; Mn,Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, . . . $0<z<1$, $o<q<1$).

Some nanoparticles such as $ZnS:Tb^{3+}$, $Er^3$; $ZnS:Tb^{3+}$; $Y_2O_3:Tb^{3+}$; $Y_2O_3:Tb^{3+}$, $Er^{3+}$; $ZnS:Mn^{2+}$; $ZnS:Mn,Er^{3+}$ are known in the art to function for both down-conversion luminescence and upconversion luminescence, and can thus be used in various embodiments of the present invention.

Principle of Plasmonics-Enhancement Effect of the PEPST Probe Using X-Ray Excitation One embodiment of the basic PEPST probe embodiment comprises PA molecules bound to an energy modulation agent and to plasmonic metal (gold) nanoparticles. First the metal nanoparticle can serve as a drug delivery platform (see previous discussion). Secondly, the metal nanoparticle can play 2 roles:

(1) Enhancement of the X-ray electromagnetic field
(2) Enhancement of the emission signal of the energy modulation agent system.

The X ray radiation, used to excite the energy modulation agent system, is amplified by the metal nanoparticle due to plasmon resonance. As a result the energy modulation agent system exhibits more emission light that is used to photoactivate the PA drug molecules (e.g., psoralens) and make them photoactive. In this case the metal nanoparticles are designed to exhibit strong plasmon resonance at or near the X ray wavelengths. The surface plasmon resonance effect amplifies the excitation light at the nanoparticles, resulting in increased photoactivation of the PA drug molecules and improved therapy efficiency. The plasmonics-enhanced mechanism can also be used with the other PEPST probes described above.

FIG. 18 illustrates the plasmonics-enhancement effect of the PEPST probe. X-ray used in medical diagnostic imaging has photon energies from approximately 10 to 150 keV, which is equivalent to wavelengths range from 1.2 to 0.0083 Angstroms. [$\lambda$ (Angstrom)=12.4/E (keV)]. Soft X ray can go to 10 nm. The dimension of plasmonics-active nanoparticles usually have dimensions on the order or less than the wavelengths of the radiation used. Note that the approximate atomic radius of gold is approximately 0.15 nanometers. At the limit, for gold the smallest "nanoparticle" size is 0.14 nm (only 1 gold atom). A nanoparticle with size in the hundreds of nm will have approximately $10^6$-$10^7$ gold atoms. Therefore, the range of gold nanoparticles discussed in this invention can range from 1-$10^7$ gold atoms.

The gold nanoparticles can also enhance the energy modulation agent emission signal, which is use to excite the PA molecule. For psoralens, this spectral range is in the UVB region (320-400 nm). Silver or gold nanoparticles, nanoshell and nanocaps have been fabricated to exhibit strong plasmon resonance in this region. FIG. 19 shows excitation and emission fluorescence spectra of a psoralen compound (8-methoxypsoralen).

PEPST Energy Modulation Agent-PA Probe with Detachable PA.

Figure 20A:
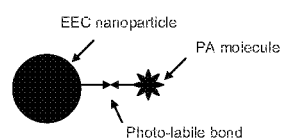
FIGS. 20A-20C are graphical representations of an embodiment of a PEPST energy modulation agent-PA system with detachable bond.
Figure 20B:
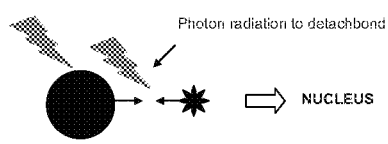
Figure 20C:
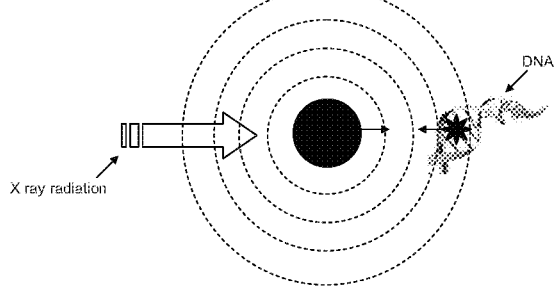
Figure 26A:
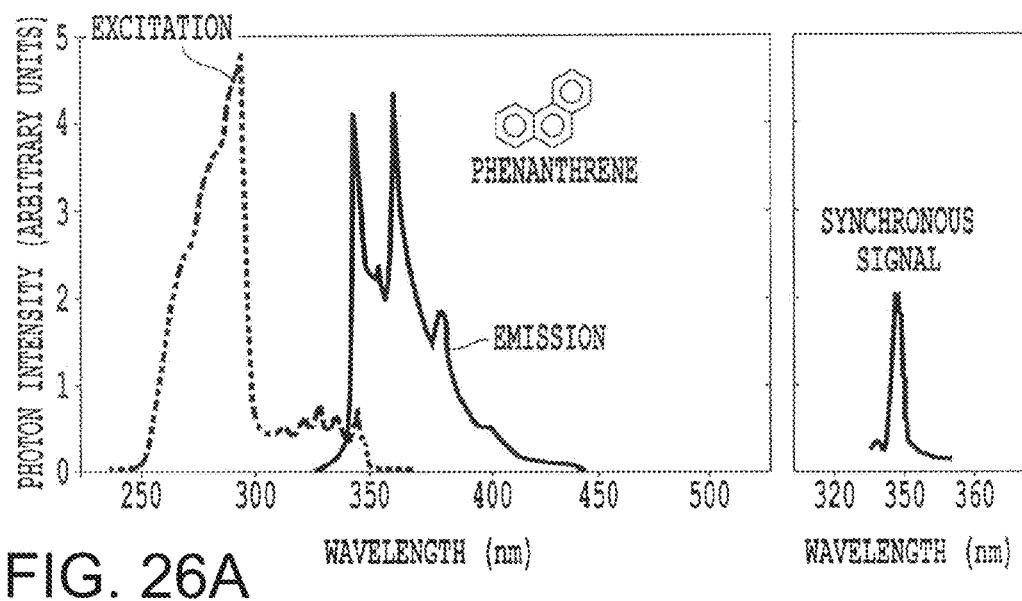
FIGS. 26A-E are graphical representations of fluorescence spectra of PAH compounds.
Figure 26B:
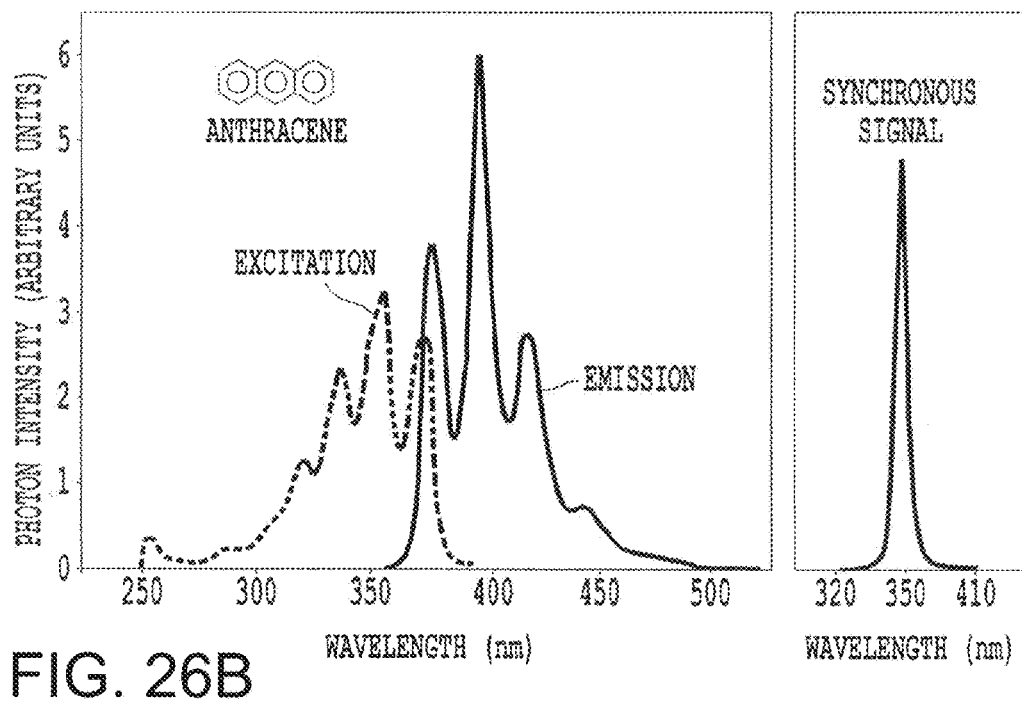
Figure 26C:
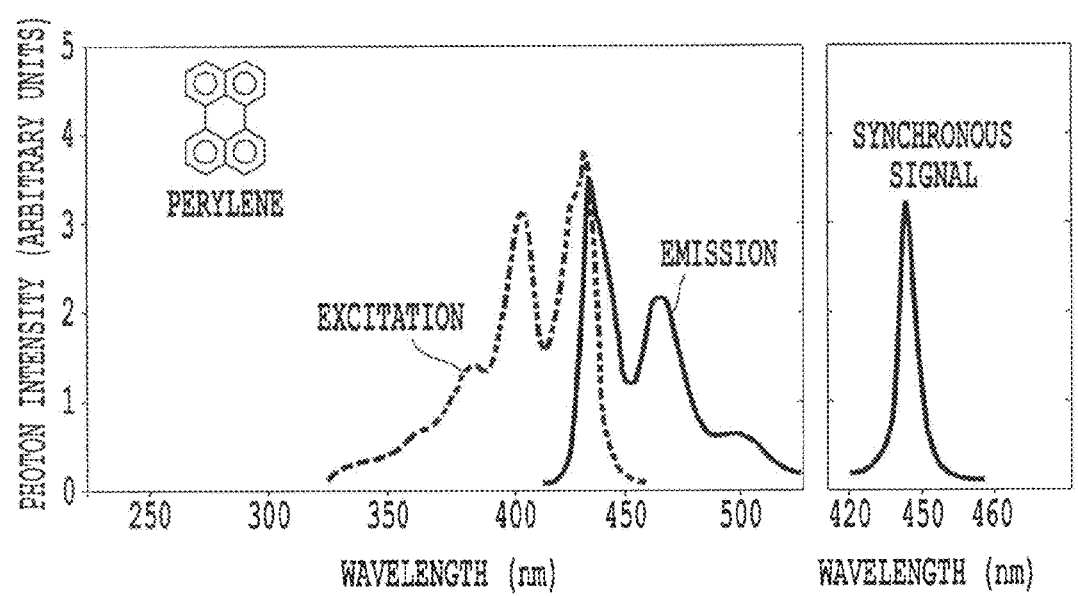
Figure 26D:
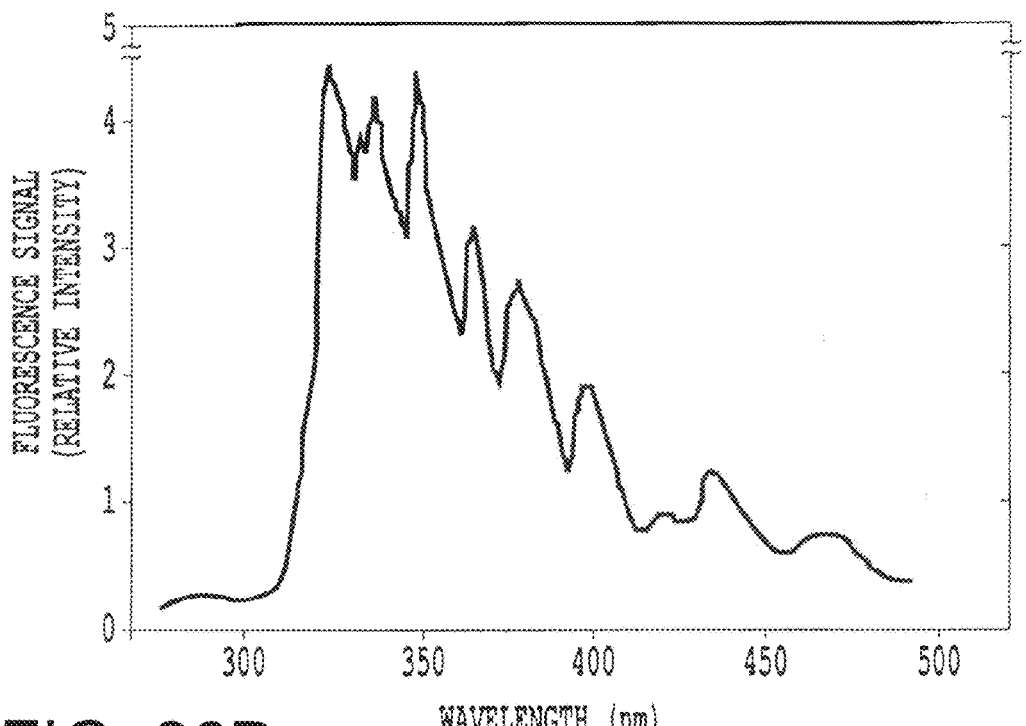
Figure 26E:
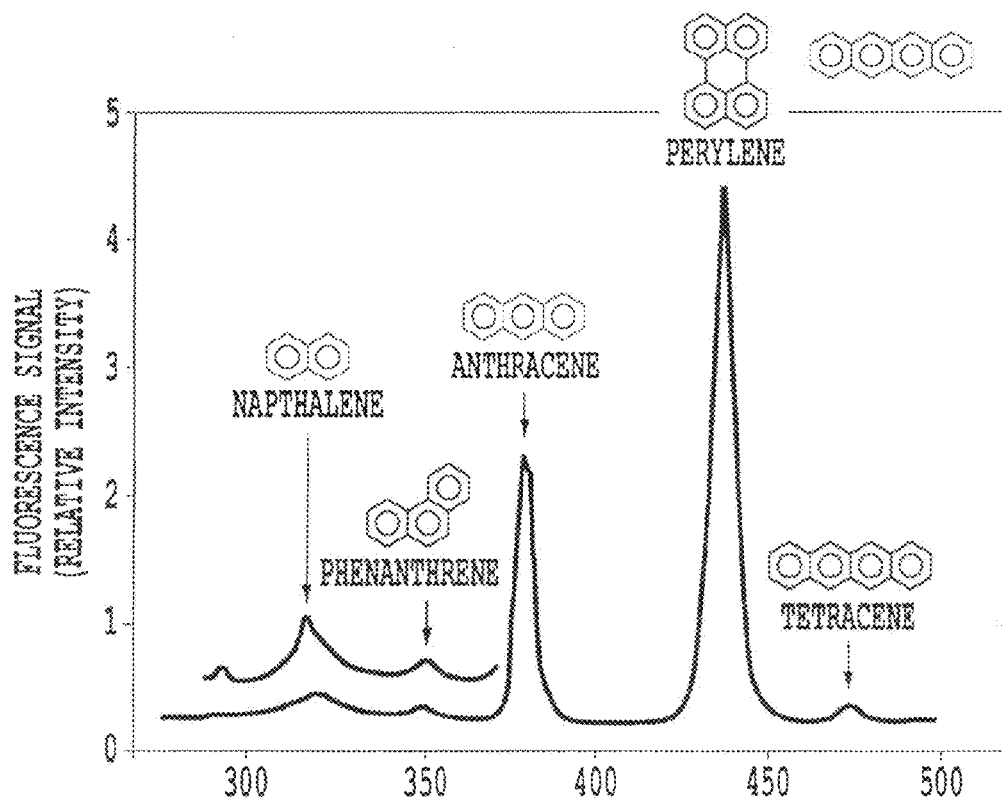

Some photoactive drugs require that the PA molecule to enter the nucleus. FIG. 20 shows an embodiment of a PEPST probe where the PA drug molecule is bound to the metal nanoparticles via a linker (FIG. 20A) that can be cut by photon radiation (FIG. 20B). Such a probe is useful for therapy modalities where the PA molecules have to enter the nucleus, e.g., psoralen molecules need to enter the nucleus of cells and intercalate onto DNA (FIG. 20C). Since it is more difficult for metal nanoparticles to enter the cell nucleus than for smaller molecules, it is preferable to use PEPST probes that have releasable PA molecules.

Suitable linkers for linking the PA drug molecule to the metal nanoparticles include, but are not limited to, labile chemical bonds that can be broken by remote energy excitation (from outside the body, e.g., MW, IR, photoacoustic energy, ultrasound energy, etc.), labile chemical bonds that can be broken by the chemical environment inside cells, antibody-antigen, nucleic acid linkers, biotin-streptavidin, etc.

Nanoparticle Chain for Dual Plasmonics Effect

As discussed previously, there is the need to develop nanoparticle systems that can have dual (or multi) plasmonics resonance modes. FIG. 21 illustrates an embodiment of the present invention PEPST probe having a chain of metal particles having different sizes and coupled to each other, which could exhibit such dual plasmonics-based enhancement. For example the parameters (size, metal type, structure, etc) of the larger nanoparticle (FIG. 21, left) can be tuned to NIR, VIS or UV light while the smaller particle (FIG. 21, right) can be tuned to X ray. There is also a coupling effect between these particles.

These nanoparticle chains are useful in providing plasmonics enhancement of both the incident radiation used (for example, x-ray activation of CdS) as well as plasmonics enhancement of the emitted radiation that will then activate the PA. Similar nanoparticles systems have been used as nanolens [*Self-Similar Chain of Metal Nanospheres as an Efficient Nanolens*, Kuiru Li, Mark I. Stockman, and David J. Bergman, *Physical Review Letter*, VOLUME 91, NUMBER 22, 227402-1, 2003].

Drug Delivery Platforms

Liposome Delivery of Energy Modulation Agent-PA Systems

The field of particle-based drug delivery is currently focused on two chemically distinct colloidal particles, liposomes and biodegradable polymers. Both delivery systems encapsulate the active drug. The drug is released from the particle as it lyses, in the case of lipsomes, or disintegrates, as described for biodegradable polymers. One embodiment of the present invention uses liposomal delivery of energy modulation agent-PA systems (e.g., gold nanoshells) for therapy. An exemplary embodiment is described below, but is not intended to be limiting to the specific lipids, nanoparticles or other components recited, but is merely for exemplary purposes:

Preparation of Liposomes.

The liposome preparation method is adapted from Hölig et. al Hölig, P., Bach, M., Völkel, T., Nande, T., Hoffmann, S., Müller, R., and Kontermann, R. E., Novel *RGD lipopeptides for the targeting of liposomes to integrin-expressing endothelial and melanoma cells*. Protein Engineering Design and Selection, 2004. 17(5): p. 433-441]. Briefly, the lipids PEG-DPPE, PC, and Rh-DPPE are mixed in chloroform in a round bottom flask and evaporated (Hieroglyph Rotary Evaporator, Rose Scientific Ltd., Edmonton, Alberta, Canada) to eliminate chloroform. The dry film is dehydrated into aqueous phase with using PBS solution. A dry lipid film is prepared by rotary evaporation from a mixture of PC, cholesterol, and PEG-DPPE and then hydrated into aqueous phase using PBS. The mixture is vigorously mixed by overtaxing and bath solicited (Instrument, Company) and the suspension extruded through polycarbonate filter using Liposofast apparatus (Avestin Inc., Ottawa, ON, Canada) (pore-size 0.8 μm). Preparation of liposomes is performed as follows; 0.1 mmol of PC is dispersed in 8 ml of chloroform and supplemented with 0.5 mol of PEG-DPPE in 20 ml of chloroform. 0.3 mmol rhodamine-labeled phosphatidylethanolamine (Rh-DPPE) is then incorporated into the liposomes. The organic solvents are then removed by rotary evaporation at 35° C. for 2 h leaving a dry lipid film. Gold nanoshells are encapsulated into liposomes by adding them to the PBS hydration buffer and successively into the dry lipid film. This mixture is emulsified in a temperature controlled sonicator for 30 minutes at 35° C. followed by vortexing for 5 min. Encapsulated gold nanoshells, are separated from unencapsulated gold nanoshells by gentle centrifugation for 5 minutes at 2400 r.p.m (1200 g). The resulting multilamellar vesicles suspension is extruded through polycarbonate filter using Liposofast apparatus (Avestin Inc., Ottawa, ON, Canada) (pore-size 0.8 μm). The aqueous mixture is obtained and stored at 4° C.

Fabrication of Gold Nanoparticles:

The Frens method [Frens, G., *Controlled nucleation for the regulation of the particle size in monodisperse gold solutions*. Nature (London) Phys Sci, 1973. 241: p. 20-22] can be used in the present invention to synthesize a solution of gold nanoparticles ranging in diameter from 8-10 nm. Briefly, $5.0 \times 10^{-6}$ mol of $HAuCl_4$ is dissolved in 19 ml of deionized water producing a faint yellowish solution. This solution is heated with vigorous stirring in a rotary evaporator for 45 minutes. 1 ml of 0.5% sodium citrate solution is added and the solution is stirred for an additional 30 minutes. The color of the solution gradually changed from the initial faint yellowish to clear, grey, purple and finally a tantalizing wine-red color similar to merlot. The sodium citrate used serves in a dual capacity, first acting as a reducing agent, and second, producing negative citrate ions that are adsorbed onto the gold nanoparticles introducing surface charge that repels the particles and preventing nanocluster formation.

Preparation and Internalization of Liposome-Encapsulated Gold Nanoshells:

Liposome-encapsulated gold nanoshells are incubated with MCF-7 cells grown on partitioned cover-slips for intracellular delivery. This is done by adding 10 μl of liposome-encapsulated gold nanoshells per 1 ml of cell culture medium. This is incubated for 30 minutes in a humidified (86% RH) incubator at 37° C. and 5% $CO_2$. This cell is used for localization studies; to track the rhodamine-DPPE-labeled liposomes into the cytoplasm of the MCF-7 cell. After incubation, the cells grown on cover-slips are washed three times in cold PBS and fixed using 3.7% formaldehyde in PBS. Rhodamine staining by rhodamine-DPPE-labeled liposomes is analyzed using a Nikon Diaphot 300 inverted microscope (Nikon, Inc., Melville, N.Y.).

Non-Invasive Cleavage of the Drug System In Vivo

After delivery of the drug system into the cell, there is sometimes the need to have the PA system (e.g. psoralen) in the nucleus in order to interact with DNA. If the PA is still linked to the energy modulation agent, both of them have to be transported into the nucleus. In the case with gold nanoparticles as the energy modulation agent system, there are several methods to incubate cells in vitro. For in vivo applications, one can link the PA to the gold nanoparticles using a chemical linkage that can be released (or cut) using non-invasive methods such as infrared, microwave, or ultrasound waves. An example of linkage is through a chemical bond or through a bioreceptor, such as an antibody. In this case, the PA is the antigen molecule bound to the energy modulation agent system that has an antibody targeted to the PA.

When the energy modulation agent-Ab-PA enters the cell, the PA molecules can be released from the energy modulation agent Ab system. To release the PA molecule from the antibody, chemical reagents can be used to cleave the binding between antibody and antigen, thus regenerating the biosensor [Vo-Dinh et al, 1988]. This chemical procedure is simple but is not practical inside a cell due to possible denaturation of the cell by the chemical. In previous studies, it has been demonstrated that the gentle but effective MHz-range ultrasound has the capability to release antigen molecules from the antibody-energy modulation agent system [Moreno-Bondi, M., Mobley, J., and Vo-Dinh, T., "Regenerable Antibody-based Biosensor for Breast Cancer," J. Biomedical Optics, 5, 350-354 (2000)]. Thus, an alternative embodiment is to use gentle ultrasonic radiation (non-invasively) to remove the PA (antigen) from the antibody at the energy modulation agent system.

In a preferred embodiment, the PA molecule is bound to the energy modulation agent by a chemically labile bond [Jon A. Wolff, and David B. Rozema, Breaking the Bonds: Non-viral Vectors Become Chemically Dynamic, *Molecular Therapy* (2007) 16(1), 8-15]. A promising method of improving the efficacy of this approach is to create synthetic vehicles (SVs) that are chemically dynamic, so that delivery is enabled by the cleavage of chemical bonds upon exposure to various physiological environments or external stimuli. An example of this approach is the use of masked endosomolytic agents (MEAs) that improve the release of nucleic acids from endosomes, a key step during transport. When the MEA enters the acidic environment of the endosome, a pH-labile bond is broken, releasing the agent's endosomolytic capability.

Use of Ferritin and Apoferritin as Targeted Drug Delivery

Another embodiment to deliver the energy modulation agent-PA drugs involves the use of ferritin and apoferritin compounds. There is increasing interest in ligand-receptor-mediated delivery systems due to their non-immunogenic and site-specific targeting potential to the ligand-specific bio-sites. Platinum anticancer drug have been encapsulated in apoferritin [Zhen Yang, Xiaoyong Wang, Huajia Diao, Junfeng Zhang, Hongyan Li, Hongzhe Sun and Zijian Guo, Encapsulation of platinum anticancer drugs by apoferritin, *Chem. Commun.* 33, 2007, 3453-3455]. Ferritin, the principal iron storage molecule in a wide variety of organisms, can also be used as a vehicle for targeted drug delivery. It contains a hollow protein shell, apoferritin, which can contain up to its own weight of hydrous ferric oxide-phosphate as a microcrystalline micelle. The 24 subunits of ferritin assemble automatically to form a hollow protein cage with internal and external diameters of 8 and 12 nm, respectively. Eight hydrophilic channels of about 0.4 nm, formed at the intersections of subunits, penetrate the protein shell and lead to the protein cavity. A variety of species such as gadolinium ($Gd^{3+}$) contrast agents, desfenioxamine B, metal ions, and nanoparticles of iron salts can be accommodated in the cage of apoferritin. Various metals such as iron, nickel, chromium and other materials have been incorporated into apoferritin [Iron incorporation into apoferritin. The role of apoferritin as a ferroxidase, The Journal of Biological Chemistry [0021-9258] Bakker yr:1986 vol:261 iss:28 pg:13182-5; Mitsuhiro Okuda[1], Kenji Iwahori[2], Ichiro Yamashita[2], Hideyuki Yoshimura[1*], Fabrication of nickel and chromium nanoparticles using the protein cage of apoferritin, Biotechnology Bioengineering, Volume 84, Issue 2, Pages 187-194]. Zinc selenide nanoparticles (ZnSe NPs) were synthesized in the cavity of the cage-shaped protein apoferritin by designing a slow chemical reaction system, which employs tetraaminezinc ion and selenourea. The chemical synthesis of ZnSe NPs was realized in a spatially selective manner from an aqueous solution, and ZnSe cores were formed in almost all apoferritin cavities with little bulk precipitation [Kenji Iwahori, Keiko Yoshizawa, Masahiro Muraoka, and Ichiro Yamashita, Fabrication of ZnSe Nanoparticles in the Apoferritin Cavity by Designing a Slow Chemical Reaction System, Inorg. Chem., 44 (18), 6393-6400, 2005].

A simple method for synthesizing gold nanoparticles stabilized by horse spleen apoferritin (HSAF) is reported using $NaBH_4$ or 3-(N-morpholino)propanesulfonic acid (MOPS) as the reducing agent [Lei Zhang, Joe Swift, Christopher A. Butts, Vijay Yerubandi and Ivan J. Dmochowski, Structure and activity of apoferritin-stabilized gold nanoparticles, Journal of Inorganic Biochemistry, Vol. 101, 1719-1729, 2007]. Gold sulfite ($Au_2S$) nanoparticles were prepared in the cavity of the cage-shaped protein, apoferritin. Apoferritin has a cavity, 7 nm in diameter, and the diameter of fabricated $Au_2S$ nanoparticles is about the same size with the cavity and size dispersion was small. [Keiko Yoshizawa, Kenji Iwahori, Kenji Sugimoto and Ichiro Yamashita, Fabrication of Gold Sulfide Nanoparticles Using the Protein Cage of Apoferritin, Chemistry Letters, Vol. 35 (2006), No. 10 p.1192]. Thus, in a preferred embodiment, the PA or energy modulation agent-PA compounds are encapsulated inside the apoferrtin shells.

Use of Ferritin and Apoferritin as Enhanced Targeting Agents

It was reported that ferritin could be internalized by some tumor tissues, and the internalization was associated with the membrane-specific receptors [S. Fargion, P. Arosio, A. L. Fracanzoni, V. Cislaghi, S. Levi, A. Cozzi, A Piperno and A. G. Firelli, *Blood,* 1988, 71, 753-757; P. C. Adams, L. W. Powell and J. W. Halliday, *Hepatology,* 1988, 8, 719-721]. Previous studies have shown that ferritin-binding sites and the endocytosis of ferritin have been identified in neoplastic cells [M. S. Bretscher and J. N. Thomson, *EMBO J.,* 1983, 2, 599-603]. Ferritin receptors have the potential for use in the delivery of anticancer drugs into the brain [S. W. Hulet, S. Powers and J. R. Connor, *J. Neurol. Sci.,* 1999, 165, 48-55]. In one embodiment, the present invention uses ferritin or apoferritin to both encapsulate PA and energy modulation agent-PA systems and also target tumor cells selectively for enhanced drug delivery and subsequent phototherapy. In this case no additional bioreactors are needed.

FIG. 22 schematically illustrates the use of encapsulated photoactive agents (FIG. 22A) for delivery into tissue and subsequent release of the photoactive drugs after the encapsulated systems enter the cell. Note the encapsulated system can have a bioreceptor for selective tumor targeting (FIG. 2213). Once inside the cell, the capsule shell (e.g., liposomes, apoferritin, etc.) can be broken (FIG. 22C) using non-invasive excitation (e.g., ultrasound, RF, microwave, IR, etc) in order to release the photoactive molecules that can get into the nucleus and bind to DNA (FIG. 22D).

Non-Invasive Phototherapy Using PEPST Modality

FIG. 23 illustrates the basic operating principle of the PEPST modality. The PEPST photoactive drug molecules are given to a patient by oral ingestion, skin application, or by intravenous injection. The PEP ST drugs travel through the blood stream inside the body towards the targeted tumor (either via passive or active targeting strategies). If the disease is systematic in nature a photon radiation at suitable wavelengths is used to irradiate the skin of the patient, the light being selected to penetrate deep inside tissue (e.g., NIR or X ray). For solid tumors, the radiation light source is directed at the tumor. Subsequently a treatment procedure can be initiated using delivery of energy into the tumor site. One or several light sources may be used as described in the previous sections. One embodiment of therapy comprises sending NIR radiation using an NIR laser through focusing optics. Focused beams of other radiation types, including but not limited to X ray, microwave, radio waves, etc. can also be used and will depend upon the treatment modalities used.

Exciton-Plasmon Enhanced Phototherapy (EPEP)

Basic Principle of Exciton-Induced Phototherapy

Excitons in Solid Materials

Excitons are often defined as "quasiparticles" inside a solid material. In solid materials, such as semiconductors, molecular crystals and conjugated organic materials, light excitation at suitable wavelength (such as X ray, UV and visible radiation, etc) can excite electrons from the valence band to the conduction band. Through the Coulomb interaction, this newly formed conduction electron is attracted, to the positively charged hole it left behind in the valence band. As a result, the electron and hole together form a bound state called an exciton. (Note that this neutral bound complex is a "quasiparticle" that can behave as a boson—a particle with integer spin which obeys Bose-Einstein statistics; when the temperature of a boson gas drops below a certain value, a large number of bosons 'condense' into a single quantum state—this is a Bose-Einstein condensate (BEC). Exciton production is involved in X-ray excitation of a solid material. Wide band-gap materials are often employed for transformation of the x-ray to ultraviolet/visible photons in the fabrication of scintillators and phosphors [Martin Nikl, *Scintillation detectors for x-rays, Meas. Sci. Technol.* 17 (2006) R37-R54]. The theory of excitons is well known in materials research and in the fabrication and applications of semiconductors and other materials. However, to the present inventors' knowledge, the use of excitons and the design of energy modulation agent materials based on exciton tunability for phototherapy have not been reported.

During the initial conversion a multi-step interaction of a high-energy X-ray photon with the lattice of the scintillator material occurs through the photoelectric effect and Compton scattering effect; for X-ray excitation below 100 keV photon energy the photoelectric effect is the main process. Many excitons (i.e., electron-hole pairs) are produced and thermally distributed in the conduction bands (electrons) and valence bands (holes). This first process occurs within less than 1 ps. In the subsequent transport process, the excitons migrate through the material where repeated trapping at defects may occur, leading to energy losses due to nonradiative recombination, etc. The final stage, luminescence, consists in consecutive trapping of the electron-hole pairs at the luminescent centers and their radiative recombination. The electron-hole pairs can be trapped at the defects and recombine, producing luminescent. Luminescent dopants can also be used as traps for exciton.

Exciton Traps

Exciton traps can be produced using impurities in the crystal host matrix. In impure crystals with dipolar guest molecules the electron trap states may arise when electron is localized on a neighbor of the impurity molecule. Such traps have been observed in anthracene doped with carbazole [Kadshchuk, A. K., Ostapenko, N Skryshevskii, Yu. A., Sugakov, V. I. and Susokolova, T. O., *Mol. Cryst. and Liq. Cryst.*, 201, 167 (1991)]. The formation of these traps is due to the interaction of the dipole moment of the impurity with charge carrier. When the concentration of the dopant (or impurities) is increased, spectra exhibit additional structure of spectrum due to the trapping of carriers on clusters of impurity molecules. Sometimes, impurities and dopants are not required: the electron or exciton can also be trapped on a structural defect in such crystals due to the electrostatic interaction with reoriented dipole moment of disturbed crystal molecules [S. V. Izvekov, V. I. Sugakov, *Exciton and Electron Traps on Structural Defects in Molecular Crystals with Dipolar Molecules, Physica Scripta.* Vol. T66, 255-257, 1996]. One can design structural defects in molecular crystals that serve as exiton traps. The development of GaAs/AlGaAs nanostructures and use of nanofabrication technologies can design engineered exciton traps with novel quantum mechanical properties in materials Design, Fabrication and Operation of EIP Probes FIG. 25 shows various embodiments of EIP probes that can be designed:

(A) probe comprising PA molecules bound (through a linker, which can be fixed or detachable) to an energy modulation agent particle that can produce excitons under radiative excitation at a suitable wavelength (e.g., X-ray). In this preferred embodiment, the energy modulation agent materials have structural defects that serve as traps for excitons.

(B) probe comprising PA molecules bound (through a linker, which can be fixed or detachable) to an energy modulation agent particle that can produce excitons under radiative excitation at a suitable wavelength (e.g., X-ray). In this preferred embodiment, the energy modulation agent materials have impurities or dopant molecules that serve as traps for excitons.

EIP Probes with Tunable Emission:

The embodiment in probes B provide the capability to tune the energy conversion from an X ray excitation source into a wavelength of interest to excite the PA molecules. In 1976, D'Silva et al demonstrated that polynuclear aromatic hydrocarbons (PAH) molecules doped in a frozen n-alkane solids could be excited by X-ray and produce luminescence at visible wavelengths characteristics of their luminescence spectra. [A. P. D'Silva, G. J. Oestreich, and V. A. Fassel, X-ray excited optical luminescence of polynuclear aromatic hydrocarbons, Anal. Chem.; 1976; 48(6) pp 915-917]. Tunable EIP probes can be designed to contain such luminescent dopants such as highly luminescent PAHs exhibiting luminescence emission in the range of 300-400 nm suitable to activate psoralen. A preferred embodiment of the EIP with tunable emission comprises a solid matrix (semiconductors, glass, quartz, conjugated polymers, etc) doped with naphthalene, phenanthrene, pyrene or other compounds exhibiting luminescence (fluorescence) in the 300-400 nm range [T. Vo-Dinh, *Multicomponent analysis by synchronous luminescence spectrometry, Anal. Chem.*; 1978; 50(3) pp 396-401]. See FIG. 26. The EEC matrix could be a semiconductor material, preferably transparent at optical wavelength of interest (excitation and emission).

Figure 27:
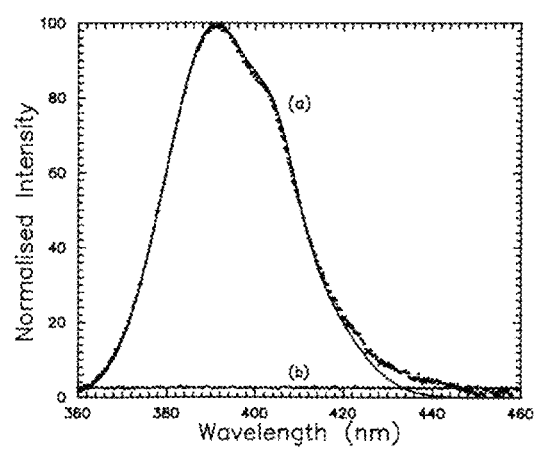
FIG. 27 is a graph showing the XEOL of Eu doped in BaFBr matrix. [Source: N Subramanian et al, X-ray excited optical luminescence, photoluminescence, photostimulated luminescence and x-ray photoemission spectroscopy studies on BaFBr:Eu J. Phys.: Condens. Matter 9 4769-4780, 1997]}

Other dopant species such as rare earth materials can also be used as dopants. FIG. 27 shows the X ray excitation optical luminescence (XEOL) of Europium doped in a matrix of BaFBr, emitting at 370-420 nm. U.S. Patent Application Publication No. 2007/0063154 (hereby incorporated by reference) describes these and other nanocomposite materials (and methods of making them) suitable for XEOL.

FIG. 28 shows various embodiments of EIP probes that can be designed:

(A) probe comprising PA molecules bound around the energy modulation agent particle or embedded in a shell around an energy modulation agent particle that can produce excitons under radiative excitation at a suitable wavelength (e.g., X-ray). In this preferred embodiment, the energy modulation agent materials has structural defects that serve as traps for excitons.

(B) probe comprising PA molecules bound around the energy modulation agent particle or embedded in a shell around an energy modulation agent particle that can produce excitons under radiative excitation at a suitable wavelength (e.g., X-ray). In this preferred embodiment, the energy modulation agent materials have impurities or dopant molecules that serve as traps for excitons.

Principle of Exciton-Plasmon Enhanced Phototherapy (EPEP)

There is recent interest in an advanced photophysical concept involving quantum optical coupling between electronic states (excitons), photons and enhanced electromagnetic fields (plasmons). Such a concept involving coupling between excitons and plasmons can be used to enhance a phototherapy modality, referred to as Exciton-Plasmon Enhanced Phototherapy (EPEP).

A fundamental key concept in photophysics is the formation of new quasiparticles from admixtures of strongly-coupled states. Such mixed states can have unusual properties possessed by neither original particle. The coupling between excitons and plasmons can be either weak or strong. When the light-matter interaction cannot be considered as a perturbation, the system is in the strong coupling regime. Bellesa et al showed a strong coupling between a surface plasmon (SP) mode and organic excitons occurs; the organic semiconductor used is a concentrated cyanine dye in a polymer matrix deposited on a silver film [Ref J. Bellessa, * C. Bonnand, and J. C. Plenet, J. Mugnier, *Strong Coupling between Surface Plasmons and Excitons in an Organic Semiconductor*, Phys. Rev. Lett, 93 (3), 036404-1, 2004]. Govorov et al describe the photophysical properties of excitons in hybrid complexes consisting of semiconductor and metal nanoparticles. The interaction between individual nanoparticles can produce an enhancement or suppression of emission. Enhanced emission comes from electric field amplified by the plasmon resonance, whereas emission suppression is a result of energy transfer from semiconductor to metal nanoparticles. [Alexander O. Govorov, *, † Garnett W. Bryant, Wei Zhang, † Timur Skeini, † Jaebeom Lee, § Nicholas A. Kotov, § Joseph M Slocik, | and Rajesh R. Naik|, *Exciton-Plasmon Interaction and Hybrid Excitons in Semiconductor-Metal Nanoparticle Assemblies*, Nano Lett., Vol. 6, No. 5, 984, 2006]. Bondarev et al also described a theory for the interactions between excitonic states and surface electromagnetic modes in small-diameter (<1 nm) semiconducting single-walled carbon nanotubes (CNs). [I. V. Bondarev, K. Tatur and L. M. Woods, *Strong exciton-plasmon coupling in semiconducting carbon nanotubes*].

Fedutik et al reported about the synthesis and optical properties of a composite metal-insulator-semiconductor nanowire system which consists of a wet-chemically grown silver wire core surrounded by a $SiO_2$ shell of controlled thickness, followed by an outer shell of highly luminescent CdSe nanocrystals [Yuri Fedutik, †Vasily Temnov, † Ulrike Woggon, † Elena Ustinovich, ‡ and Mikhail Artemyev‡, *Exciton-Plasmon Interaction in a Composite Metal-Insulator-Semiconductor Nanowire System*, J. Am. Chem. Soc., 129 (48), 14939-14945, 2007]. For a $SiO_2$ spacer thickness of ~15 nm, they observed an efficient excitation of surface plasmons by excitonic emission of CdSe nanocrystals. For small d, well below 10 nm, the emission is strongly suppressed (PL quenching), in agreement with the expected dominance of the dipole-dipole interaction with the damped mirror dipole [G. W. Ford and W. H. Weber, *Electromagnetic interactions of molecules with metal surfaces,"* Phys. Rep. 113, 195-287 (1984)]. For nanowire lengths up to ~10 µm, the composite metal-insulator-semiconductor nanowires $((Ag)SiO_2)CdSe$ act as a waveguide for 1D-surface plasmons at optical frequencies with efficient photon out coupling at the nanowire tips, which is promising for efficient exciton-plasmon-photon conversion and surface plasmon guiding on a submicron scale in the visible spectral range.

Experiments on colloidal solutions of Ag nanoparticles covered with J-aggregates demonstrated the possibility of using the strong scattering cross section and the enhanced field associated with surface plasmon to generate stimulated emission from J-aggregate excitons with very low excitation powers. [Gregory A. Wurtz, * Paul R. Evans, William Hendren, Ronald Atkinson, Wayne Dickson, Robert J. Pollard, and Anatoly V. Zayats, *Molecular Plasmonics with Tunable Exciton-Plasmon Coupling Strength in J-Aggregate Hybridized Au Nanorod Assemblies*, Nano Lett., Vol. 7, No. 5, 1297, 2007]. Their coupling to surface plasmons excitations therefore provides a particularly attractive approach for creating low-powered optical devices. This process can lead to efficient X-ray coupling for phototherapy. In addition, the coupling of J-aggregates with plasmonics structures presents genuine fundamental interest in the creation of mixed plasmon-exciton states.

Design, Fabrication and Operation of EPEP Probes

FIG. 29 shows various embodiments of EPEP probes of the present invention showing the exciton-plasmon coupling:

(A) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticle covered with a nanoshell of silica (or other dielectric material). The silica layer (or nanoshell) (see FIG. 24A and FIG. 24B; layer nanoshell in white between energy modulation material and metal nanostructures) is designed to prevent quenching of the luminescence light emitted by the energy modulation agent particle excited by X-ray. The metal nanoparticle (Au, Ag, etc) is designed to induce plasmons that enhance the X ray excitation that subsequently leads to an increase in the energy modulation agent light emission, ultimately enhancing the efficiency of photoactivation, i.e. phototherapy. The structure of the nanoparticle can also be designed such that the plasmonics effect also enhances the energy modulation agent emission light. These processes are due to strong coupling between excitons (in the energy modulation agent materials and plasmons in the metal nanoparticles; and (B) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticle via a spacer (linker). The spacer is designed to prevent quenching of the luminescence light emitted by the energy modulation agent particle excited by X-ray.

FIG. 30 shows yet further embodiments of EPEP probes of the present invention:

(A) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is covered with a nanoshell of silica (or other dielectric material), which is covered by a layer of separate nanostructures (nano islands, nanorods, nanocubes, etc. . . . ) of metal (Au, Ag). The silica layer (or other dielectric material) is designed to prevent quenching of the luminescence light emitted by the EEC (also referred to as energy modulation agent) particle excited by X-ray. The metal nanostructures (Au, Ag, etc) are designed to induce plasmons that enhance the X ray excitation that subsequently leads to an increase in the EEC light emission, ultimately enhancing the efficiency of photoactivation, i.e. phototherapy. The structure of the nanoparticle can also be designed such that the plasmonics effect also enhance the energy modulation agent emission light. These processes are due to strong coupling between excitons (in the energy modulation agent materials and plasmons in the metal nanostructures).

(B) probe comprising a group of PA molecules in a particle bound (through a linker, which can be fixed or detachable) to an energy modulation agent particle that can produce excitons under radiative excitation at a suitable wavelength (e.g., X-ray). The PA-containing particle is covered with a layer of metallic nanostructures (Au, Ag). The metal nanostructures (Au, Ag, etc) are designed to induce plasmons that enhance the energy modulation agent light emission, ultimately enhancing the efficiency of photoactivation, i.e. phototherapy.

(C) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is covered with a nanoshell of silica (or other dielectric material), which is covered by a layer of metallic nanostructures (Au, Ag). The silica layer (or other dielectric material) is designed to prevent quenching of the luminescence light emitted by the energy modulation agent particle excited by X-ray. The metal nanostructures (Au, Ag, etc) are designed to induce plasmons that enhance the X ray excitation that subsequently leads to an increase in the energy modulation agent light emission, ultimately enhancing the efficiency of photoactivation, i.e. phototherapy. In addition, the PA-containing particle is covered with a layer of metallic nanostructures (Au, Ag). The metal nanostructures (Au, Ag, etc) are designed to induce plasmons that enhance the EEC light emission, ultimately enhancing the efficiency of photoactivation, i.e. phototherapy.

Hybrid EPEP Nano-Superstructures

EPEP probes can also comprise hybrid self-assembled superstructures made of biological and abiotic nanoscale components, which can offer versatile molecular constructs with a spectrum of unique electronic, surface properties and photospectral properties for use in phototherapy.

Biopolymers and nanoparticles can be integrated in superstructures, which offer unique functionalities because the physical properties of inorganic nanomaterials and the chemical flexibility/specificity of polymers can be used. Noteworthy are complex systems combining two types of excitations common in nanomaterials, such as excitons and plasmons leading to coupled excitations. Molecular constructs comprising building blocks including metal, semiconductor nanoparticles (NPs), nanorods (NRs) or nanowires (NWs) can produce EPEP probes with an assortment of photonic properties and enhancement interactions that are fundamentally important for the field of phototherapy. Some examples of assemblies of some NW nanostructures and NPs have been reported in biosensing. Nanoscale superstructures made from CdTe nanowires (NWs) and metal nanoparticles (NPs) are prepared via bioconjugation reactions. Prototypical biomolecules, such as D-biotin and streptavidin pair, were utilized to connect NPs and NWs in solution. It was found that Au NPs form a dense shell around a CdTe NW. The superstructure demonstrated unusual optical effects related to the long-distance interaction of the semiconductor and noble metal nanocolloids. The NWNP complex showed 5-fold enhancement of luminescence intensity and a blue shift of the emission peak as compared to unconjugated NW. [Jaebeom Lee, † Alexander O. Govorov, † John Dulka, † and Nicholas A. Kotov*, †, *Bioconjugates of CdTe Nanowires and Au Nanoparticles: Plasmon-Exciton Interactions, Luminescence Enhancement, and Collective Effects*, Nano Lett., Vol, 4, No. 12, 2323, 2004].

To the present inventors' knowledge, these advanced concepts have not been applied to phototherapy and EPEP probes comprising superstructures from NPs, NRs and NWs are still a new unexplored territory of phototherapy.

FIG. 31 shows various embodiments of EPEP probes of the present invention comprising superstructures of NPs, NWs and NRs.

(A) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanowire (or nanorod) covered with a nanoshell cylinder of silica (or other dielectric material). The silica nanoshells cylinder is designed to prevent quenching of the luminescence light emitted by the energy modulation agent particle excited by X-ray. The metal nanoparticle (Au, Ag, etc) is designed to induce plasmons that enhance the X ray excitation that subsequently leads to an increase in the energy modulation agent light emission, ultimately enhancing the efficiency of photoactivation, i.e. phototherapy. The structure of the nanoparticle can also be designed such that the plasmonics effect and/or the exciton-plasmon coupling (EPC) effect also enhances the energy modulation agent emission light. These processes are due to strong coupling between excitons (in the energy modulation agent materials and plasmons in the metal nanoparticles; and (B) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticles via a spacer (linker). The spacer is designed to prevent quenching of the luminescence light emitted by the energy modulation agent particle excited by X-ray. Same effect as above in (A)

FIG. 32 shows another set of embodiments of EPEP probes of the present invention comprising superstructures of NPs, NWs and NRs and bioreceptors (antibodies, DNA, surface cell receptors, etc.). The use of bioreceptors to target tumor cells has been discussed previously above in relation to PEPST probes. Note that in this embodiment the PA molecules are attached along the NW axis in order to be excited by the emitting light form the NWs.

FIG. 33 shows another embodiment of EPEP probes of the present invention comprising superstructures of NPs linked to multiple NWs.

For some embodiments, by adding metal nanostructures designed to interact specifically with the excitons in the energy modulation agent system, there are significant improvements:

(1) an additional radiative pathway from exciton to photon conversion is introduced (2) the metal nanostructures can be designed to amplify (due to the plasmonics effect) the excitation radiation (e.g., X-ray) and/or the emission radiation (e.g, UV or visible) to excite the photo-active (PA) molecule, thereby enhancing the PA effectiveness.

Various metallic nanostructures that can be used in EPEP probe embodiments of the present invention are the same as those illustrated in FIG. 9 for the PEPST probes.

EPEP Probes with Microresonators

In a preferred embodiment the energy modulation agent system can be designed to serve also as a microresonator having micron or submicron size. Lipson et al described a resonant microcavity and, more particularly, to a resonant microcavity which produces a strong light-matter interaction [M Lipson; L. C. Kimerling; *Lionel C, Resonant microcavities*, U.S. Pat. No. 6,627,923, 2000]. A resonant microcavity, typically, is formed in a substrate, such as silicon, and has dimensions that are on the order of microns or fractions of microns. The resonant microcavity contains optically-active matter (i.e., luminescent material) and reflectors which confine light in the optically-active matter. The confined light interacts with the optically-active matter to produce a light-matter interaction. The light-matter interaction in a microcavity can be characterized as strong or weak. Weak interactions do not alter energy levels in the matter, whereas strong interactions alter energy levels in the matter. In strong light-matter interaction arrangements, the confined light can be made to resonate with these energy level transitions to change properties of the microcavity.

Experimental Methods

Preparation of Nanoparticles (Ag, Au)

There many methods to prepare metal nanoparticles for EPEP or PEPST probes. Procedures for preparing gold and silver colloids include electroexplosion, electrodeposition, gas phase condensation, electrochemical methods, and solution-phase chemical methods. Although the methodologies for preparing homogeneous-sized spherical colloidal gold populations 2-40 nm in diameter are well known [N. R. Jana, L. Gearheart and C. J. Murphy, *Seeding growth for size control of 5-40 nm diameter gold nanoparticles. Langmuir* 17 (2001), pp. 6782-6786], and particles of this size are commercially available. An effective chemical reduction method for preparing populations of silver particles (with homogeneous optical scattering properties) or gold particles (with improved control of size and shape monodispersity) is based on the use of small-diameter uniform-sized gold particles as nucleation centers for the further growth of silver or gold layers.

A widely used approach involves citrate reduction of a gold salt to produce 12-20 nm size gold particles with a relatively narrow size distribution. The commonly used method for producing smaller gold particles was developed by Brust et al [Brust, M; Walker, M; Bethell, D.; Schiffrin, D. I; Whyman, R. *Chem. Commun.* 1994, 801]. This method is based on borohydride reduction of gold salt in the presence of an alkanethiol capping agent to produce 1-3 nm particles. Nanoparticle sizes can be controlled between 2 and 5 nm by varying the thiol concentration, [Hostetler, M. J; Wingate, J. E.; Zhong, C. J.; Harris, J. E.; Vachet, R. W.; Clark, M R.; Londono, J. D.; Green, S. J.; Stokes, J. I; Wignall, G. D.; Glish, G. L.; Porter, M D.; Evans, N. D.; Murray, R. W. *Langmuir* 1998, 14, 17]. Phosphine-stabilized gold clusters have also been produced and subsequently converted to thiol-capped clusters by ligand exchange in order to improve their stability [Schmid, G.; Pfeil, R.; Boese, R.; Bandrmann, F.; Meyer, S.; Calis, G. H. M; van der Velden, J. W. A. *Chem. Ber.* 1981, 114, 3634; Warner, M G.; Reed, S. M; Hutchison, J. E. *Chem. Mater.* 2000, 12, 3316.] and phosphine-stabilized monodispersed gold particles were prepared using a similar protocol to the Brust method [Weare, W. W; Reed, S. M; Warner, M G.; Hutchison, J. E. *J. Am. Chem. Soc.* 2000, 122, 12890]. See also recent review: Ziyi Zhong, Benoit[1] Male, Keith B.[1] Luong, John H. T, *More Recent Progress in the Preparation of Au Nanostructures, Properties, and Applications, Analytical Letters;* 2003, Vol. 36 Issue 15, p.3097-3118]

Fabrication of Nanoparticle of Metal Coated with Nanoshells of Dyes

The fabrication of metal nanoparticles coated with nanoshells of dye molecules can be performed using the method described by Masuhara et al [AKITO MASUHARA, SATOSHI OHHASHIy, HITOSHI KASAI; SHUJI OKADA, *FABRICATION AND OPTICAL PROPERTIES OF NANOCOMPLEXES COMPOSED OF METAL NANOPARTICLES AND ORGANIC DYES, Journal of Nonlinear Optical Physics & Materials* Vol. 13, Nos. 3 & 4 (2004) 587-592]. Nanocomplexes composed of Ag or Au as a core and 3-carboxlymethyl-5-[2-(3-octadecyl-2-benzoselenazolinylidene) ethylidene]rhodanine (MCSe) or copper (II) phthalocyanine (CuPc) as a shell are prepared by the co-reprecipitation method. In the case of Ag-MCSe nanocomplexes, 0.5 mM acetone solution of MCSe are injected into 10 ml of Ag nanoparticle water dispersion, prepared by the reduction of $AgNO_3$ using $NaBH_4$: Au-MCSe nanocomplexes are also fabricated in a similar manner. A water dispersion of Au nanoparticles was prepared by the reduction of $HAuCl_4$ using sodium citrate. Subsequently, 2 M $NH_4OH$ (50 μl) was added and the mixture was thermally treated at 50° C. This amine treatment often stimulates the J-aggregate formation of MCSe.6 Ag-CuPc and Au-CuPc nanocomplexes were also fabricated in the same manner: 1 mM 1-methyl-2-pyrrolidinone (NMP) solution of CuPc (200 μl) was injected into a water dispersion (10 ml) of Ag or Au nanoparticles.

The present invention treatment may also be used for inducing an auto vaccine effect for malignant cells, including those in solid tumors. To the extent that any rapidly dividing cells or stem cells may be damaged by a systemic treatment, then it may be preferable to direct the stimulating energy directly toward the tumor, preventing damage to most normal, healthy cells or stem cells by avoiding photoactivation or resonant energy transfer of the photoactivatable agent.

Alternatively, a treatment may be applied that slows or pauses mitosis. Such a treatment is capable of slowing the division of rapidly dividing healthy cells or stem cells during the treatment, without pausing mitosis of cancerous cells. Alternatively, a blocking agent is administered preferentially to malignant cells prior to administering the treatment that slows mitosis.

In one embodiment, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death, even if exposed to photoactivated agents, provided that such photoactivated agents degenerate from the excited state to a lower energy state prior to binding, mitosis or other mechanisms for creating damage to the cells of a substantial fraction of the healthy stem cells. Thus, an auto-immune response may not be induced.

Alternatively, a blocking agent may be used that prevents or reduces damage to stem cells or healthy cells, selectively, which would otherwise be impaired. The blocking agent is selected or is administered such that the blocking agent does not impart a similar benefit to malignant cells, for example.

In one embodiment, stem cells are targeted, specifically, for destruction with the intention of replacing the stem cells with a donor cell line or previously stored, healthy cells of the patient. In this case, no blocking agent is used. Instead, a carrier or photosensitizer is used that specifically targets the stem cells.

Work in the area of photodynamic therapy has shown that the amount of singlet oxygen required to cause cell lysis, and thus cell death, is $0.32 \times 10^{-3}$ mol/liter or more, or $10^9$ singlet oxygen molecules/cell or more. However, in one embodiment of the present invention, it is most preferable to avoid production of an amount of singlet oxygen that would cause cell lysis, due to its indiscriminate nature of attack, lysing both target cells and healthy cells. Accordingly, it is most preferred in the present invention that the level of singlet oxygen production caused by the initiation energy used or activatable pharmaceutical agent upon activation be less than level needed to cause cell lysis.

In a further embodiment, methods in accordance with the present invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

An advantage of the methods of the present invention is that by specifically targeting cells affected by a cell proliferation disorder, such as rapidly dividing cells, and triggering a cellular change, such as apoptosis, in these cells in situ, the immune system of the host may be stimulated to have an immune response against the diseased cells. Once the host's own immune system is stimulated to have such a response, other diseased cells that are not treated by the activatable pharmaceutical agent may be recognized and be destroyed by the host's own immune system. Such autovaccine effects may be obtained, for example, in treatments using psoralen and UV-A.

The present invention methods can be used alone or in combination with other therapies for treatment of cell proliferation disorders. Additionally, the present invention methods can be used, if desired, in conjunction with recent advances in chronomedicine, such as that detailed in Giacchetti et al, *Journal of Clinical Oncology*, Vol 24, No 22 (August 1), 2006: pp. 3562-3569. In chronomedicine it has been found that cells suffering from certain types of disorders, such as cancer, respond better at certain times of the day than at others. Thus, chronomedicine could be used in conjunction with the present methods in order to augment the effect of the treatments of the present invention.

In another aspect, the present invention further provides systems and kits for practicing the above described methods.

In one embodiment, a system in accordance with the present invention may include: (1) an initiation energy source; (2) one or more energy modulation agents; and (3) one or more activatable pharmaceutical agents.

In another embodiment, a system in accordance with the present invention may include an initiation energy source and one or more activatable pharmaceutical agents.

In preferred embodiments, the initiation energy source may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.).

In other embodiments, endoscopic or laproscopic devices equipped with appropriate initiation energy emitter may be used as the initiation energy source. In such systems, the initiation energy may be navigated and positioned at the pre-selected coordinate to deliver the desired amount of initiation energy to the site.

In further embodiments, dose calculation and robotic manipulation devices may also be included in the system.

The reagents and chemicals useful for methods and systems of the present invention may be packaged in kits to facilitate application of the present invention. In one exemplary embodiment, a kit including a psoralen, and fractionating containers for easy fractionation and isolation of autovaccines is contemplated. A further embodiment of kit would comprise at least one activatable pharmaceutical agent capable of causing a predetermined cellular change, at least one energy modulation agent capable of activating the at least one activatable agent when energized, at least one plasmonics agent and containers suitable for storing the agents in stable form, and preferably further comprising instructions for administering the at least one activatable pharmaceutical agent, at least one plasmonics agent and at least one energy modulation agent to a subject, and for app Lying an initiation energy from an initiation energy source to activate the activatable pharmaceutical agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

Having generally described this invention, a further understanding can be obtained by reference to certain specific examples which are provided herein for purposes of illustration only and are not intended to be limiting unless otherwise specified.

Examples

Preparation of Silver Nanoparticles

Silver (or gold) colloids were prepared according to the standard Lee-Meisel method: 200 mL of $10^{-3}$ M AgNO$_3$ aqueous solution was boiled under vigorous stirring, then 5 mL of 35-mM sodium citrate solution were added and the resulting mixture was kept boiling for 1 h. This procedure was reported to yield ~$10^{11}$ particles/mL of homogenously sized colloidal particles with a diameter of ~35-50 nm and an absorption maximum at 390 nm. The colloidal solutions were stored at 4° C. and protected from room light. Further dilutions of the colloidal solutions were carried out using distilled water.

Fabrication/Preparation of Metal Nanocaps

One approach has involved the use of nanospheres spin-coated on a solid support in order to produce and control the desired roughness. The nanostructured support is subsequently covered with a layer of silver that provides the conduction electrons required for the surface plasmon mechanisms. Among the techniques based on solid substrates, the methods using simple nanomaterials, such as Teflon or latex nanospheres, appear to be the simplest to prepare. Teflon and latex nanospheres are commercially available in a wide variety of sizes. The shapes of these materials are very regular and their size can be selected for optimal enhancement. These materials comprise isolated dielectric nanospheres (30-nm diameter) coated with silver producing systems of half-nanoshells, referred to as nanocaps.

FIG. 24 shows a scanning electron micrograph (SEM) of 300-nm diameter polymer nanospheres covered by a 100-nm thick silver nanocaps (half-nanoshell) coating. The nanoparticles can be sonicated to release them from the underlying substrate. The effect of the sphere size and metal layer thickness upon the SERS effect can be easily investigated. The silver coated nanospheres were found to be among the most plasmonics-active investigated. Gold can also be used instead of silver to coat over nanoparticles comprising PA drug molecules.

Fabrication of Gold Nanoshells

Gold nanoshells have been prepared using the method described by Hirsch et al. [Hirsch L R, Stafford R J, Bankson J A, Sershen S R, Price R E, Hazle J D, Halas N J, West J L (2003) Nanoshell-mediated near infrared thermal therapy of tumors under MR Guidance. Proc Natl Acad Sci 100: 13549-13554] using a mechanism involving nucleation and then successive growth of gold nanoparticles around a silica dielectric core. Gold nanoparticles, the seed, prepared as described above using the Frens method, were used to grow the gold shell. Silica nanoparticles (100 nm) used for the core of the nanoshells were monodispersed in solution of 1 APTES in EtOH. The gold "seed" colloid synthesized using the Frens method were grown onto the surface of silica nanoparticles via molecular linkage of amine groups. The "seed" covers the aminated silica nanoparticle surface, first as a discontinuous gold metal layer gradually growing forming a continuous gold shell. Gold nanoparticles used as the "seed" were characterized using optical transmission spectroscopy (UV-Vis Spectrophotometer, Beckman Coulter, Fullerton, Calif.) and atomic force microscopy (Atomic Force Microscope, Veeco Instruments, Woodbury, N.Y.) while gold nanoshells were characterized using optical transmission spectroscopy and scanning electron microscopy (Scanning Electron Microscope, Hitachi S-4700, Hitachi High Technologies America, Inc. Pleasanton, N.Y.).

Probe for Measurement of Apoptosis with the PDT Drug ALA

A method has been developed using nanosensors that can be used to evaluate the effectiveness of PEPST probes. Although one can use conventional methods (not requiring nanosensors), we describe the nanosensor method previously developed [P. M Kasili, J. M Song, and T Vo-Dinh, "Optical Sensor for the Detection of Caspase-9 Activity in a Single Cell", J. Am. Chem. Soc., 126, 2799-2806 (2004)]. The method comprises measuring caspases activated by apoptosis induced by the photoactive drugs. In this experiment, we measure two sets of cells I and II. Set I is treated with the drug ALA and set II is treated by the drug ALA conjugated to a PEPST probe described in the previous section. By comparing the results (amount of Caspases detected), one can evaluate the efficiency of the PEPST-ALA drug compared to ALA alone.

In the classical model of apoptosis, caspases are divided into initiator caspases and effector caspases according to their function and their sequence of activation. Initiator caspases include caspase-8, -9, while effector caspases include, caspases-3, -6 and -7. The activation of caspases is one of the earliest biomarkers of apoptosis making caspases an early and ideal target for measuring apoptosis. Apoptosis, or programmed cell death, is a mode of cell death characterized by specific morphological and biochemical features. The results obtained in these experiments can be used to evaluate the effectiveness of phototherapeutic drugs that induce apoptosis (e.g. PDT drugs). Since caspases play a central role in the induction of apoptosis, tetrapeptide-based optical nanosensors were used to determine their role in response to a photodynamic therapy (PDT) agent, δ-aminolevulinic acid (ALA) in the well-characterized human breast carcinoma cell line, MCF-7. MCF-7 cells were exposed to the photosensitizer ALA to explore ALA-PDT induced apoptosis by monitoring caspase-9 and caspase-7 activity. Caspase-9 and caspase-7 protease activity was assessed in single living MCF-7 cells with the known caspase-9 and caspase-7 substrates, Leucine-aspartic-histidine-glutamic acid 7-amino-4-methylcoumarin (LEHD-AMC) and aspartic-glutamic acid-valine-aspartic acid 7-amino-4-methylcoumarin (DEVD-AMC) respectively, covalently immobilized to the nanotips of optical nanosensors. Upon the induction of apoptosis, activated target caspases recognize the tetrapeptide sequence and specifically cleaves it. The recognition of substrate by caspases is immediately followed by a cleavage reaction yielding the fluorescent AMC which can be excited with a Helium-Cadmium (HeCd) laser to generate a measurable fluorescence signal. By comparing the fluorescence signal generated from AMC within cells with activated caspases and from those with inactive caspases, we are able to successfully detect caspase activity within a single living MCF-7 cell.

Chemicals and Reagents

δ-aminolevulinic acid (ALA), phosphate buffered saline (PBS), hydrochloric acid (HCl), nitric acid ($HNO_3$), Glycidoxypropyltrimethoxysilane (GOPS), 1,1'-Carbonyldiimidazole (CDI), and anhydrous acetonitrile were purchased from Sigma-Aldrich, St. Louis, Mo. Caspase-9 substrate, LEHD-7-amino-4-methylcoumarin (AMC), Caspase-7 substrate, DEVD-7-amino-4-methylcoumarin (AMC), 2× reaction buffer, dithiothreitol (DTT), and dimethylsulfoxide (DMSO) were purchased from BD Biosciences, Palo Alto. Calif.

Cell Lines

Human breast cancer cell line, MCF-7, was obtained from American Type Culture Collection (Rockville, Md., USA, Cat-no. HTB22). MCF-7 cells were grown in Dulbecco's Modified Eagle's Medium ((DMEM) (Mediatech, Inc., Herndon, Va.)) supplemented with 1 mM L-glutamine (Gibco, Grand Island, N.Y.) and 10% fetal bovine serum (Gibco, Grand Island, N.Y.). Cell culture was established in growth medium (described above) in standard T25 tissue culture flasks (Corning, Corning, N.Y.). The flasks were incubated in a humidified incubator at 37° C., 5% $CO_2$ and 86% humidity. Cell growth was monitored daily by microscopic observation until a 60-70% state of confluence was achieved. The growth conditions were chosen so that the cells would be in log phase growth during photosensitizer treatment with ALA, but would not be so close to confluence that a confluent monolayer would form by the termination of the chemical exposure. In preparation for experiments, cells were harvested from the T25 flasks and 0.1 ml ($10^5$ cells/ml) aliquots were seeded into 60 mm tissue culture dishes (Corning Costar Corp., Corning, N.Y.) for overnight attachment. The MCF-7 cells were studied as four separate groups with the first group, Group I, being the experimental, exposed to 0.5 mM ALA for 3 h followed by photoactivation ([+]ALA[+]PDT). This involved incubating the cells at 37° C. in 5% $CO_2$ for 3 h with 0.5 mM ALA. Following incubation the MCF-7 cells were exposed to red light from a HeNe laser ($\lambda$ 632.8 nm, <15 mW, Melles Griot, Carlsbad, Calif.) positioned about 5.0 cm above the cells for five minutes at a fluence of 5.0 $mJ/cm^2$ to photoactivate ALA and subsequently induce apoptosis. The second and third groups, Group II and III respectively, served as the "treated control" and were exposed to 0.5 mM ALA for 3 hours without photoactivation ([+]ALA[−]PDT) and photoactivation without 0.5 mM ALA ([−]ALA[+]PDT) respectively. The fourth group, Group IV was the "untreated control," which received neither ALA nor photoactivation ([−]ALA[−]PDT Experimental Protocol Preparation of Enzyme Substrate-Based Optical Nanosensors Briefly, this process involved cutting and polishing plastic clad silica (PCS) fibers with a 600-µm-size core (Fiberguide Industries, Stirling, N.J.). The fibers were pulled to a final tip diameter of 50 nm and then coated with ~100 nm of silver metal (99.999% pure) using a thermal evaporation deposition system (Cooke Vacuum Products, South Norwalk, Conn.) achieving a final diameter of 150 nm. The fused silica nanotips were acid-cleaned ($HNO_3$) followed by several rinses with distilled water. Finally, the optical nanofibers were allowed to air dry at room temperature in a dust free environment. The nanotips were then silanized and treated with an organic coupling agent, 10% Glycidoxypropyltrimethoxysilane (GOPS) in distilled water. The silanization agent covalently binds to the silica surface of the nanotips modifying the hydroxyl group to a terminus that is compatible with the organic cross-linking reagent, 1'1, Carbonyldiimidazole (CDI). The use of CDI for activation introducing an imidazole-terminal group was particularly attractive since the protein to be immobilized could be used without chemical modification. Proteins bound using this procedure remained securely immobilized during washing or subsequent manipulations in immunoassay procedures, as opposed to procedures that use adsorption to attach proteins. The silanized and activated nanotips for measuring caspase-9 activity were immersed in a solution containing DMSO, 2× reaction buffer, PBS, and LEHD-AMC, and allowed to incubate for 3 h at 37° C., while those for measuring caspase-7 activity were immersed in a solution containing DMSO, 2× reaction buffer, PBS, and DEVD-AMC, and allowed to incubate for 3 h at 37° C.

Measurement System and Procedure

A schematic representation of the experimental setup used in this work is described in a previous work [[P. M Kasili, J. M Song, and T Vo-Dinh, "*Optical Sensor for the Detection of Caspase-9 Activity in a Single Cell*", J. Am. Chem. Soc., 126, 2799-2806 (2004)]. The components included a HeCd laser (Omnichrome, <5 mW laser power) for excitation, an optical fiber for delivery of excitation light to the optical nanosensor, a Nikon Diaphot 300 inverted fluorescence microscope (Nikon, Inc., Melville, N.Y.), a photon counting photomultiplier tube (PMT) and a PC for data acquisition and processing. This experimental set-up, used to probe single cells, was adapted for this purpose from a standard micromanipulation and microinjection apparatus. The Nikon Diaphot 300 inverted microscope was equipped with a Diaphot 300/Diaphot 200 Incubator to maintain the cell cultures at 37° C. on the microscope stage, during these experiments. The micromanipulation equipment consisted of MN-2 (Narishige Co. Ltd., Tokyo, Japan) Narishige three-dimensional manipulators for coarse adjustment, and Narishige MMW-23 three-dimensional hydraulic micromanipulators for fine adjustments. The optical nanosensor was mounted on a micropipette holder (World Precision Instruments, Inc., Sarasota, Fla.). The 325 nm laser line of a HeCd laser was focused onto a 600-µm-delivery fiber that is terminated with a subminiature A (SMA) connector. The enzyme substrate-based optical nanosensor was coupled to the delivery fiber through the SMA connector and secured to the Nikon inverted microscope with micromanipulators. To record the fluorescence generated by AMC molecules at the nanotips, a Hamamatsu PMT detector assembly (HC125-2) was mounted in the front port of the Diaphot 300 microscope. The fluorescence emitted by AMC from the measurement made using single live cells was collected by the microscope objective and passed through a 330-380 nm filter set and then focused onto a PMT for detection. The output from the PMT was recorded using a universal counter interfaced to a personal computer (PC) for data treatment and processing.

In Vitro Determination of Caspase Activity

After incubation using the following treatment groups, group (I) −[+]ALA[+]PDT, group II −[+]ALA[−]PDT, group III −[−]ALA[+]PDT, and group IV −[−]ALA[−]PDT, MCF-7 cells were washed with PBS solution, pH 7.4, and then resuspended in lysis buffer (100 mM HEPES, pH 7.4, 10% sucrose, 0.1% 3-[(3-cholamidopropyl)-dimethylammonio]-1-propanesulfonate (CHAPS), 1 mM EDTA, 10 mM dithiothreitol (DTT), 1 mM phenylmethylsulphonyl fluoride (PMSF), 10 mg/ml pepstatin, 10 mg/ml leupeptin) and left on ice for 45 minutes. The cells were then repeatedly passed through a syringe with a 25-gauge needle until most of the cell membrane was disrupted, and centrifuged at 1500 RPM for 10 min. Activity of caspases was measured using the fluorogenic substrate peptides; LEHD-AMC for caspase-9 and DEVD-AMC for caspase-7. The release of AMC was measured after incubating optical nanosensors in picofuge tubes containing the cell lysates from the various treatment groups and using a HeCd laser (excitation 325 nm) to excite AMC. Caspase activity was expressed as fluorescence intensity of AMC as a function of equivalent nanomoles of LEHD-AMC and DEVD-AMC respectively.

The results of the in vitro measurement of caspase-9 and caspase-7 activity were plotted. The curves for each fluorescent measurement of AMC were plotted for each as a function of AMC concentration. Caspase-9 activity was determined by incubation of optical nanosensors with the substrate LEHD-7-amino-4-methylcoumarin (AMC) in cell lysate (~$10^5$ cells) obtained from the following treatment groups; group I, II, III and IV, described earlier in the article. The release of AMC was measured after excitation using HeCd laser (325 nm) and collecting the fluorescence signal using a 380 nm longpass filter. The peak emission wavelength of AMC is about 440 nm. Likewise, Caspase-7 activity was determined by incubation in cell lysate (~$10^5$ cells) obtained from the following treatment groups I, II, III, and IV. The release of AMC was measured after excitation using a HeCd laser (325 nm) and collecting the fluorescence signal using a 380 nm longpass filter.

In this experiment, we measure two sets of cells I and II: (1) Set I is treated with the drug ALA and (2) set II is treated by the drug ALA conjugated to a PEPST probe described in the previous section. By comparing the results (amount of caspase detected), one can evaluate the efficiency of the PEP ST-ALA drug compared to ALA alone.

Additional modifications and variations of the present invention are possible in light of the above teachings. It is therefore to be understood that within the scope of the appended claims, the invention may be practiced otherwise than as specifically described herein.

The invention claimed is:

1. A method for neuronal stimulation in a subject, comprising:
   administering at least one biocompatible phosphorescent molecule to a region of a subject in need of neuronal stimulation, wherein the at least one biocompatible phosphorescent molecule is selected to have an emitted energy to be of a wavelength sufficient to cause the neuronal stimulation and increases a wavelength of an X-ray initiation energy; and
   applying the X-ray initiation energy from at least one source, wherein the X-ray initiation energy is converted by the at least one biocompatible phosphorescent molecule into the emitted energy that directly causes neuronal stimulation in the region of the subject.

2. The method of claim 1, wherein said initiation energy is applied from a single source.

3. The method of claim 1, wherein said initiation energy is applied from more than one source.

4. The method of claim 1, wherein the subject has Parkinson's disease.

5. The method of claim 1, wherein the initiation energy is generated in-situ in the subject.

6. The method of claim 1, wherein the at least one biocompatible phosphorescent molecule is activated prior to the administration to the region of the subject and after the administration, the activated biocompatible phosphorescent molecule emits the emitted energy that causes the neuronal stimulation.

* * * * *